(12) United States Patent
McQuilkin et al.

(10) Patent No.: US 11,422,030 B2
(45) Date of Patent: Aug. 23, 2022

(54) SPECTRAL IMAGING SYSTEM FOR REMOTE AND NONINVASIVE DETECTION OF TARGET SUBSTANCES USING SPECTRAL FILTER ARRAYS AND IMAGE CAPTURE ARRAYS

(71) Applicant: InnoPix, Inc., Plymouth, MN (US)

(72) Inventors: Gary L. McQuilkin, Plymouth, MN (US); Gregory L. Engelke, New Brighton, MN (US)

(73) Assignee: INNOPIX, INC., Plymouth, MN (US)

( * ) Notice: Subject to any disclaimer, the term of this patent is extended or adjusted under 35 U.S.C. 154(b) by 0 days.

(21) Appl. No.: 17/187,078

(22) Filed: Feb. 26, 2021

(65) Prior Publication Data
US 2021/0181020 A1 Jun. 17, 2021

Related U.S. Application Data

(60) Division of application No. 16/847,997, filed on Apr. 14, 2020, now Pat. No. 10,935,427, which is a
(Continued)

(51) Int. Cl.
*G01N 21/25* (2006.01)
*G01J 3/12* (2006.01)
(Continued)

(52) U.S. Cl.
CPC .............. *G01J 3/12* (2013.01); *A61B 5/0075* (2013.01); *G01J 3/0205* (2013.01);
(Continued)

(58) Field of Classification Search
CPC ........ G01J 3/26; G01J 3/02; G01J 3/51; G01J 9/00; G01N 21/255
(Continued)

(56) References Cited

U.S. PATENT DOCUMENTS 4,182,571 A 1/1980 Naofumi et al.
6,111,640 A 8/2000 Hedman et al.
(Continued)

FOREIGN PATENT DOCUMENTS

WO WO 2013047627 4/2013
WO WO 2013064511 5/2013
WO WO 2013/116316 8/2013

OTHER PUBLICATIONS

Ahlberg, Liz, Cradle Turns Smartphone into Handheld Biosensor, Inside Illinois, vol. No. 22, pp. 1-12, Jun. 6, 2013.
(Continued)

*Primary Examiner* — Md M Rahman
(74) *Attorney, Agent, or Firm* — Kagan Binder, PLLC

(57) ABSTRACT

An approach to noninvasively and remotely detect the presence, location, and/or quantity of a target substance in a scene via a spectral imaging system comprising a spectral filter array and image capture array. For a chosen target substance, a spectral filter array is provided that is sensitive to selected wavelengths characterizing the electromagnetic spectrum of the target substance. Elements of the image capture array are optically aligned with elements of the spectral filter array to simultaneously capture spectrally filtered images. These filtered images identify the spectrum of the target substance. Program instructions analyze the acquired images to compute information about the target substance throughout the scene. A color-coded output image may be displayed on a smartphone or computing device to indicate spatial and quantitative information about the detected target substance. The system desirably includes a library of interchangeable spectral filter arrays, each sensitive to one or more target substances.

22 Claims, 38 Drawing Sheets

Related U.S. Application Data continuation of application No. 16/291,458, filed on Mar. 4, 2019, now Pat. No. 10,656,015, which is a continuation of application No. 15/379,059, filed on Dec. 14, 2016, now Pat. No. 10,222,260, which is a division of application No. 14/742,074, filed on Jun. 17, 2015, now Pat. No. 9,551,616.

(60) Provisional application No. 62/014,004, filed on Jun. 18, 2014.

(51) Int. Cl.

| | |
|---|---|
| *A61B 5/00* | (2006.01) |
| *G01J 3/28* | (2006.01) |
| *G01J 3/36* | (2006.01) |
| *G01J 3/02* | (2006.01) |
| *G01N 21/31* | (2006.01) |
| *G02B 5/20* | (2006.01) |
| *A61B 5/145* | (2006.01) |
| *G01N 21/17* | (2006.01) |

(52) U.S. Cl.
CPC ........... *G01J 3/0272* (2013.01); *G01J 3/0297* (2013.01); *G01J 3/2803* (2013.01); *G01J 3/2823* (2013.01); *G01J 3/36* (2013.01); *G01N 21/255* (2013.01); *G01N 21/31* (2013.01); *G02B 5/201* (2013.01); *A61B 5/14507* (2013.01); *A61B 5/14542* (2013.01); *A61B 5/444* (2013.01); *A61B 2576/00* (2013.01); *G01J 2003/123* (2013.01); *G01J 2003/1213* (2013.01); *G01J 2003/1239* (2013.01); *G01J 2003/2826* (2013.01); *G01N 2021/1793* (2013.01); *G01N 2021/3137* (2013.01); *G01N 2201/129* (2013.01)

(58) Field of Classification Search
USPC ........................................................ 356/416
See application file for complete search history.

(56) References Cited

U.S. PATENT DOCUMENTS

| | | | |
|---|---|---|---|
| 6,160,902 | A | 12/2000 | Dickson et al. |
| 6,366,681 | B1 | 4/2002 | Hutchins |
| 6,490,075 | B1 | 12/2002 | Scheps et al. |
| 6,611,289 | B1 | 8/2003 | Yu et al. |
| 6,639,665 | B2 | 10/2003 | Poole |
| 7,149,366 | B1 | 12/2006 | Sun |
| 7,446,299 | B2 | 11/2008 | Kobayashi |
| 8,109,634 | B2 | 2/2012 | Gil |
| 8,126,213 | B2 | 2/2012 | Chao et al. |
| 8,159,525 | B2 | 4/2012 | Park et al. |
| 8,224,425 | B2 | 7/2012 | Freeman et al. |
| 8,320,996 | B2 | 11/2012 | Panasyuk et al. |
| 8,374,682 | B2 | 2/2013 | Freeman et al. |
| 8,665,440 | B1 | 3/2014 | Kompaniets et al. |
| 9,541,495 | B2 | 1/2017 | Ohtomo et al. |
| 2001/0016053 | A1 | 8/2001 | Dickson et al. |
| 2002/0049386 | A1 | 4/2002 | Herman et al. |
| 2003/0006170 | A1 | 1/2003 | Lawandy |
| 2003/0030801 | A1 | 2/2003 | Levenson et al. |
| 2004/0101210 | A1 | 5/2004 | Weinstein et al. |
| 2005/0104771 | A1 | 5/2005 | Terry et al. |
| 2006/0247514 | A1 | 11/2006 | Panasyuk et al. |
| 2007/0016079 | A1 | 1/2007 | Freeman et al. |
| 2007/0232930 | A1 | 10/2007 | Brand et al. |
| 2007/0249913 | A1 | 10/2007 | Freeman et al. |
| 2009/0295910 | A1 | 12/2009 | Mir et al. |
| 2009/0326383 | A1 | 12/2009 | Barnes et al. |
| 2012/0061586 | A1 | 3/2012 | Yao et al. |
| 2012/0200682 | A1 | 8/2012 | Mestha et al. |
| 2013/0094717 | A1 | 4/2013 | Janni et al. |
| 2013/0137949 | A1 | 5/2013 | Freeman et al. |
| 2014/0022381 | A1 | 1/2014 | Heinhold |
| 2014/0232858 | A1 | 8/2014 | Ohtomo et al. |
| 2015/0092099 | A1 | 4/2015 | Shen et al. |

OTHER PUBLICATIONS

Ashraf, Muhammad Aqeel, Maah, Mohd. Jamil, and Yusoff, Ismail, ed. Islam Atazadeh, Chapter 8, Introduction to Remote Sensing of Biomass [spectra: dry grass, green grass, soil], *Biomass and Remote Sensing of Biomass,* ISBN 978-953-307-490-0, Sep. 6, 2011 (1 page); doi: 10.5772/16462, http://www.intechopen.com/books/biomass-and-remote-sensing-of-biomass/introduction-to-remote-sensing-of-biomass.

Asner, Gregory P., Biophysical and Biochemical Sources of Variability in Canopy Reflectance, *Remote Sens. Environ.,* 64:234-253, 1998.

Borah, et al., [Spectra of various light sources], *EURASIP Journal on Wireless Communications and Networking* 2012 (1 pg.) 2012:91 doi:10.1186/1687-1499-2012-91.

CCD sensor spectral sensitivity, http://www.gitthailand.com/Lighting_for_Machine_Vision.php—viewed Sep. 16, 2015, and elsewhere prior to Jun. 18, 2014 (1 pg.).

Cerussi A, Hsiang, D., Shah, N., Mehta, R., Durkin, A., Butler, J., Tromberg, B., Predicting Response to Breast Cancer Neoadjuvant Chemotherapy Using Diffuse Optical Spectrscopy, *Proc. Natl. Acad. Sci. U. S. A.,* 104(10): 4014-4019, 2007.

Chao K, Nou X, Liu Y, Kim MS, Chan DE, Yang CC, Patel J, Sharma M, Detection of Fecal/Ingesta Contaminants on Poultry Processing Equipment Surfaces by Visible and Near-Infrared Reflectance Spectroscopy, *Applied Engineering in Agriculture,* American Society of Agricultural and Biological Engineers, vol. 24(1): 49-55, 2008.

Crysta-Lyn Chemical Company: Manufacturer of NIR, Visible, UV Laser Dyes and Absorbers, Crysta-Lyn Chemical Company History, web site: http://www.crystalyn.com/about_us_crystalyn.html—viewed Sep. 14, 2015 (pp. 1-2).

Curtin, Adrian, File:Oxy and Deoxy Hemoglobin Near-Infrared absorption spectra.png; *Wikimedia Commons;* https://commons.wikimedia.org/wiki/File:Oxy_and_Deoxy_Hemoglobin_Near-Infrared_absorption_spectra.png, Aug. 2, 2012 (1 pg.).

Heuveling DA, Visser GW, de Groot M, de Boer JF, Baclayon M, Roos WH, Wuite GJ, Leemans CR, de Bree R, van Dongen GA, Nanocolloidal Albumin-Irdye 800CW: A Near-Infrared Fluorescent Tracer with Optimal Retention in the Sentinel Lymph Node, *Eur J Nucl Med Mol Imaging.* Jul. 2012; 39: 1161-1168.

Jun, Won; Kim, Moon S.; Lee, Kangjin; Milner, Patricia; and Chao, Kuanglin; Assessment of Bacterial Biofilm on Stainless Steel by Hyperspectral Fluorescent *Imaging, Sens. & Instrum. Food Qual.,* 2009, 3:41-48.

Kim, Moon S., Tu, Shu-I, Chao, Kaunglin, Development of real-time line-scan hyperspectral imaging system for online agricultural and food product inspection, Proc. SPIE 7676, *Sensing for Agriculture and Food Quality and Safety II,* Conference vol. 7676, Sensing for Agriculture and Food Quality and Safety II, Orlando, Florida, Apr. 5, 2010, doi:10.1117/12.850460 (Abstract, 1 p.).

Lawrence, K.C., Smith, D.P., Windham, W.R., Heitschmidt, G.W. & Park, B., Egg Embryo Development Detection With Hyperspectral Imaging. *Internation Journal of Poultry Science,* 2006, 5(10): 964-969.

Mieog, J. Sven D.; Troyan, Susan L.; Hutteman, Merlijn; Donohoe, Kevin J.; van der Vorst, Joost R.; Stockdale, Alan; Liefers, Gerrit-Jan; Choi, Hak Soo; Gibbs-Strauss, Summer L.; Putter, Hein; Gioux, Sylvain; Kuppen, Peter J. K.; Ashitate, Yoshitomo; Löwik, Clemens W. G. M.; Smit, Vincent T. H. B. M.; Oketokoun, Rafiou; Ngo, Long H.; van de Velde, Cornelis J. H.; Frangioni, John V.; and Vahrmneijer, Alexander L.; Toward Optimization of Imaging System and Lymphatic Tracer for Near-Infrared Fluorescent Sentinel Lymph Node Mapping in Breast Cancer; *Annals of Surgical Oncology,* Mar. 1, 2011, doi: 10.1245/s10434-011-1566-x (pp. 1-16).

Noncitrus Fruits and Nuts, 2012 Preliminary Summary (Jan. 2013), USDA, National Agricultural Statistics Service (pp. 1-80).

(56) References Cited

OTHER PUBLICATIONS

Park B; Windham WR; Lawrence KC; Smith DP, Contaminant Classification of Poultry Hyperspectral Imagery using a Spectral Angle Mapper Algorithm, *Biosystems Engineering*, vol. 96(3), 323-333, 2007.

Qin J, Chao K, Kim MS, Kang S, Cho BK, Jun W, Detection of Organic Residues on Poultry Processing Equipment Surfaces by LED-Induced Fluorescent Imaging, *Applied Engineering in Agriculture*, American Society of Agricultural and Biological Engineers ISSN 0883-8542, vol. 27(1): 153-161, 2011.

Rajchard, J., Ultraviolet (UV) Light Perception by Birds: A Review, Veterinami Medicina, 54, 2009 (8): 351-359.

Retinal image, http://www.photonetc.com/EN/APPLICATION/Health/RETINAL_IMAGING-78—viewed prior to Jun. 18, 2014 (pp. 1-2).

Smith, D.P., Lawrence, K.C., and Heitschmidt, G. W., Detection of Hatching and Table Egg Defects Using Hyperspectral Imaging, USDA, Agricultural Research Service, Russell Research Center, Athens, GA, USA, Jan. 2006 (pp. 1-20).

Ulrich, Tom, [snow and ice spectra], Quantifying Spectral Diversity within a MODIS Footprint—Goetz Recipient Research in the Himalayas, The NIR Community from ASD Inc., *a PANalytical company*, Posted on Tue, Jan. 22, 2013 @ 04:36 AM, web site: http://discover.asdi.com/bid/93042/Quantifying-Spectral-Diversity-within-a-MODIS-Footprint-Goetz-Recipient-Research-in-the-Himalayas—viewed Sep. 14, 2015 (pp. 1-4).

Urine absorbance spectrum, http://biotechnology.tbzmed.ac.ir/?pageid=22—viewed prior to Jun. 18, 2014 (1 pg.).

Utah State University, Cooperative Extension/NASA, [vegetation spectra], http://extension.usu.edu/nasa/—viewed prior to Jun. 18, 2014 (1 pg.).

Virtual Labs, http://cse21-iiith.virtual-labs.ac.in/exp3/index.php?section=Theory—vegetation spectra viewed Sep. 16, 2015, viewed on different, expired site prior to Jun. 18, 2014 (pp. 1-4).

Water absorbance spectrum, http://www.inspectiontechnologies.co.uk/ITL%20EYE%20SPY.html, viewed prior to Jun. 18, 2014 (1 pg).

Zhang, W, Pan, L, Tu, K, Zhang, Q, Liu, M (2014) Comparison of Spectral and Image Morphological Analysis for Egg Early Hatching Property Detection Based on Hyperspectral Imaging, *PLoS ONE* 9(2): e88659, Feb. 13, 2014, doi:10.1371/journal.pone.0088659 (pp. 1-10).

Zitova, Barbara, Flusser, Jan, Image Registration Methods: a Survey, *Image and Vision Computing*, 21: 977-1000, 2003.

Zuzak, Karel, Francis, Robert, Smith, Jack, Tracy, Chad, Cadeddu, Jeffrey, and Livingston, Edward, Novel Hyperspectral Imager Aids Surgeons, *SPIE Newsroom*, 2008, 10.1117/2.1200812.1394 (pp. 1-5).

Supplementary European Search Report, EP Application No. EP 15810439, dated Jan. 18, 2018, 2 pages.

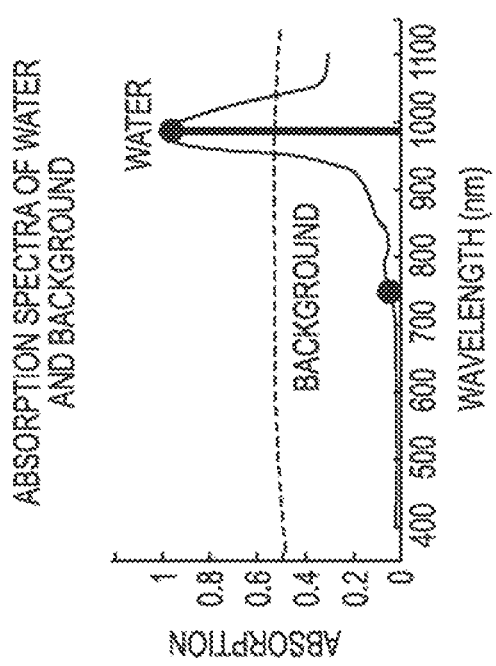

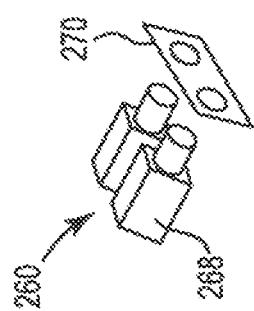
Fig. 6
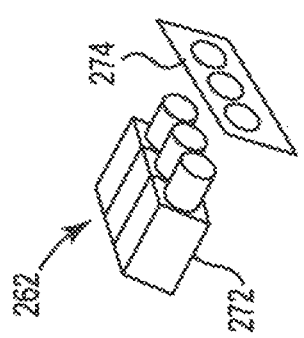
Fig. 7
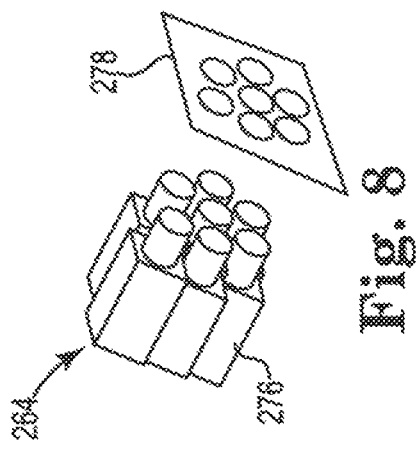
Fig. 8
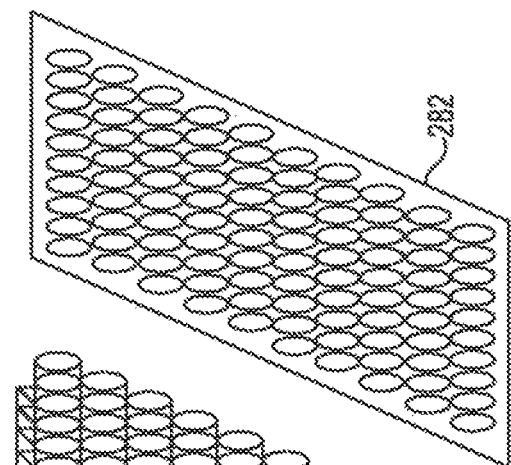
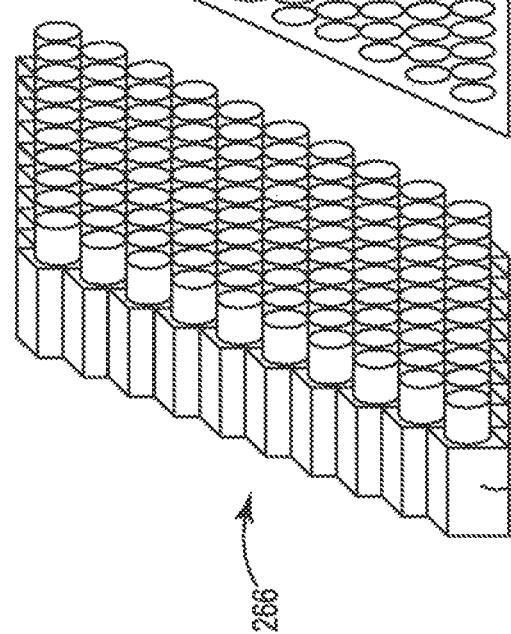
Fig. 9

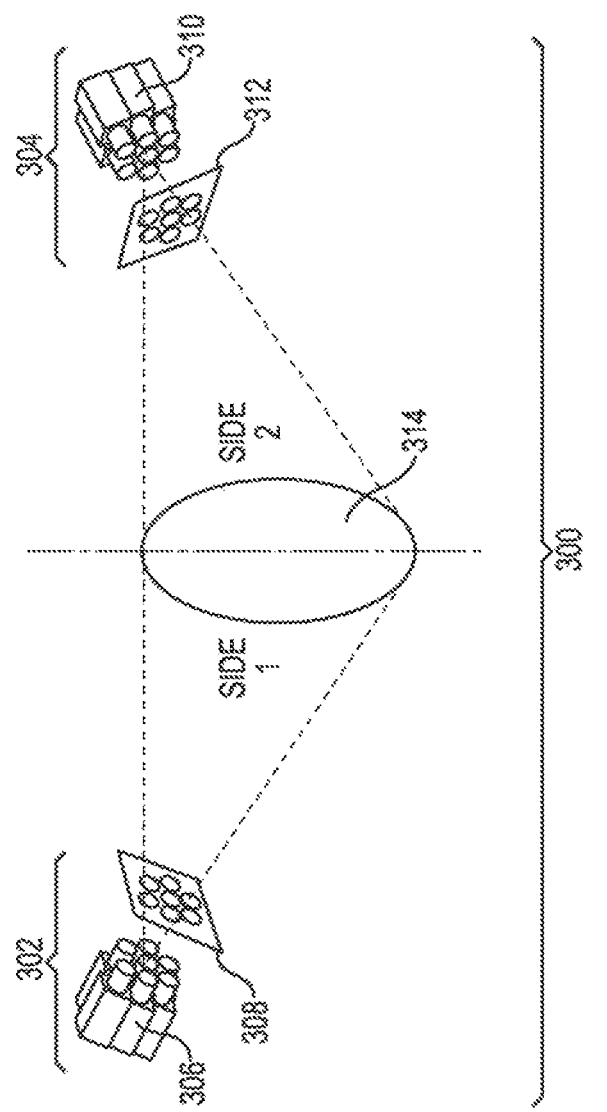

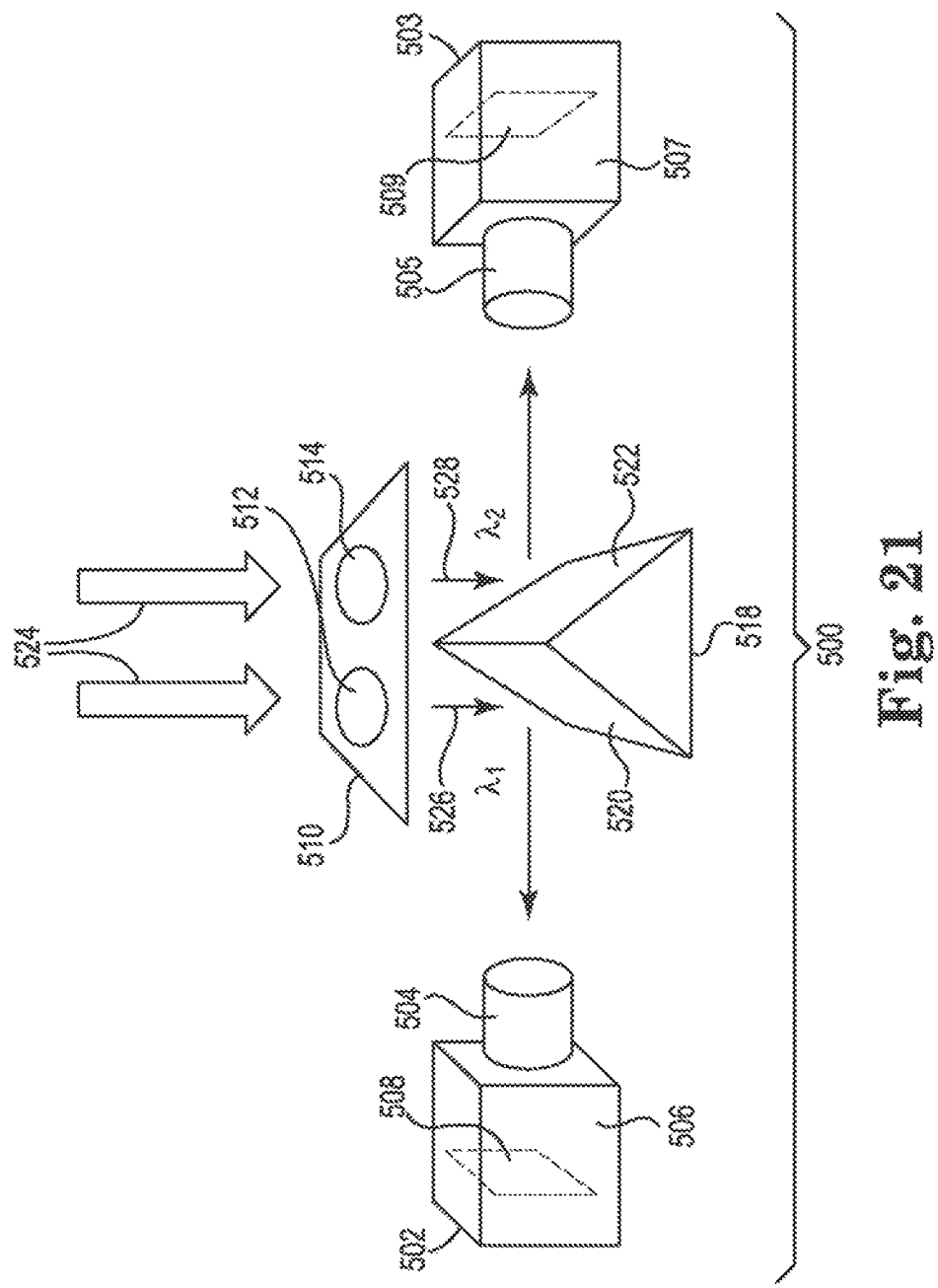

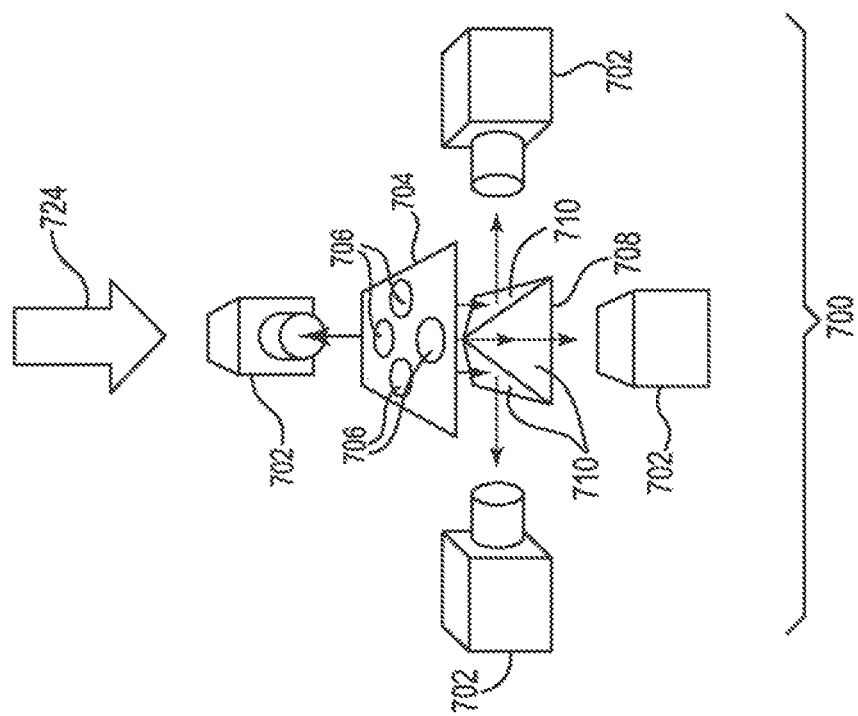
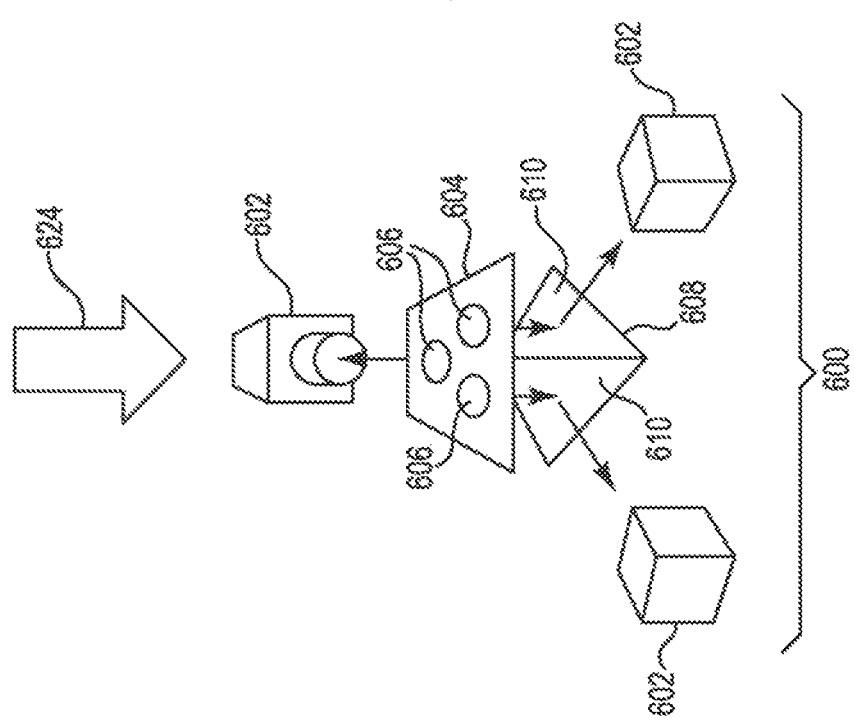

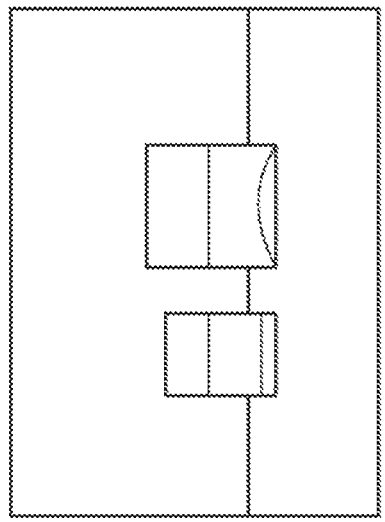
Fig. 25A
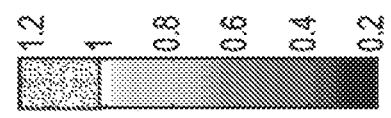
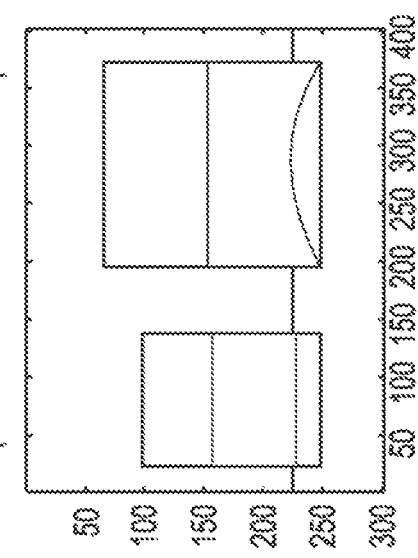
Fig. 25C
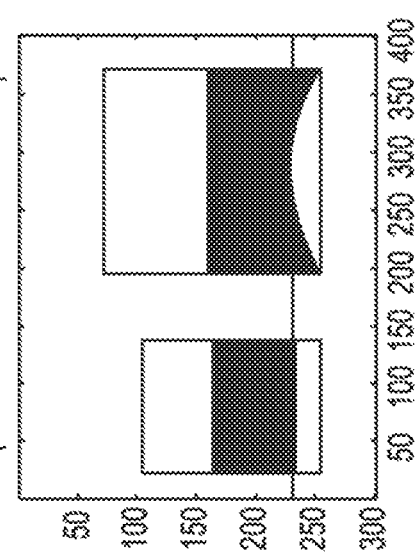
Fig. 25B

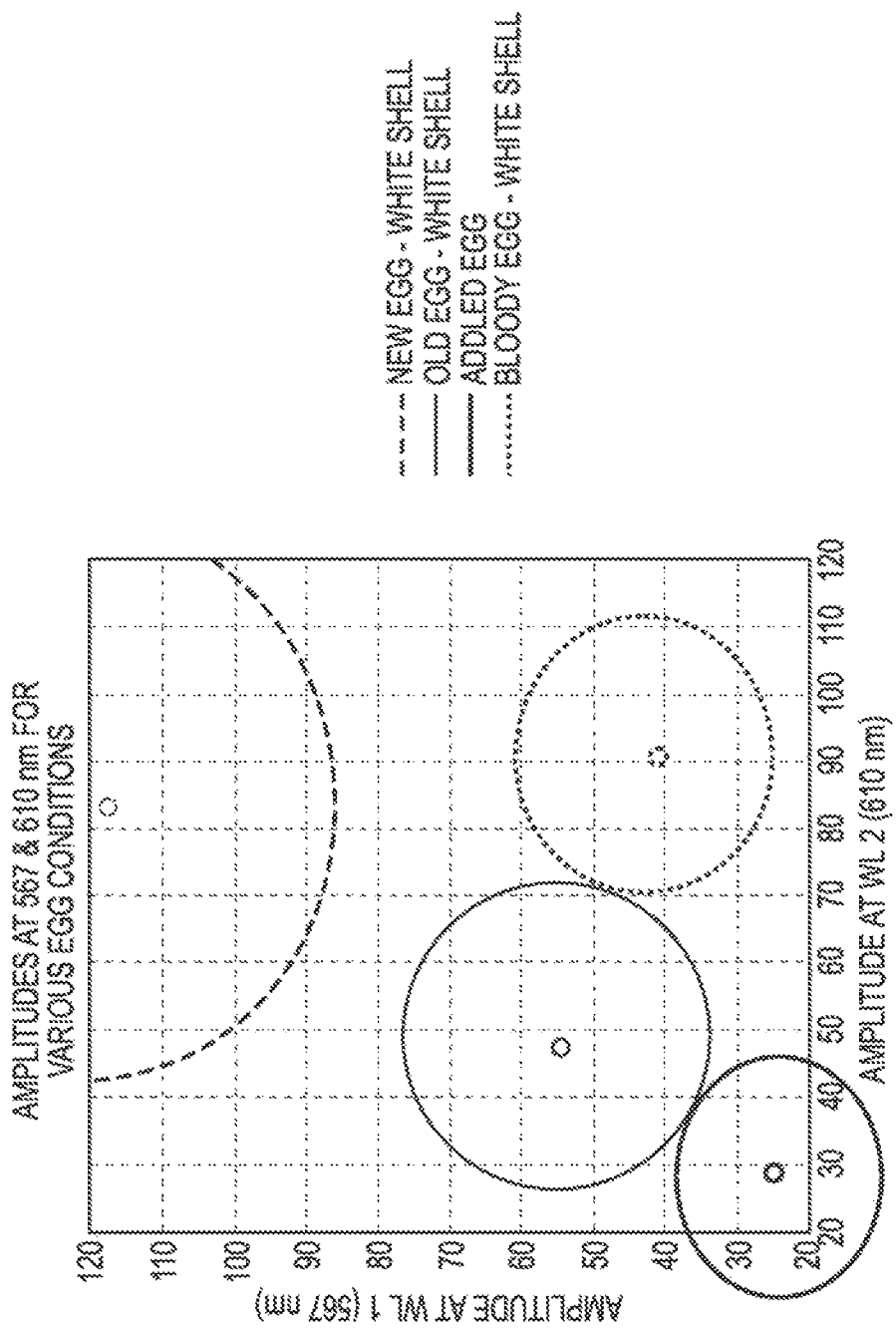

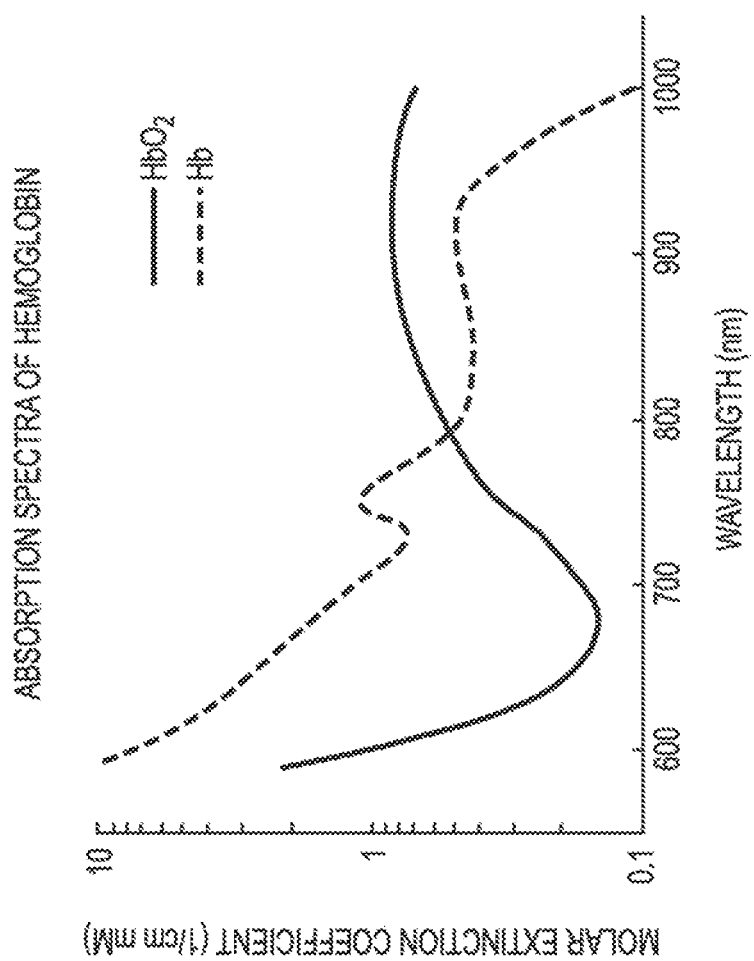

SPECTRAL IMAGING SYSTEM FOR REMOTE AND NONINVASIVE DETECTION OF TARGET SUBSTANCES USING SPECTRAL FILTER ARRAYS AND IMAGE CAPTURE ARRAYS

PRIORITY

This application is a divisional of U.S. patent application Ser. No. 16/847,997, filed Apr. 14, 2020, which is a continuation of U.S. patent application Ser. No. 16/291,458, filed Mar. 4, 2019, now U.S. Pat. No. 10,656,015, which is a continuation of U.S. patent application Ser. No. 15/379,059, filed Dec. 14, 2016, now U.S. Pat. No. 10,222,260, which is a divisional of U.S. patent application Ser. No. 14/742,074, filed Jun. 17, 2015, now U.S. Pat. No. 9,551,616, which claims priority under 35 U.S.C. § 119(e) from United States Provisional patent application having Ser. No. 62/014,004, filed on Jun. 18, 2014, by Gary L. McQuilkin and Gregory L. Engelke, and titled SPECTRAL IMAGING SYSTEM FOR REMOTE AND NONINVASIVE DETECTION OF TARGET SUBSTANCES USING SPECTRAL FILTER ARRAYS AND IMAGE CAPTURE ARRAYS, wherein the entireties of which are respectively incorporated herein by reference for all purposes.

FIELD OF THE INVENTION

This invention relates to using spectral imaging analysis to noninvasively and remotely detect the presence, location, and/or quantity of a target substance in a scene. More specifically, this invention relates to using spectral imaging analysis to noninvasively and remotely detect the presence, location, and/or quantity of a chosen target substance via a spectral imaging system comprising a spectral filter array and an image capture array.

BACKGROUND OF THE INVENTION

Spectral imaging is a branch of spectroscopy and of photography in which at least some spectral information is collected from an image plane (e.g., two-dimensional image) for a scene of interest. An image capture device may be aimed at a scene in order to capture image information for that scene. A variety of spectral imaging methodologies are known. Examples include hyperspectral imaging, multispectral imaging (a type of hyperspectral imaging), full spectral imaging, imaging spectroscopy, chemical imaging, and the like. Historically, hyperspectral imaging and multi-spectral image analysis have been associated with satellite, airborne, or large scale operations using large, expensive camera systems that are not well-suited for handheld operation or routine business and consumer applications.

Spectral imaging generally involves capturing spectral information from one or more portions of the electromagnetic spectrum. Although spectral information for any wavelengths in the electromagnetic spectrum may be used, often spectroscopy uses spectral information for wavelengths in the range from about 100 nm to about 14,000 nm. For reference, it is often convenient to divide the span of the electromagnetic spectrum into the following bands: ultraviolet (UV) band from 100 nm to 400 nm; visible (VIS) band from 400 to 700 nm; near infrared (NIR) band from 700 to 1500 nm; short-wave infrared (SWIR) band from 1500 to 3000 nm; mid-wave infrared (MWIR) band from 3000 to 5000 nm; and long-wave infrared (LWIR) band from 5000 to 14000 nm. The ultraviolet band includes the following sub-bands: far ultraviolet (FUV) band from 122 to 200 nm; middle ultraviolet (MUV) band from 200 to 300 nm; and near ultraviolet (NUV) band from 300 to 400 nm. The ultraviolet band also is divided into the following sub-bands: ultraviolet C (UVC) band from 100 to 280 nm; ultraviolet B (UVB) band from 280 to 315 nm; and ultraviolet A (UVA) band from 315 to 400 nm.

Spectral information captured for a scene may be represented as an image cube, which is a type of data cube. A data cube generally is a three dimensional array of data values. In spectroscopy, one kind of data cube results when a spectrally-resolved image is represented as a three dimensional volume in which the captured image is represented in a two dimensional image while spectral information associated with individual pixels, or groups of pixels, is incorporated into at least a third dimension of the data cube.

Conventional hyperspectral imaging is a powerful but expensive analysis technology for remotely determining the chemical composition of a surface. For example, hyperspectral imaging typically generates a data cube with two spatial dimensions and one spectral dimension. The two spatial dimensions correspond to the spatial data that might be represented in a common digital photograph. However, each spatial pixel in a hyperspectral data cube also is associated with an electromagnetic spectral array spanning wavelengths that often extend well beyond the visible spectrum to higher and/or lower wavelengths.

A conventional hyperspectral imaging system scans a scene to capture image information. Line scanning often is used. For example, an illustrative, conventional hyperspectral system has a linear array of 256 imaging elements. This linear array is scanned across the target surface in a line-scan or "push-broom" format. In this manner the linear array can generate a three-dimensional data cube with two spatial dimensions and one spectral dimension. A typical data cube may have dimensions of 256×256 spatial dimensions by 320 spectral bins. Spatial lines or "frames" are acquired sequentially at a frame rate of 100 to 400 frames per second. This line scan modality, acquires complete image information over a second or longer. This makes it difficult to acquire high resolution images for moving subjects.

Although conventional hyperspectral imaging provides powerful analysis capabilities, additional significant limitations exist for any widespread application of this technology as conventionally practiced. Foremost is a high price of $100,000 to $200,000 per system. The linear detection array imposes a scanning modality requiring a precision fixture with a uniform scanning speed between target surface and linear detection array. The line scan requirement also eliminates the possibility of acquiring a truly simultaneous image since the detector scans across the target surface in sequential lines. Undue movement of the target with regard to the scanning coordinates tends to result in an unrecognizable spatial shape in the resulting image. With movement, the resulting spectral information for a given pixel also may be distorted. The scanning requirement, alignment complexity and necessary fixturing often results in a stationary system that is not easily transported. With a high price tag and precise scanning restrictions, conventional hyperspectral imaging systems are limited primarily to inspection systems in large scale operations for high-volume production lines such as food processing, garbage sorting, or mineral analysis. Conventional hyperspectral imaging is not well suited for mobile applications, high-resolution systems, multi-line operation, bench-scale laboratory analysis, small business or consumer uses.

Multispectral imaging also offers the potential for remotely determining the chemical composition of a surface. Similar to a hyperspectral image, a multispectral image contains data with both spatial and spectral dimensions. Unlike the hyperspectral image, which contains a full spectrum for each spatial pixel, a multispectral image contains a fixed number of broad spectral bands for each spatial pixel. Conventional multispectral imaging systems typically are designed for one or more specific initial uses but are difficult to reconfigure for other uses.

The digital photography and digital camera industries have developed high quality, low cost sensors that capture images for portions of the electromagnetic spectrum that fall within the visible spectrum, namely, 400 nm to 700 nm. Both professional and consumer markets show strong interest in and benefit from these technologies. Digital cameras and phones typically use either charge-coupled device (CCD) or CMOS image sensors to capture images. These CCD and CMOS sensors can be obtained with a wide range of resolutions, e.g., from 540×720 (0.39 MP), to 5184×3456 (18 MP) in a number of digital, single lens reflex cameras (Canon EOS 60D Digital SLR Camera with lens kit, 5184× 3456 pixels, 18 MP, $1300) and lower cost, compact cameras (Canon PowerShot, A1300, 16 MP, $119). Recent advances have led to miniaturization such that these cameras are routinely integrated into small form factors as thin as 7.6 mm (0.3 in.), including the lens. An example of a product that integrates such a miniaturized form factor are the iPhone 5 smartphone available from Apple Inc. as well as other smartphones. In addition to smartphone technology, there are a number of other mobile and economical computing technologies such as tablet, mini-tablet, laptop, and desktop technologies. Each of these alternative technologies shares many capabilities with those of smartphones.

Smartphone and other mobile computing technologies such as touch sensitive tablets have significant computing and connection power as well as the inclusion of digital cameras. While early models had only limited photography capability, the latest smartphones, such as the iPhone 5 and Samsung Galaxy S III have dual digital cameras (front and back facing) with resolutions of 8 MP/1.2 MP and 8 MP/1.9 MP, respectively. In addition to camera features, these smartphones have the capability for GPS location and navigation, as well as sensing vertical and horizontal phone orientation. Communication capabilities include Bluetooth and Wi-Fi standards.

Researchers at the University of Illinois are developing a smartphone-based spectrometer. See Liz Ahlberg, Cradle Turns Smartphone into Handheld Biosensor, University of Illinois, News Bureau, Public Affairs, May 23, 2013. A custom cradle holds the smartphone in fixed alignment with optical components that include a photonic crystal biosensor. This device detects shifts in the resonant wavelength of the biosensor on the order of 5 nm. The target must be dissolved in a small vial of liquid and placed on a microscope slide. The slide is in turn placed in a slot on the cradle attached to the smartphone. While this device contains a smartphone display for observing a single, resonant wavelength of a biosensor for the given target substance on the microscope slide, it does not provide mobile, high-resolution, chemical imaging capability. This device cannot be used for high volume or instantaneous analysis of a target substance due to the time required to dissolve the target substance in water, place the solution on a microscope slide and await a 30 second analysis which consults a web-based, data base.

Heinold, U.S. Pat. Application No. 20140022381, describes a spectral imaging apparatus that includes a multi-camera system having multiple camera elements, a set of filter elements attached to the camera elements and a light-sensor array, and a second set of filter elements attached to the light-sensor array elements.

Even with the multitude of technologies described above, there presently exists no mobile, economical and convenient method or apparatus to rapidly, remotely and accurately detect, locate or quantify information of interest, such as the presence or amount of a target substance at particular location(s) in a scene. Therefore, there is a strong need for a spectral imaging system that has detection capabilities associated with hyperspectral and multispectral imaging systems but is economical, able to acquire high-resolution data rapidly from moving targets, is mobile, and is suitable for agricultural, medical, veterinary, sanitation, industrial, business, and consumer uses. Also, there is a strong need for spectral imaging systems whose detection capabilities can be easily changed on demand to be able to detect information for a wide range of desired applications.

SUMMARY OF THE INVENTION

The present invention relates to spectral imaging systems and methods for noninvasively and remotely detecting the presence, location, and/or quantity of a target substance in a scene of interest. More specifically, this invention relates to using spectral imaging analysis noninvasively and remotely detect the presence, location, and/or quantity of a target substance via a spectral imaging system comprising a spectral filter array and an image capture array. The spectral filter array comprises a plurality of filter elements each of which selectively passes a selected bandwidth portion of the electromagnetic spectrum (e.g., one or more specific wavelengths or relatively narrow range of wavelengths) that help to characterize the spectrum of the chosen target substance. By appropriate selection of the filter elements used in the spectral filter array, the spectral filter array can be customized to include a sufficient number of filter elements that allow that filter array to be used to detect a target substance of interest. In this way, each spectral filter array is associated with at least one specific target substance and may be used to detect the associated target substance.

The system desirably includes a plurality of interchangeable spectral filter arrays (also referred to herein as a library of spectral filter arrays) that interchangeably align with the image capture array on demand. This allows the system to be used to detect a wide range of target substances. For example, the system is easily configured to detect a particular target substance by selecting and deploying the corresponding spectral filter array in optical alignment with the image capture array. The system can be easily re-configured to detect another target substance by selecting and deploying an alternative filter array and implementing an analysis algorithm for such other target substance or by using a different analysis algorithm associated with the other target substance but using the same filter array. The spectral filter array may be changed via a simple coupling mechanism such as by placing a different spectral filter array module in an attachment holder, such as a filter slot, clip, spring-loaded attachment, screws, bolts, snap fit engagement, adhesive, or hook and loop fastener (e.g., the Velcro brand hook and loop fastener), compartment, retainer, spring, combinations of these, and the like. The spectral filter array may also be changed electronically such as by electronic control of an electronically tunable filter array. In the sense of being quickly configured for multiple detection applications, the present invention provides a "universal" detection system.

The image capture array comprises a plurality of image capturing elements that are aligned with corresponding filter element(s) in a manner effective to capture a plurality of spectrally filtered images for the scene of interest. The captured image information is analyzed to determine information indicative of the presence, location, and/or quantity of the target substance in the scene. For example, individual pixels, or groups of pixels, may be analyzed to determine if the pixel(s) are associated with spectral responses matching the spectrum of the target substance. If a match is found, the target substance is detected and the location of the pixel(s) in the image information helps to precisely locate the target substance in the scene that was imaged. In embodiments that use high resolution image capturing elements, this allows even minute traces of a target substance to be detected if even only a single pixel in an image corresponds to the target substance. Analysis of the image information can also be used, as described further below, to quantify the amount of target substance that is detected. The presence, location, and/or quantity of the target substance are computed and may be displayed on an output image. For example, the system can output an image in which image pixels associated with the target substance are highlighted in some way to show location and even quantity of the target substance. This invention provides a significant improvement over conventional hyperspectral imaging and multi-spectral imaging systems in the areas of cost, resolution, simultaneous image acquisition, imaging of moving targets, miniaturization, mobile operation, and ease of adapting to different applications.

The present invention further provides methods to select the filter elements that are used in a particular spectral filter array to allow the system to detect a target substance of interest. According to one approach for selecting such filter elements, the spectrum of the target substance across a broad range of wavelengths is provided. In many embodiments, the spectrum is obtained over a relatively broad wavelength range spanning at least 14,000 nm, or even at least 5000 nm, or even at least 2000 nm, or even at least 1000 nm, or even at least 500 nm, or even at least 300 nm, or even at least 200 nm, or even at least 100 nm. For example, in many modes of practice, such as when obtaining a spectrum over a typical range of CCD sensor sensitivity, a span of 1000 nm from about 200 nm to about 1200 nm would be suitable. To help distinguish the target substance from other materials that might be in the same scene, spectra for one or more background substances over a similar wavelength range also may be provided. The spectra of the chosen target substance and anticipated background substance(s) are analyzed and specific bandwidth portions (e.g., within the wavelength range of 200 nm to 1200 nm, wavelength bandwidths of up to 30 nm, or up to 20 nm, or up to 15 nm, or up to 10 nm, or up to 5 nm, or even specific wavelengths in many modes of practice) of the target spectrum are selected that identify and differentiate the target substance spectrum from the spectra of anticipated background substances. Filter elements that selectively and respectively pass the selected bandwidth portions are provided and incorporated into a spectral filter array.

As used herein, bandwidth for a filter refers to the difference between the upper and lower cutoff wavelengths. A cutoff wavelength is a boundary in a filter's spectral response at which the transmission amplitude is reduced to 50% of the maximum transmission amplitude. In actual practice, a filter element used in the practice of the present invention may not attenuate all wavelengths outside the desired wavelength range completely. Instead, there often is a region just outside the intended passband where wavelengths are attenuated, but not fully rejected. For purposes of the present invention, and recognizing such attenuation, the bandwidth of an optical filter element is deemed to be the full width half maximum (FWHM) bandwidth. Thus, the bandwidth specification may be designated as the width of the spectral curve for wavelengths that are half of the maximum transmission amplitude. An example of specifications for a spectral filter element may be as follows: center wavelength, 980+/−2.00 nm; minimum transmission, ≥85%; full-width, half maximum (FWHM), 10.00+/−2.00 nm; blocking wavelength range, 200-1200 nm; optical density, 4.

The image capture array is aligned with the spectral filter array so that image capture elements of the image capture array can capture a filtered image through at least one corresponding filter element. Depending upon the target substance at issue, all or only a portion of the filter elements in a spectral filter array may be used to capture filtered images. After an array of filtered images is captured, the filtered images are typically stored in electronic memory and processed, either in real-time or otherwise. The system uses the captured, filtered image information to determine which portion(s) of the captured image information (if any) have spectral characteristics that match the spectral characteristics of the target substance.

The analysis of captured image information may be performed by any suitable computing device. Suitable mobile platforms include a smartphone, laptop computer, tablet computer, mini-tablet computer, desktop computer, head-mounted computer, mobile computer, or cloud-based computer.

In illustrative modes of practice, program instructions analyze the spectrally filtered images via a target substance algorithm that is capable of analyzing image information to determine which portion(s), if any, of the image information have spectral characteristics that match the spectral characteristics of the target substance. For example, individual pixels, or groups of pixels, of captured image information can be analyzed to assess if the pixel(s) display spectral characteristics of the target substance. This analysis may be used to determine the presence, location, and/or quantity of the chosen target substance within the scene of interest. Additionally, the program instructions may generate an output image that displays the presence, location and/or quantity of the target substance with respect to objects within the scene.

The spectral imaging system of the present invention may be calibrated in a variety of ways to enhance the performance of image capture and analysis. For example, in many modes of practice, calibration occurs by using either an in-frame reference or an accumulation of nominal component specifications. The in-frame reference, having known spectral characteristics on its surface, may be used to account for variations in illumination, filter element attenuation, and image sensor sensitivity together as an assembled system for each corresponding elemental pair within the spectral filter array and image capture array. Additionally, a cumulative calibration for each corresponding elemental pair may be computed by using the manufacturing specification for each component. The required accuracy and system cost goals for a given detection of a chosen target substance will determine which calibration method is advantageous, with a quantity indicator likely to require the more accurate, in-frame reference calibration. Because the system uses an array of image capture elements to capture an array of filtered images, the individual images may be aligned (also referred to in the imaging industry as image registration) so that features in one image are accurately matched and aligned with the same features in the other image(s).

In many modes of practice, the present invention satisfies the desire to be able to detect a target substance remotely and noninvasively. This avoids the time and cost associated with a laboratory analysis. Using an appropriate spectral filter array according to the principles of the present invention, the system may be used to detect a target substance that is solid, liquid, gas or plasma. The target substance may be a pure chemical substance, a compound of chemical substances, or a mixture of chemical substances. The present invention can be used to detect any kind of target substance that has spectral characteristics that can be viewed within at least portions of the fields of view of the image capture array. Individual pixels, or groups of pixels, of captured image information can be analyzed to assess if the pixel(s) display spectral characteristics of the target substance. In embodiments that use high resolution image capturing elements, this allows even minute traces of a target substance to be detected if even only a single pixel in an image corresponds to the target substance. Moreover, by recognizing which pixel(s) of captured image information correspond to a target substance, the precise location(s) of a target substance in an image can be located and identified.

In representative modes of practice, this invention provides the capability to provide a powerful chemical imaging tool, sensitive to a wide range of spectral wavelengths, in a package that can be small, light-weight, battery-powered, and mobile. The output can be provided rapidly without the delay associated with a laboratory analysis. The spatial location of a target substance within the field of view may be shown on a representative image of the scene. For example, the system can output an image in which image pixels associated with the target substance are highlighted in some way to show location and even quantity of the target substance. If desired, spectral imaging systems also may be provided as a stationary system with a cost that is a small fraction of the cost commonly associated with systems providing similar chemical imaging capability. For instance, one representative implementation of this invention is a handheld, multi-camera adapter integrated with a smartphone as illustrated in FIGS. 5A, 5B and 5C. The multi-camera adapter includes multiple camera elements as an image capture array, and these camera elements are optically aligned with the filtering elements of the spectral filter array incorporated into an interchangeable, spectral filter card. The system may be re-configured to be sensitive to a different target substance by choosing a different spectral filter card from a library of spectral filter cards, each card including an array of filter elements that is designed to capture identifying spectral information for specific target substance(s). In some modes of practice, the system may be re-configured to be sensitive to a different target substance by selecting a different target substance algorithm to be used with the same filter card. The system would be capable of detecting a vast number of different target substances determined by the filter card selection. The cost of the multi-camera adapter and spectral filter card is a small fraction of the cost necessary to achieve similar chemical imaging capability with conventional hyperspectral imaging or other remote sensing systems. Additionally, the image resolution available with the present invention may be 10 to 100 times greater than the more expensive, conventional systems.

Advantageously, the present invention provides a high level of performance using a wide variety of low-cost, digital camera sensors. Many of these sensors have a native spectral sensitivity of 300 nm to 1100 nm (prior to the addition of filters intended to reduce sensitivity to only the visible spectrum, 400-700 nm) and may be used to provide a high-resolution, low-cost, multi-camera array capable of acquiring multiple images simultaneously. This permits simultaneous image acquisition, which is very desirable for high-speed operation or moving subjects. Such simultaneous image acquisition for moving subjects is not possible with conventional hyperspectral imaging systems that rely on line-scan image acquisition. In addition, the optically aligned filter elements, which determine the wavelength sensitivity for each camera element, may be mounted on a filter card, permitting different target substances to be selected simply by changing filter cards and internal software algorithms.

In a typical mode of practice, spectral information is acquired for a desired target substance. This spectral information includes spectral information for the target substance and may, if desired, include spectral information for anticipated background substances. The spectral information preferably is analyzed to determine a finite number of specific wavelengths that in combination uniquely distinguish the spectral characteristics of the target substance from the spectra of one or more background substances. These predetermined wavelengths and knowledge of the spectral characteristics of the target substance and optionally the background are then used to create a spectral imaging system. The system includes an image capture array (also referred to herein as a multi-camera array) having a plurality of image capturing elements (which in some embodiments are individual camera elements) that are sensitive to a unique bandwidth portion of the electromagnetic spectrum. The unique spectral sensitivity for each image capturing element of the multi-camera array is achieved via a filter array including a plurality of filter elements. Each filter element in the filter array is optically aligned with a corresponding image capturing element of the multi-camera array. The filter characteristics of each filter element are selected so that each filter selectively passes a bandwidth portion that encompasses a pre-determined wavelength. Preferably, the spectral filter array is interchangeable with other filter arrays so that the detection capabilities of the system can be quickly configured to detect any of a wide variety of target substances by selection of an appropriate spectral filter array.

In some embodiments the spectral filter array may even be more permanently secured to the imaging system if desired. This may be desired where the system will be used in rugged or dangerous environments to help prevent a spectral filter array from being easily dislodged. Examples of more secure fastening include screws, bolts, welds, fusing, adhesives, rivets, clamps, wiring, combinations of these, and the like.

For example, in one illustrative mode of practice, six wavelengths are selected that allow a target substance to be selected from a background substance. An image capture array with six or more image capturing elements may be fitted with a filter array including six filtering elements. Each of the filtering elements is designed to selectively pass a bandwidth portion encompassing one of the selected wavelengths or wavelength bandwidths. The imaging system then may capture six corresponding, filtered images. In many modes of practice, captured images, each representing a unique portion of the spectrum, optionally are processed to spatially align pixels in each image such that they represent the same spatial point on the image plane within the field of view of the system.

Capturing simultaneous images allows analysis of moving objects without suffering from motion distortion and blurring. Additionally, the simultaneous acquisition of images from multiple camera elements enables a solid-state system that does not require a mechanically rotating filter wheel as is often used with systems that implement sequential filtering methods. Additionally, the simultaneous acquisition of images permits high quality output images when processing is conducted at a video rate or higher.

The system then analyzes the captured image information to determine which pixels of the image information display spectral characteristics of the target substance. For instance, the spectrally-distinct, spatially aligned images may be processed to mathematically derive information regarding the presence and quantity of the target substance at points on the target surface or within the target volume, optionally accounting for variations in spectral illumination, camera element sensitivity and filter element attenuation. An output, such as an output image, may be computed that overlays information about the position and quantity of the target substance on a spatial orientation image (SOI) representing the spatial position of objects within the field of view. This output image may provide information about only the presence of the target substance at each spatial position, or it may also provide information about the quantity of the target substance at each spatial position.

In other modes of practice, the arrays may include more or less than six elements. In some modes of practice, an array may include a greater number of array elements, e.g., ten or more elements, but only some of these elements, e.g., 3 or 4 elements, are needed and used to capture information for a particular target substance. In other modes of practice, a single bandwidth portion may be suitable to encompass two or more pre-determined wavelengths. In such embodiments, a single image capturing element and a single corresponding filtering element may be used to capture spectral information for such two or more pre-determined wavelengths.

In one aspect the present invention is connected to any number of outside devices via connectivity standards common to smartphones and computing devices. Examples of such connectivity interfaces include, but are not limited to, Wi-Fi, Bluetooth, and/or numerous additional wireless standards. In another embodiment, the wireless link may be replaced by any suitable wired link. Examples of wired links are selected from at least one of USB, Firewire, Ethernet, custom, proprietary, or a multitude of other wired standards.

In one aspect, the present invention relates to a spectral imaging system for remotely and noninvasively detecting the presence and location of one or more target substances in a scene, said system comprising:
a) an image capture array comprising a plurality of image capturing elements;
b) a plurality of spectral filter arrays, wherein:
 (i) each spectral filter array is pre-associated with at least one corresponding target substance;
 (ii) each spectral filter array includes a plurality of spectral filtering elements, wherein each spectral filtering element of said plurality of spectral filtering elements selectively passes a pre-selected bandwidth portion of the electromagnetic spectrum that is pre-associated with a spectral characteristic of the corresponding target substance;
 (iii) each of the plurality of spectral filter arrays is selectable and positionable on demand to be aligned with the image capture array such that each of at least two or more of the image capturing elements is optically aligned with at least one corresponding spectral filtering element in a manner effective to capture spectrally filtered image information comprising image pixels; and
c) program instructions that use the spectrally filtered image information to determine if image pixels are associated with spectral responses matching the target substance and to determine and output information indicative of the presence and location of the at least one associated target substance in the scene.

In another aspect, the present invention relates to a method of remotely and noninvasively detecting at least one target substance in a scene, comprising the steps of:
a) providing an image capture array comprising a plurality of image capturing elements;
b) providing a spectral filter array, wherein:
 (i) the spectral filter array is associated with at least one corresponding target sub stance;
 (ii) the spectral filter array includes a plurality of spectral filtering elements, wherein at least two spectral filtering elements of said plurality each selectively passes a pre-selected bandwidth portion of the electromagnetic spectrum that is pre-associated with a spectral characteristic of the corresponding target substance;
 (iii) the spectral filter array is aligned with the image capture array such that each of at least two or more of the image capturing elements is optically aligned with at least one corresponding spectral filtering element in a manner effective to capture spectrally filtered image information comprising image pixels;
c) aiming the image capturing elements of the image capture array at the scene;
d) using the image capture array and the spectral filter array to capture a plurality of filtered images of the scene; and
e) using information comprising the filtered, captured images to determine if image pixels are associated with spectral responses matching the target substance and to determine and output information indicative of the presence and location of the at least one associated target substance in the scene.

In another aspect, the present invention relates to a method of providing a spectral imaging system, comprising the steps of:
a) providing spectral information for a target substance;
b) using the spectral information to associate at least first and second bandwidth portions of the electromagnetic spectrum with spectral characteristics of the target sub stance;
c) providing a spectral filter array comprising a plurality of spectral filtering elements, wherein a first spectral filtering element selectively passes the first bandwidth portion of the electromagnetic spectrum and a second spectral filtering element selectively passes a second bandwidth portion of the electromagnetic spectrum; and
d) causing an image capture array comprising a plurality of image capturing elements to be aligned with the spectral filter array in a manner effective to capture first and second, filtered images through the first and second spectral filtering elements in a manner such that image pixels of the filtered images that match the spectral characteristics of the target substance indicate the presence and location of the target substance in a scene.

In another aspect, the present invention relates to a method of processing image information, comprising the steps of:
  a) capturing a first filtered, spectral image of at least a portion of a scene wherein the first filtered spectral image is obtained using a first spectral filter element that selectively transmits a first bandwidth portion of the electromagnetic spectrum within which a target substance has a first pre-determined spectral response;
  b) simultaneously capturing a second filtered, spectral image of at least a portion of the scene, wherein the second filtered spectral image is obtained using a second spectral filter element that selectively transmits a second bandwidth portion of the electromagnetic spectrum within which the target substance has a second pre-determined spectral response, and wherein the first and second filtered, spectral images comprise image pixels; and
  c) using information comprising the first and second filtered, spectral images to determine if image pixels are associated with spectral responses matching the target substance and to determine and output information indicative of the presence and location of the at least one associated target substance in the scene.

In another aspect, the present invention relates to a spectral imaging system, comprising:
  a) an image capture array comprising a plurality of image capturing elements;
  b) a plurality of spectral filter arrays, wherein:
    (i) each spectral filter array is pre-associated with at least one corresponding target substance; and
    (ii) each spectral filter array includes a plurality of spectral filtering elements, wherein each spectral filtering element of said plurality of spectral filtering elements selectively passes a pre-selected bandwidth portion of the electromagnetic spectrum that is pre-associated with a spectral characteristic of the corresponding target substance;
    (iii) each of the plurality of spectral filter arrays is selectable and positionable on demand to be aligned with the image capture array such that each of at least two or more of the image capturing elements is optically aligned with at least one corresponding spectral filtering element in a manner effective to capture spectrally filtered image information in a manner such that image pixels of the filtered images that match the spectral characteristics of the target substance indicate the presence and location of the target substance in a scene.

In another aspect, the present invention relates to a method of providing an imaging system for detecting a target substance in a scene, comprising the steps of:
  a) providing spectral information for a target substance;
  b) using the spectral information to associate a plurality of specific bandwidth portions of the electromagnetic spectrum with spectral characteristics of the target substance;
  c) using the selected bandwidth portions to provide a spectral imaging system comprising:
    i) an image capture array comprising at least two image capturing elements, each image capturing element capable of independently capturing an image of the scene;
    ii) a filter array comprising a plurality of filter elements, each sensitive to a pre-determined specific bandwidth portion, and wherein the filter elements are each aligned with a corresponding camera element of the image capture array in a manner such that the image capture array captures image information for a plurality of independent spectrally filtered images;
    iii) program instructions that use the captured image information to identify at least one spatial location of the target substance in the scene.

In another aspect, the present invention relates to an imaging system for detecting a target substance within a scene, comprising:
  a) an image capture array with at least two image capturing elements, each image capturing element capable of independently capturing an image of a scene;
  b) a spectral filter array comprising a plurality of spectral filtering elements that are each optically aligned with a corresponding image capturing element of the image capture array in a manner such that the image capturing array captures a plurality of independently, selectively, and spectrally filtered images, and wherein each spectral filtering element of said plurality of spectral filtering elements selectively passes a pre-selected bandwidth portion of the electromagnetic spectrum that is pre-associated with a spectral characteristic of the corresponding target substance;
  c) program instructions that use a plurality of captured images to provide an output indicative of the presence and location of the target substance is in the scene.

In another aspect, the present invention relates to a method of detecting a target substance in a scene, comprising the steps of:
  a) using an image capture array and a spectral filter array, to simultaneously capture a plurality of spectrally filtered images of the scene, wherein the spectral filter array is sensitive to at least two bandwidth portions of the electromagnetic spectrum which provide spectral information effective to identify the target substance; and
  b) using the spectrally filtered images to generate an output indicative of the presence and the one or more locations of the target substance in the scene.

In another aspect, the present invention relates to a spectral filter system, comprising a plurality spectral filter arrays, wherein each spectral filter array comprises a plurality of spectral filtering elements, and wherein each spectral filter array is pre-associated with at least one target substance, and wherein each spectral filtering element of said plurality of spectral filtering elements selectively passes a pre-selected bandwidth portion of the electromagnetic spectrum that is pre-associated with a spectral characteristic of the corresponding target substance.

BRIEF DESCRIPTION OF THE DRAWINGS

FIG. 3A shows the differentiation of spectra for water and background substances using two wavelengths.

FIG. 6 shows an alternative embodiment of a spectral imaging system of the present invention.

FIG. 7 shows an alternative embodiment of a spectral imaging system of the present invention.

FIG. 8 shows an alternative embodiment of a spectral imaging system of the present invention.

FIG. 9 shows an alternative embodiment of a spectral imaging system of the present invention.

FIG. 10 shows an embodiment of the present invention using two different spectral imaging systems to observe both sides of a target.

FIG. 21 shows a mirror configuration of the present invention using a two-element, image capture array.

FIG. 22A shows a mirror configuration of the present invention using a three element image capture array.

FIG. 22B shows a mirror configuration of the present invention using a four element image capture array.

FIG. 25A is a 'full spectrum' image taken with the narrower visible spectrum filter removed (typically included with digital cameras).

FIG. 25B is an NIR detection image, sensitive to a narrow bandwidth centered on the absorption peak of water at 980 nm.

FIG. 25C is a spectral reference image centered in an area of the spectrum which exhibits little spectral absorption for water at 766 nm.

FIG. 29C shows a plot of amplitudes of the spectral information in FIG. 29A for different egg conditions.

FIG. 31 shows absorption spectra of oxyhemoglobin and deoxyhemoglobin.

DETAILED DESCRIPTION OF PRESENTLY PREFERRED EMBODIMENTS

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

Figure 1:
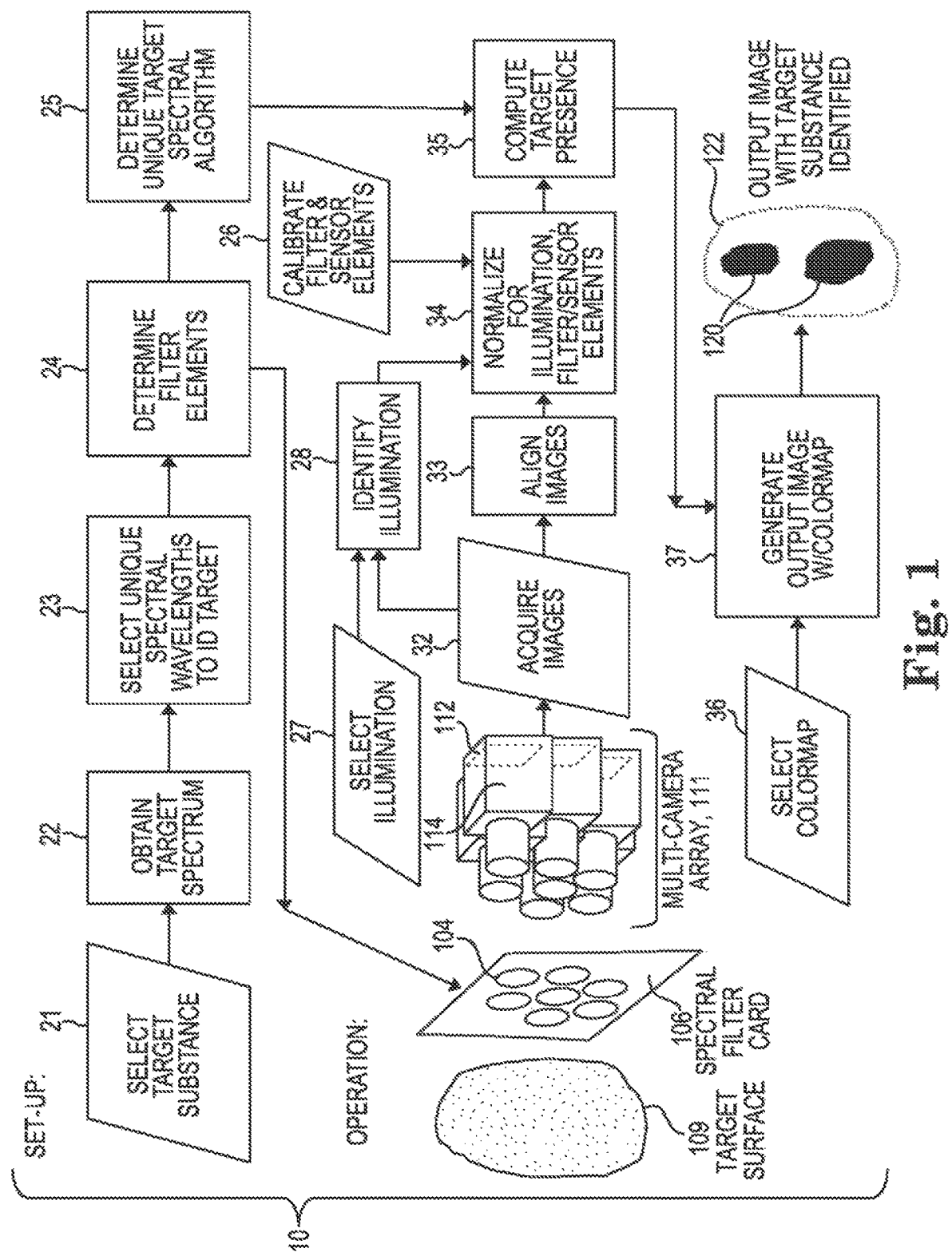
FIG. 1 schematically shows a block diagram of set-up and operation of a system for detecting a target substance using principles of the present invention.

An illustrative embodiment of a spectral imaging system 10 of the present invention is schematically shown in FIG. 1. Spectral imaging system 10 includes set-up features and operational features. The set-up features, customized for each chosen target substance, involve obtaining the electromagnetic spectrum for the chosen target substance, selecting unique spectral wavelength(s) to identify the substance, selecting corresponding filter elements, and designing a unique target algorithm to reliably identify the target. The operational features include both equipment and processing components. The operational equipment comprises a spectral filter card 106 and a multi-camera array 111 having image capturing elements (such as CCD sensors). The operational processing components may include the following processing steps: image acquisition, image alignment, image normalization for variations in spectral parameters, computation of the presence and/or quantity of the target substance, generation of a colormap, and generation and display of an output image showing the result of the detection procedure. The operational blocks are processing operations that may be executed at or near real time as the multi-camera system is operating and the target substance is within the field of view. While an advantage of the present invention is real-time operation, the present invention also encompasses modes of operation in non-real time mode, batch mode, or other slow or delayed processing operation. Additionally, the simultaneous image acquisition permits freeze-motion images to be easily obtained for moving targets.

Illustrative set-up features of system 10 includes blocks (or steps) 21, 22, 23, 24, and 25. The blocks 21, 22, 23, 24, and 25 are largely design steps that help to establish the custom characteristics of the system 10 for each desired application for which system 10 is used to detect one or more target substances. FIG. 1 shows how system 10 is set up for detection of a particular target substance. In practice, this design phase may be carried out as many times as desired to allow system 10 to be used to detect a library of different target substances in multiple settings.

Set-up begins in block 21 with a selection of a target substance whose detection is desired. An advantage of the present invention is that system 10 can be used to detect any target substance that has an identifying electromagnetic spectrum in a reflection and/or transmission mode when exposed to natural or artificial electromagnetic radiation. For example, some target substances exhibit characteristic spectral information at a plurality of different wavelengths when exposed to sunlight. Some substances exhibit characteristic spectral information at one or more particular wavelengths when irradiated with artificially created infrared (IR), ultraviolet (UV), laser, or other irradiation.

Accordingly, it can be appreciated that the present invention can be used to detect a wide variety of different target substances. Illustrative examples include but are not limited to any of the following target substances, either singly or in combination: water in any form (ice, steam, vapor, liquid, etc.), urine, arterial blood, venous blood, oxyhemoglobin, deoxyhemoglobin, fruits, vegetables, rodent trails, pests, fingerprints, bodily fluids, gunshot residue, security features of a treasury bill or government check, sunscreen, ultraviolet security spray, ultraviolet paint, automotive fluids (i.e., oil, antifreeze, Freon), medical marker dyes, plants, minerals such as sand, quartz, alumina, other metal oxides, nitrides, carbides, ultraviolet brighteners that are present in hunters' clothing, ultraviolet dyes, tumors, skin cancer, wounds, chemical substances, solids, liquids (water, aqueous solutions, organic solvents, etc.), pastes, processed foods, meats, body fluids containing a target substance that varies with a mammalian estrus cycle, grains, plant protein products, animal protein products, animal complete feeds, mycotoxins, people, and animals.

In block 22, spectral information of the target substance is obtained for the target over desired range(s) of the electromagnetic spectrum. As one example, an illustrative range of the electromagnetic spectrum can span all or a portion of the wavelengths at least from about 200 nm to about 14,000 nm. For reference, it is often convenient to divide this span of the electromagnetic spectrum into the following bands, UV, UVA, UVB, UBC, NUV, MUV, FUV, VIS, NIR, SWIR, MWIR, and LWIR.

The application of the present invention includes, but is not limited to, all or portions of one or more of these bands. In many embodiments, the spectral information is obtained for at least a portion of the visible band as well as at least a portion of at least one of the ultraviolet band and/or the NIR band.

The spectral information for a target substance can be obtained using any suitable spectroscopy technique(s) that provide spectral information for a plurality of wavelengths. In some embodiments, it is suitable to obtain a uniformly-sampled spectrum of the target over the desired range of the electromagnetic spectrum via hyperspectral imaging, multispectral imaging, or the like. Alternative systems to obtain a useful target spectrum may include spectroscopy systems such as those commercially available from FOSS. Absorption and/or reflectance spectra may be used for the present invention.

In some modes of practice, spectral information of all or a portion of the anticipated background over a similar wavelength range and resolution is also obtained. This allows the spectral information of the target substance and its anticipated background to be compared. From this comparison, spectral characteristics of the target substance, preferably at two or more wavelengths, can be identified that allow the spectral response of the target substance to be uniquely identified relative to its background. For example, a particular crop of interest when healthy may have leaves that provide spectral peaks at 425 nm and 705 nm wherein the magnitude ratio of the 425 nm peak to the 705 nm peak is on the order of about 2:1. However, when the crop is excessively dehydrated, the ratio may drop to about 0.5:1. In such an instance, the healthy plant may be the target substance (or vice versa), while the dehydrated plant is a background element (or vice versa). The ratio of the spectral responses of the crop at 425 nm and 705 nm can be used to detect healthy plants relative to dehydrated plants.

In block 23, the spectral information of the target substance and optionally the background (if desired) is then analyzed via suitable signal processing and spectral analysis techniques to uniquely identify one or more, specific spectral wavelengths that may be used to distinguish the target substance from the background. In preferred modes of practice, at least two specific spectral wavelengths are identified. More preferably, 2 to 500, even more preferably 2 to 100, even more preferably 2 to 50, and even more preferably 2 to 15 specific wavelengths are identified.

Figure 2B:
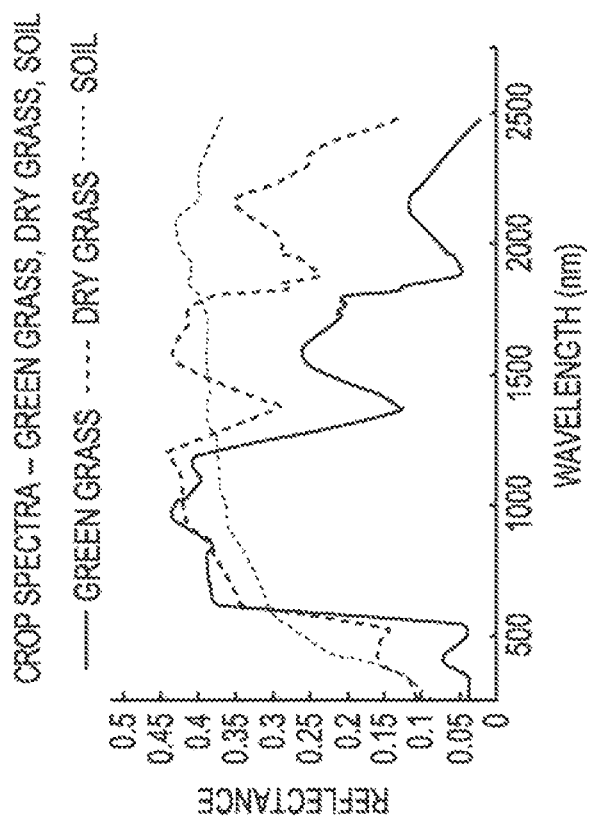
FIG. 2B shows sample reflectance spectral information for green grass, dry grass and soil.
Figure 2A:
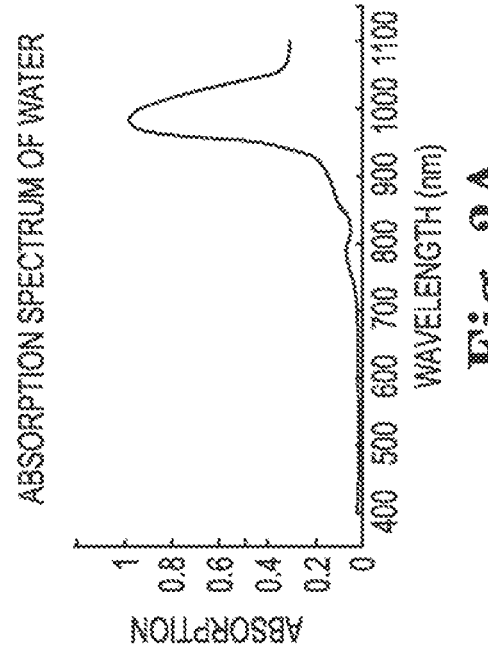
FIG. 2A shows absorption spectral information for water between 400 nm and 1100 nm.
Figure 2E:
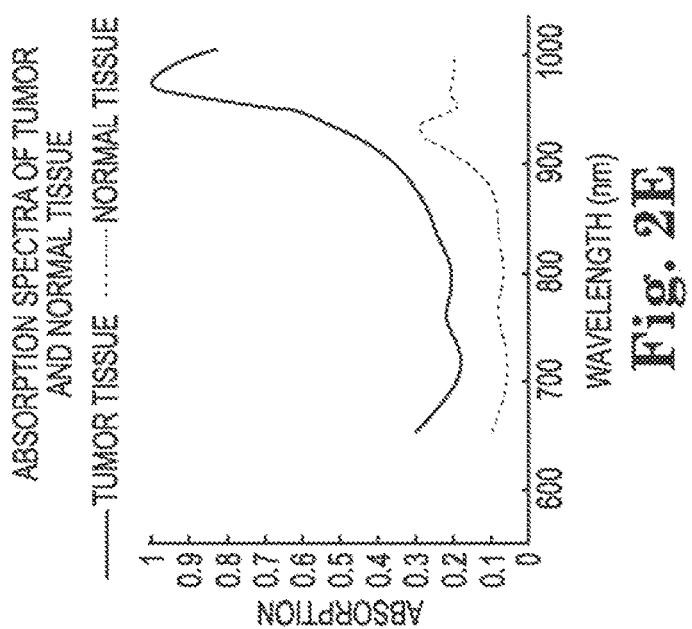
FIG. 2E shows absorption spectral information for normal tissue and a tumor between 650 nm and 1050 nm.
Figure 2D:
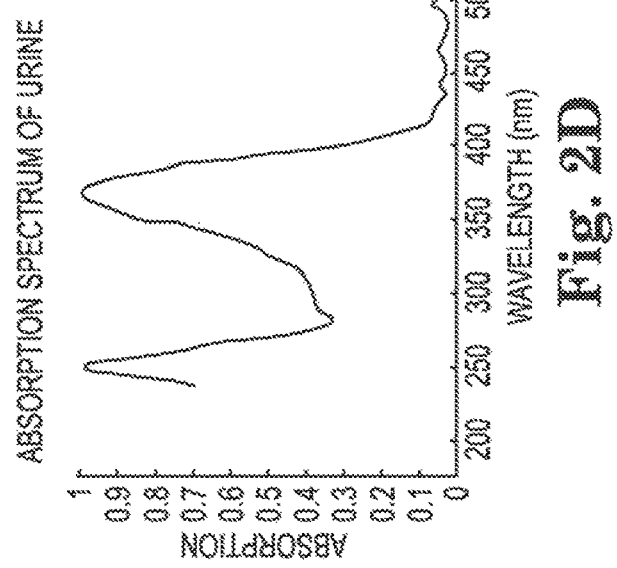
FIG. 2D shows absorption spectral information of urine between 200 nm and 550 nm.
Figure 2C:
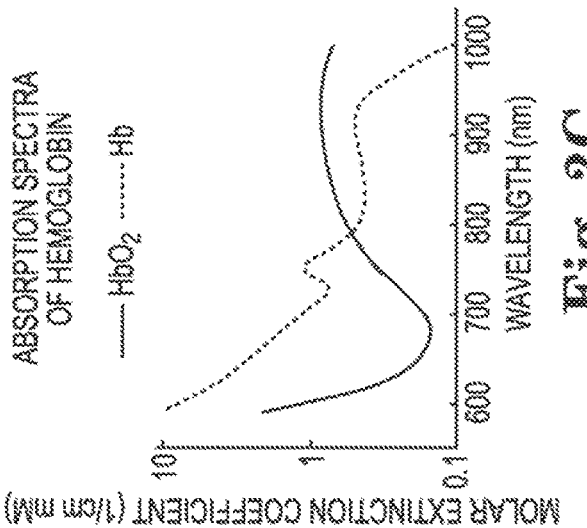
FIG. 2C shows absorption spectral information of hemoglobin and oxyhemoglobin between 600 nm and 1000 nm.

The concept of using spectral information of a target substance to identify the wavelengths in block 23 is based on the fact that the spectra of common substances such as those shown in FIGS. 2A through 2E vary greatly when compared to the spectra of other substances. FIG. 2A shows the absorption spectra of water. FIG. 2B shows that the spectra among green grass, dry grass, and soil can be distinguished from each other. FIG. 2C shows that the spectra of hemoglobin and oxyhemoglobin are distinguishable. FIG. 2E shows that spectra of tumors and normal tissue can be distinguished. In the practice of the present invention, these differences are used to facilitate detection. Conventional hyperspectral imaging systems provide a full spectrum to distinguish one target substance from another. While effective, much of the hyperspectral information is superfluous.

In more preferred modes of practice, the present invention reduces the amount of spectral information used to make an identification to only selected portions of the spectrum that allow the desired detection to be practiced. By reducing the acquisition and analysis data to pre-selected, finite spectral features, great improvements in device size, cost, power consumption, resolution, and processing speed are realized. Specifically, in preferred modes of practice the present invention reduces the spectral information needed to identify or measure the target substance to that obtained for a discrete number of carefully selected wavelengths or relatively narrow wavelength bands. The selected spectral information is incorporated into the system design by assigning each element of a spectral bandpass filter array to have a center frequency corresponding to one of the selected wavelengths or bands. This spectral filter array, implementing the selected wavelength sensitivities, is combined with a multi-camera array such that each spectral filter element is optically aligned with a corresponding element of the multi-camera array. Thus, image acquisition from the multi-camera array results in an array of images with each representing a different wavelength sensitivity. These are useful to uniquely identify or quantify the desired target substance within the field of view of the multi-camera array.

FIG. 3A illustrates a preferred approach used by the present invention to identify pre-selected spectral wavelengths used to distinguish among the selected target substance(s) and/or background substance(s). FIG. 3A shows how water can be distinguished from background spectral information using two spectral components. When the target spectrum and background spectrum are simple and substantially different as in FIG. 3A the spectra need to be examined at only two wavelengths to easily detect the target substance. In this example, absorption spectral information can be examined at 760 nm and 980 nm. If the ratio (980 nm/760 nm) or other suitable characteristic(s) of the spectral response at these two wavelengths is greater than a threshold, then the pixel of captured image information providing that response corresponds to water. If the ratio is too low, no water is detected with respect to that pixel.

Figure 3B:
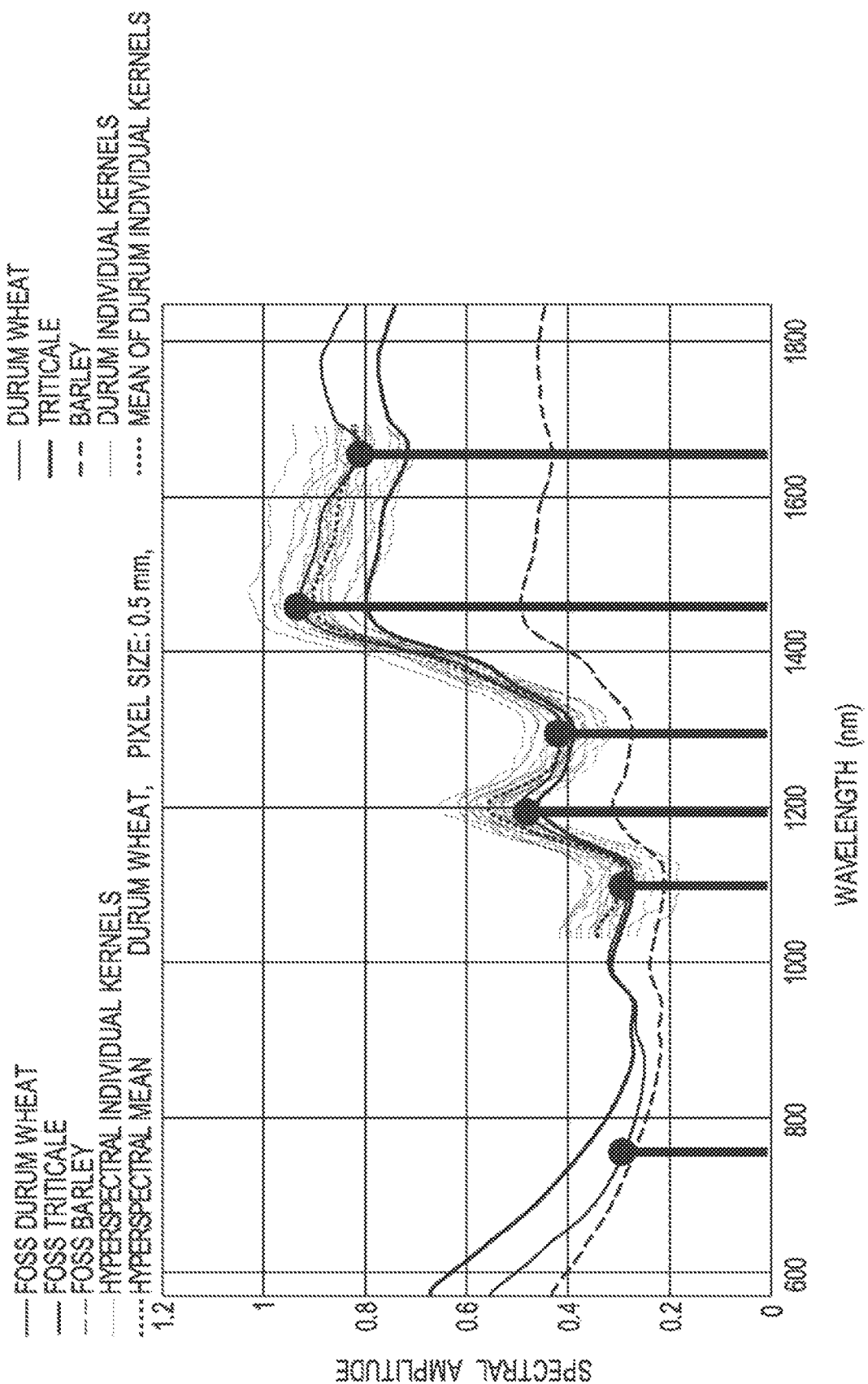
FIG. 3B shows the differentiation of spectra for durum wheat, barley and triticale using six wavelengths.

If the spectra are more complex and/or more similar, as in FIG. 3B, it is more desirable to select a greater number of wavelengths to accurately detect the target substance. In this example, spectral information for durum wheat, triticale, barley, and individual durum kernels is shown. By obtaining spectral information at approximately 760 nm, 1100 nm, 1200 nm, 1300 nm, 1460 nm and 1650 nm any one of the substances can be identified from the captured image information. Spectral properties of the captured wavelengths, e.g., ratios, sums, differences, averages, etc., can be analyzed to determine which of the materials is associated with a pixel in the image information. The assessment is accurate and fast. If computing power is fast enough, the results of an analysis can be computed and displayed in a fraction of a second even for images captured at higher resolutions, e.g., 16 megapixels or higher resolution.

In both cases shown in FIGS. 3A and 3B the target substance can be accurately detected with a relatively low number of spectral samples (2 and 6 wavelengths, respectively, in these examples). The present invention may also be practiced by gathering spectral information at a greater number of wavelengths, but when the use of a more limited number is effective, it is much more efficient and economical.

The advance selection of the filter wavelengths in the present invention, as part of the set-up, provides a significant advantage over conventional hyperspectral imaging systems in terms of the volume of data that must be acquired, stored and processed. A comparable multi-camera system with 3 wavelengths requires less than 1% of the data volume and processing effort when compared to a hyperspectral system having 310 spectral bins. While maintaining the same diagnostic power for many substances, this data savings, inherent in the present invention, can be used to greatly increase the spatial resolution for a multi-camera system having the same memory space and processor capability over its conventional hyperspectral counterpart.

Referring again to FIG. 1, in block 24, the selected wavelengths from block (23) are used to determine the corresponding filter elements (104) to be implemented as a filter array in the filter card (106). Generally, it is desirable to have at least one corresponding filter element 104 for each selected wavelength identified in block 23 that will be used by system 10 to detect the target substance. For purposes of illustration, filter card 106 as shown includes an array of seven different filter elements 104. This indicates that for this particular target substance, spectral information at seven specific, different wavelengths are to be used to detect the target substance. For other target substances, the same, a greater or lesser number of filter elements 104 may be included in the array to accomplish detection.

Each filter element 104 is used to selectively filter the spectral information captured by the system 10 so that system 10 can assess which portions (if any) of the captured image information generate spectral responses at the selected wavelengths to confirm that the captured image portion, e.g., each pixel of the image in some embodiments where pixel by pixel analysis is desired, indicates the presence of the target substance at that location of the captured image. Desirably, each filter element 104 has a bandwidth effective to capture one of the corresponding, selected wavelengths to be used to detect the target substance. More desirably, the center wavelength of each filter element 104 is a selected wavelength determined in block 23.

The bandwidth of each filter element 104 may be selected to allow system 10 to reliably detect and assess whether the specific spectral response of the target substance at that wavelength is detected. Selecting an appropriate bandwidth for each filter associated with each selected wavelength may be optimized as a tradeoff between a narrow bandwidth, which is more selective, and a wider bandwidth, which passes a greater quantity of light making the system 10 perform better under low light conditions. Balancing such concerns, a suitable bandwidth for each filter element 104 is typically up to 30 nm, or up to 20 nm, or up to 15 nm, or up to 10 nm, or up to 5 nm, or even specific wavelengths in many modes of practice. Often, a suitable bandwidth for each filter element 104 is typically in the range from 10 nm to 30 nm.

For example, consider an exemplary spectral filter element with a bandwidth of 10 nm wherein the bandwidth is centered at 500 nm. Such a filter element will selectively pass electromagnetic energy with a wavelength of 495 nm to 505 nm while substantially blocking electromagnetic energy having wavelengths above and below this range. Such a filter element is well suited for capturing image information at wavelengths of 495 to 505 nm so that system 10 can determine if any portions of the captured image information indicate the spectral response of the target substance in this wavelength range. By using an array of filter elements 104, system 10 selectively captures meaningful spectral information at several wavelengths to enhance the ability of system 10 to accurately detect the target substance.

As another specific example, if the selected application involves detecting the presence of water in a clear container via transmission of light through the water within the container, the filter elements might include the following:

a) a 980 nm bandpass filter with a 20 nm bandwidth, sensitive to the water absorption band near 980 nm, making the water appear very dark;

b) a 766 nm bandpass filter with a 20 nm bandwidth, sensitive to a wavelength that does not include a water absorption band, making it an excellent reference image that can see through water; and c) a visible spectrum bandpass filter which provides a spatial orientation image such that the output of the processing of images from a) and b) camera elements above may be oriented on an image representing the field of view as seen by a human observer.

Block 25 involves the generation of one or more algorithms that can be used to assess the captured, selectively filtered image information to determine if the spectral information indicates the presence of the target substance from the anticipated background using the selected wavelengths identified in block 23 and the corresponding filter elements 104 that selectively capture image information at those wavelengths. Examples of algorithm methods include, but are not limited to, eigenvector, basis function, least squares, principle component analysis, ratios, differences, matched filter, neural networks, cross-correlation, multivariate analysis, and numerous classification methods.

The set-up of system 10 contemplated by blocks 21 to 25 can be carried out for any number of additional target substances such that the resulting system 10 includes a plurality of spectral filter arrays and algorithms to detect a substantial library of target substances. System 10 can be configured to detect any target substance in the library simply by choosing the appropriate filter array and then using a suitable system interface to select the corresponding detection algorithm(s). The interface may be automated such that selection of a particular filter array causes system 10 automatically to implement the corresponding algorithmic analysis. Alternatively, in instances in which a filter array might be useful for detecting more than one target substance, the user could manually select the appropriate algorithm(s). In some embodiments, the orientation of a filter array when integrated into system 10 may cause system 10 to automatically (or manually) select algorithm(s) corresponding to that orientation of the spectral filter array.

It is anticipated that blocks 21 to 25 may be part of a manufacturing process for system 10 where an inventory of one or more spectral filter cards and corresponding algorithm(s) for a variety of different detection applications is designed and sold as a package. It is also anticipated that a family of filter elements may be incorporated into a single filter card that contains subsets of filter elements, wherein each subset of the filter elements in the cards works to identify a different target substance.

For example, consider a filter card including four filter elements 1 through 4, respectively. Application A may use filter elements 1, 2, and 3 on a four-element filter card, while application B may use filter elements 1, 3 and 4, while application C may use filter elements 2, 3, and 4. The combination of filter elements for multiple applications is dependent upon the spectral characteristics of the selected target substances and the desire of the user to have several applications readily available without the need to change filter cards.

Another example of using a single filter card for multiple detection purposes might involve a three-application filter card designed for forensic investigators at a crime scene. Such a combination might include the selection of spectral filter elements to detect blood splatter, filter elements to detect semen, and filter elements to detect fluorescent dyes used to highlight fingerprints. Quite easily, the present invention could provide three different filter cards (and their associated software algorithms) for blood, semen, and fingerprints, respectively, wherein each filter card includes an array of filter elements suitable for selectively capturing the previously identified set of selected wavelengths that allow the corresponding target substance of interest to be identified from filtered image information. However, if the selected wavelengths to be analyzed overlap or are substantially the same (where uniqueness of each target substance is determined using an algorithm that analyzes characteristics of the spectral responses as a whole, such as ratios of responses at different wavelengths, etc.), the present invention contemplates that a single filter array on a single filter card could be used to capture filtered image information for all three substances. This is efficient if the plurality of target substances at issue have one or more filter wavelengths in common. In this case, additional functions can be provided with only an incremental increase in the number of filter and camera elements. Under the described combination scenario, different filter elements within the same filter card could be used by the same or different algorithms to detect and locate each of the different target substances in the captured image information. The output could comprise a color-coded image that displays the locations of blood, semen and fingerprints at the crime scene or any combination thereof.

A consumer example of a combination of applications on a single filter card for a busy parent of small children with a kitten as a pet might include a spectral filter group for detecting sunscreen (to assure complete coverage of children's skin at the beach), a filter group to detect cat urine stains (to quickly locate kitten 'accidents'), and a filter group for matching paint colors (to precisely match paint colors in the kitchen).

Figure 14:
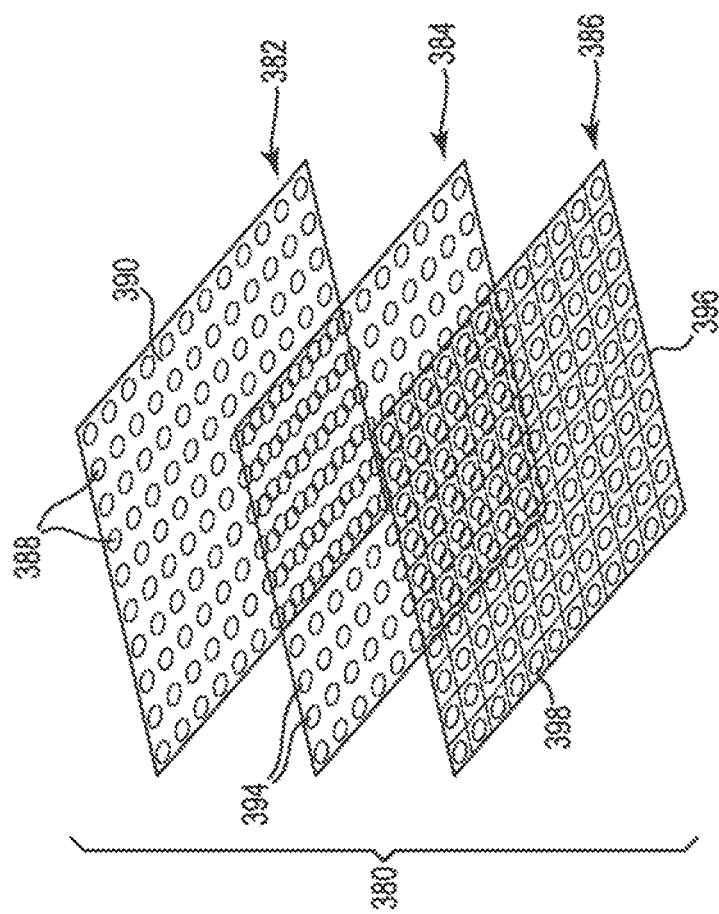
FIG. 14 shows an embodiment of a spectral imaging system of the present invention with an interchangeable filter array.

Block 26 indicates the optional step to calibrate the system for individual variations in filter element and sensor element sensitivity. This step increases the accuracy of detection and is preferred. This function can be implemented as part of either the target algorithm design during manufacture of the system or later as part of the image capturing phase of using system 10. As an example of a desirable calibration, each filter element 104 may have a specific attenuation of light at its center frequency and across its bandwidth. This attenuation may be measured during manufacture and recorded in a database for each element 104 of a filter card 106. The specific filter card calibration can be looked up in this database, over the internet or otherwise, according to a specific filter card serial number or designation. A calibration, also stored in a database during manufacture, is possible for the sensor element(s) of the image capture array 111. Image capture array 111 also is referred to herein as a "multi-camera array 111" to indicate that component 111 is capable of capturing a plurality of filtered spectral images simultaneously when the image capturing elements 112 are aligned with corresponding filter elements 104 in card 106. Hence, each image capturing element 112 captures a corresponding, filtered image whose bandwidth is spectrally limited by the filter element 104 through which the filtered image is captured. For purposes of illustration, each image capturing element 112 is associated with a single camera body 114, and these bodies 114 are stacked in an array suitable to align with the corresponding filter elements 104. In other modes of practice, multiple image capturing elements 112 may be incorporated into a common camera body. The term "multi-camera" still applies to a common body embodiment in the sense that "multi-camera" means that the system captures a plurality of images simultaneously regardless of the number of camera bodies involved. For example, FIG. 14 shows an alternative embodiment of a multi-camera array including a single camera body incorporating a plurality of image capturing elements for simultaneous image capture. As used herein, the term "multi-camera array" also is used to refer to an "image capture array". Additionally, a "spectral filter array" also may be referred to as a "multi-element spectral filter".

The camera sensor elements may be calibrated using any suitable technique. For example, a multi-wavelength calibration is suitable either via a calibrated light source that changes wavelengths, or a standard, broadband light source using a calibrated filter card with filter elements at designated wavelengths and attenuations which permit an accurate interpolation across the entire spectral region for which the sensor is used. Both the filter elements and the camera sensor elements may also be recalibrated using the real-time processing system and an automated calibration system used in the field. Such an automated calibration system desirably has the traits described above and can automatically record the resulting calibration parameters within the memory of a smartphone, or other computing device to be used during operation of the system.

Once the spectral filter elements 104 in the filter card 106 have been selected and provided, the target algorithm(s) developed and provided suitable for detecting the corresponding target substance(s) at issue, and the system calibration optionally carried out, the system 10 can rapidly capture and process filtered images simultaneously acquired from the multi-camera array 111 to provide any desired output to report the results of the detection. For example, the system can indicate whether or not the target substance was detected. The system also may provide information showing the location of the target substance in the captured image information. For example, the system may provide a color-coded output image that shows where the target substance is within the cumulative fields of view of the camera array. Since the images from the multi-camera array may be sampled simultaneously, any motion of the target has less of an impact on detection accuracy as compared to instances in which images or scans are performed only sequentially. Simultaneous image capture makes the present invention very suitable for detection in environments with moving targets.

FIG. 1 shows how system 10 is used to capture image information from a target surface 109 in Block 32 to allow system 10 to assess whether the target substance at issue is present in the target surface 109. Additionally, system 10 is used to capture the image information to allow system 10 to output the precise location(s) of the target substance, if present, in the target surface 109. The images are simultaneously acquired in step 32 from each image capturing element 112 (also referred to as a camera element herein) of the multi-camera array 112. Each image capturing element 112 is aligned with a corresponding filter element 104 so that such image capturing element 112 captures filtered images through the corresponding filter element 104. Each filtering element 104 has a bandwidth that is sensitive to a unique selected wavelength associated with the detection of the target substance. Therefore, each acquired image respectively includes information from only a unique, narrow region of the electromagnetic spectrum centered and limited by the filter element 104 through which the image was captured.

Since the components of the multi-camera array occupy slightly different spatial positions relative to the target surface 109, it may be desirable in some modes of practice to more precisely align or register the captured images in optional block 33 such that corresponding pixels in each image represent the same point on the target surface 109. Once properly aligned, the images may be further processed to detect the target substance on the target surface.

In preferred modes of practice, spatial image alignment or registration, is the process of overlaying or aligning two or more images of generally the same scene taken from different spatial viewpoints. System 10, in fact, simultaneously captures a plurality of filtered images of substantially the same scene from a plurality of viewpoints. In order to more accurately perform detection, it is desirable for the separate images to be accurately aligned with each other such that corresponding portions of the target surface can be properly identified in each of the different images. Advantageously, having at least two cameras capturing images of the scene of interest from multiple viewpoints permits the present invention to acquire stereoscopic data. These data may be used to derive three-dimensional data about the target surface using stereoscopic image processing techniques known to those skilled in the art.

There are numerous methods available to accomplish this spatial image alignment. A survey of suitable methods for spatial alignment or registration of images is described in Barbara Zitova, Jan Flusser, Image Registration Methods: a Survey, Image and Vision Computing, 21 (2003): 977-1000. The reviewed methods are area-based and/or feature based. Registration is achieved generally according to four basic steps, namely, feature detection, feature matching, mapping function design, and image transformation and resampling.

Different embodiments of the present invention may use one or more of the methods described in Zitova and Flusser, as well as other registration methods known to those skilled in the art, to spatially align or register the multiple images acquired from the multi-camera array.

Since the spectral content that is reflected from or transmitted through a target surface may vary with the illumination spectrum, it may be desirable in optional block 28 to properly identify the illumination that is present. This may be accomplished by examining the image intensities from various spectral imaging elements 112 with knowledge of their associated filter wavelengths, or it may be accomplished by energizing custom lighting with known spectral properties (i.e., LED, incandescent, sodium, neon, quartz halogen, ultraviolet, tungsten, fluorescent, compact fluorescent, infrared, near-infrared, mercury vapor, xenon, or laser sources). Once the illumination spectrum is known, the intensity of each acquired image may be normalized in optional block 34 to take the spectral features of the given illumination into account. A variation on the automated identification of the illumination source would include a user interface (i.e., software, switch or button) to manually identify the type of illumination as shown by optional block 27.

In block 35, system 10 uses the captured image information, optionally modified by processing such as alignment and normalization, to detect the presence of the target substance (if any) on the target surface 109. System 10 then generates an output that communicates the results of the evaluation. A wide variety of different outputs can be used. For example, system 10 may output information indicative of whether the target substance was detected or not. Other output information may be in the form of an image of the field of view of the system 10 that shows the locations, if any, where the target substance is located. This is particularly useful in applications where the target substance or its characteristics are not easily visible to the naked eye. Other output may communicate other qualitative or quantitative information concerning the target substance.

Figure 19B:
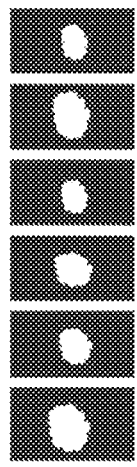
FIG. 19B shows how the present invention can output an image showing the presence and location of contaminants on the stainless steel surface of FIG. 19A.
Figure 20:
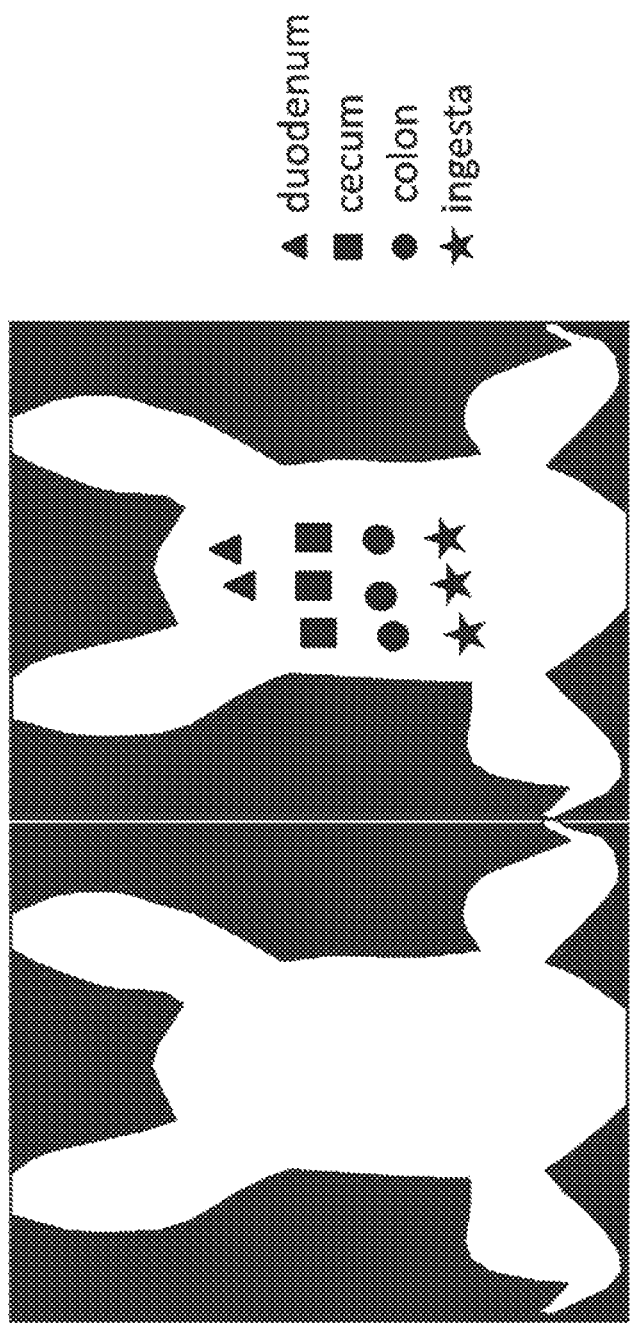
FIG. 20 schematically shows output images of poultry carcasses in which principles of the present invention are used to detect contaminants on the carcasses.
Figure 32A:
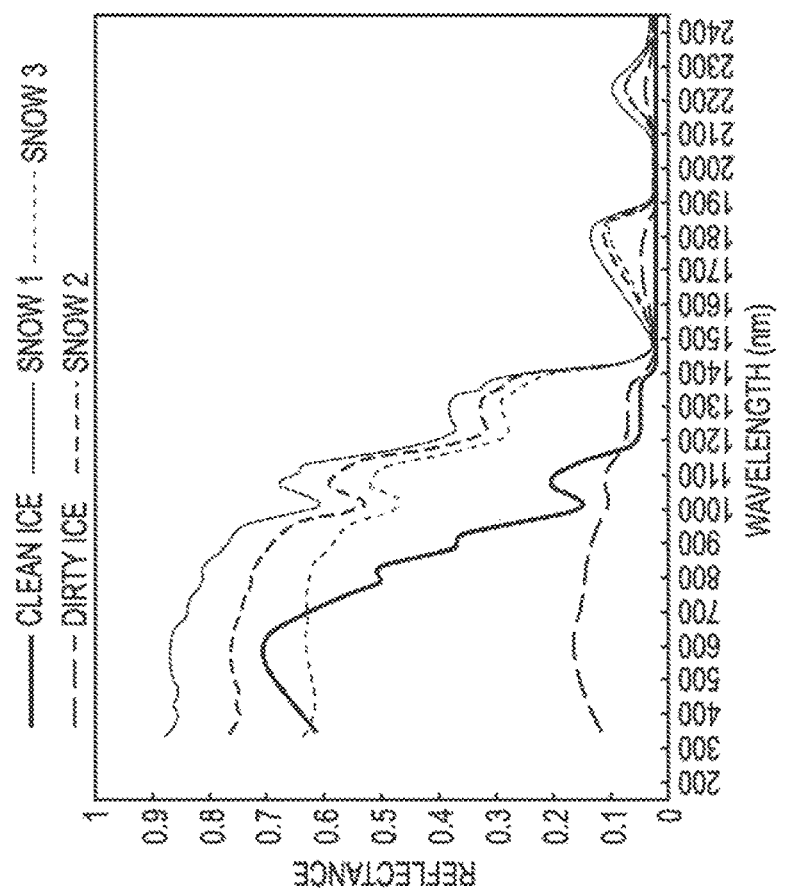
FIG. 32A shows spectral information for road conditions.
Figure 32B:
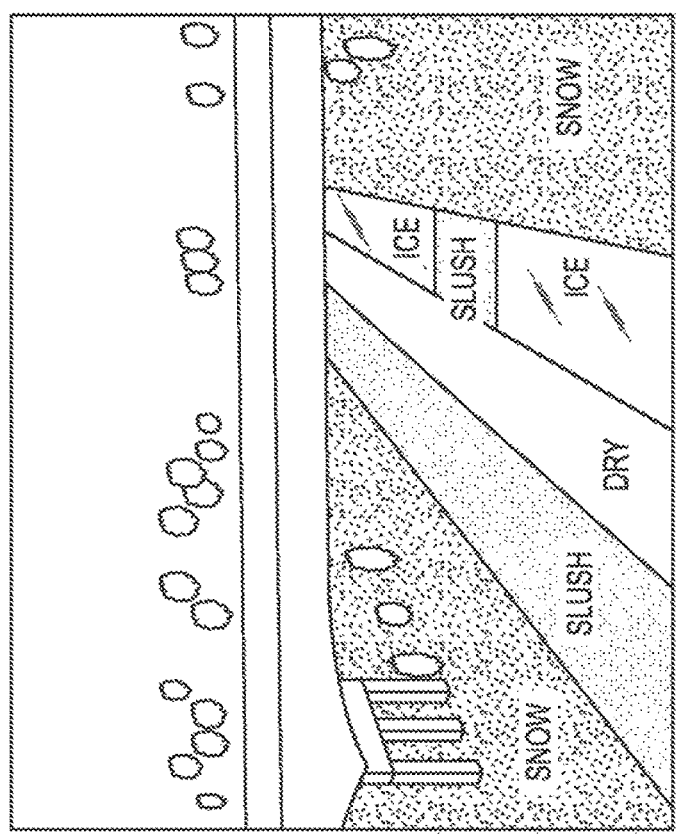
FIG. 32B shows how spectral information can be used to detect and locate road conditions in a road scene as viewed from the perspective of a traffic camera.
Figure 33:
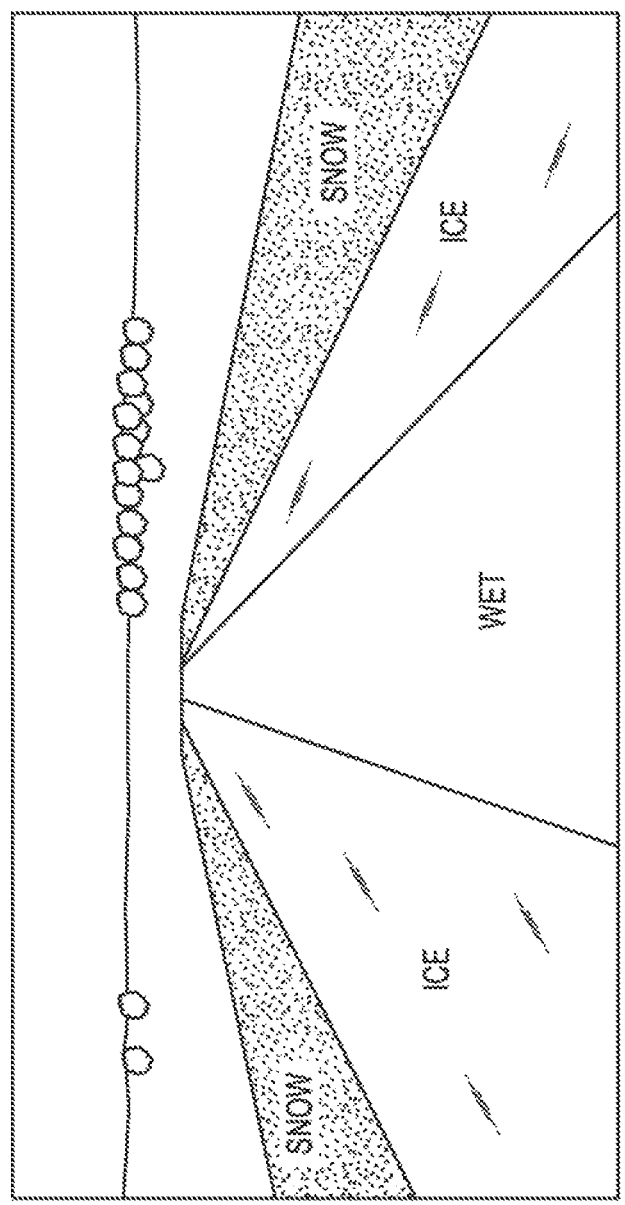
FIG. 33 shows how spectral information can be used to detect and locate road conditions in a road scene as viewed from the perspective of a vehicle.

Examples of color-coded output images are discussed below and shown in FIG. 4 (schematic), FIG. 5B, FIG. 17 (arteries and veins), FIG. 19B (organic contaminants on stainless steel), FIG. 20 (poultry carcass), FIG. 25E (water), FIG. 27 (water), FIG. 28C (grains), FIG. 32B (road conditions), FIG. 33 (car vision), FIGS. 34B to 34D (liquids), FIG. 35B (sunscreen), FIG. 36B (sunscreen), and FIG. 37 (sunscreen).

In another type of "presence" output, a displayed image may be formulated to show the spatial presence of the target substance as a solid color easily discerned from other parts of the display. The displayed image may be processed to indicate the presence of the target substance above a threshold level as a binary image mask. This mask is then used to force the associated pixels in the spatial orientation image to a fixed level. The colormap may be programmed to provide a grayscale color for all levels except the fixed level corresponding to the pixels related to the target substance.

In another type of "quantity" output, a displayed image may be formulated to show a quantitative amount of the target substance at locations within the target field of view. A binary target mask may first be derived as described for the 'presence' above. However, a further processing step introduces varying values in the 'presence' locations that represents the concentration or quantity of the target substance. The colormap is then derived to transform the variations in quantity into variations in color or color intensity. In some modes of practice, data used to generate the custom 'presence' and 'quantity' displays may be made available for analysis or export to another computing device.

FIG. 1 shows an exemplary technique for generating a "presence" output in the form of a displayed image in which locations of the target substance in the displayed image are colored substantially differently from other portions of the image. According to this technique, the acquired images can be converted in block 37 into an output image 122 of the target surface 109 showing the locations 120 of the target substance on the image 122. The matrix of pixels making up image 122 may be enhanced to more clearly show the locations of the target substance by color-coding the image. If this is desired, a suitable color map may be selected in optional block 36 and then applied in block 37 to output the color-coded image 122. As a result, the locations 120 of the target substance are shown as areas of a different color relative to the other portions of image 122. In many embodiments, the color used to represent the locations of the target substance can be much brighter than the other colors in image 122 to make it easy to see the locations 120 in image 122.

The image information can be evaluated at any desired resolution. For example, each pixel of the captured image information can be individually analyzed. This is a highly accurate way to identify not only that the target substance was detected but also to precisely indicate where the location(s) of the target substance is in the captured image information. In other modes of practice, the system 10 might analyze a plurality of pixels. This is an extremely accurate approach to detect the presence of the target substance in the image, but the location of the target substance is less precise than if each pixel is evaluated.

The present invention can acquire images and display results at extremely fast rates. For example, in some modes of practice, system 10 executes the necessary computations and processing steps to provide a displayed image as output within a time period from image capture that is less than the frame rate required for video imaging, typically 1/30 second. This allows the present invention to operate and display results at a video rate or higher. This is accomplished according to one illustrative approach by applying the algorithms of this invention to the simultaneously acquired, multi-camera images via a high-speed, image or signal processor. Since the images of this invention are all acquired simultaneously, this invention can accurately freeze motion within the field of view preserving relative positions of moving targets within the field of view, a feat impossible for competitive systems that sequentially apply filter elements in front of a single camera. This capability of the present invention provides an accurate, real-time record of a target that is moving.

A variation on the above embodiment can provide a video playback rate using a slower processing system. Since the images are acquired and saved simultaneously, a slower processing system can be used to apply the algorithms of this invention in slower than real time. While the slower processing system does not process the data fast enough to keep up with the actual event, the fully-processed, final video record can be played back at a video (or higher) rate to accurately represent the original motion of the target.

System 10 also is useful in any non-contact, application where an instantaneous chemical analysis of a remote surface is beneficial. In some embodiments, system 10 can be mounted on dynamic platforms that move in the environment. Examples include land, air, and water-based vehicles. For example, system 10 can be mounted on piloted or unmanned aircraft to capture aerial images of a region of interest. The captured images can be used on the aircraft and/or can be transmitted to a remote location, if desired.

A key feature of system 10 is a multi-camera array capable of capturing a plurality of filtered images simultaneously. System 10 can simultaneously capture all spectral components needed for detection since all the spectral imaging elements 111 are optically aligned with corresponding filter elements 104 at the same time. Images may be captured simultaneously, providing advantages for high-speed imaging and imaging of moving targets.

The present invention uses terminology to characterize the images used by system 10. A detection image (DI) is an image acquired by a spectral imaging element 112 and its corresponding filter element 104. Each corresponding spectral imaging element 112 and its corresponding filter element 104 constitute a detection pair. Each detection pair has a selected wavelength sensitivity that is strategically influenced by the presence of the target substance. The filter element 104 of such a pair is selected to provide a wavelength sensitivity for detection of a unique wavelength at which the target substance has a known spectral response as determined in block 23. In order for accurate information to be determined for the target substance, system 10 desirably includes at least one detection pair to capture at least one detection image representing a strategic wavelength useful to detect the target substance at issue.

A spectral reference image (SRI) is an image acquired by a detection pair with a selected wavelength sensitivity that is minimally influenced by the presence of the target substance. The spectral reference image is useful for evaluating illumination and establishing reference levels essential to detecting changes due to the target substance. As described further below with respect to water, such a wavelength also may be used to identify a target substance based upon the minimal spectral response at that wavelength.

A spatial orientation image (SOI) is an image that reasonably represents the spatial orientation of objects within the cumulative fields of view of the system 10 as viewed within the visible spectrum. The SOI may be acquired by an independent element of the system 10 or it may be a shared image also serving as a spectral reference or detection image.

An output image (OI) 122 is an image that provides the output of the operational processing and that shows the derived information about the target substance. In one embodiment, the output image includes a spatial orientation image, shown generally in grayscale except that the target substance information is displayed as a color-coded addition to the grayscale SOI in those places in the image where the target substance has been detected.

To summarize, system 10 may be adapted to a specific application via a set-up or design step that selects specific wavelengths that uniquely distinguish the spectrum of a target substance from the spectra of background substances. System 10 formulates a target algorithm that identifies the target substance from its spectral characteristics at a plurality of selected wavelengths. A multi-camera array is then implemented having elements that are sensitive to each of the selected wavelengths, respectively. The unique spectral sensitivity for each element of the multi-camera array is achieved via an interchangeable filter array with each filter element optically aligned with a corresponding element of the multi-camera array. Each element of the multi-filter array passes only one of the selected wavelengths. This structure converts the universal multi-camera array into a custom spectral analysis tool specifically designed to analyze the spectrum of the chosen target substance. The derived information regarding the target substance(s) has many useful applications.

Figure 4:
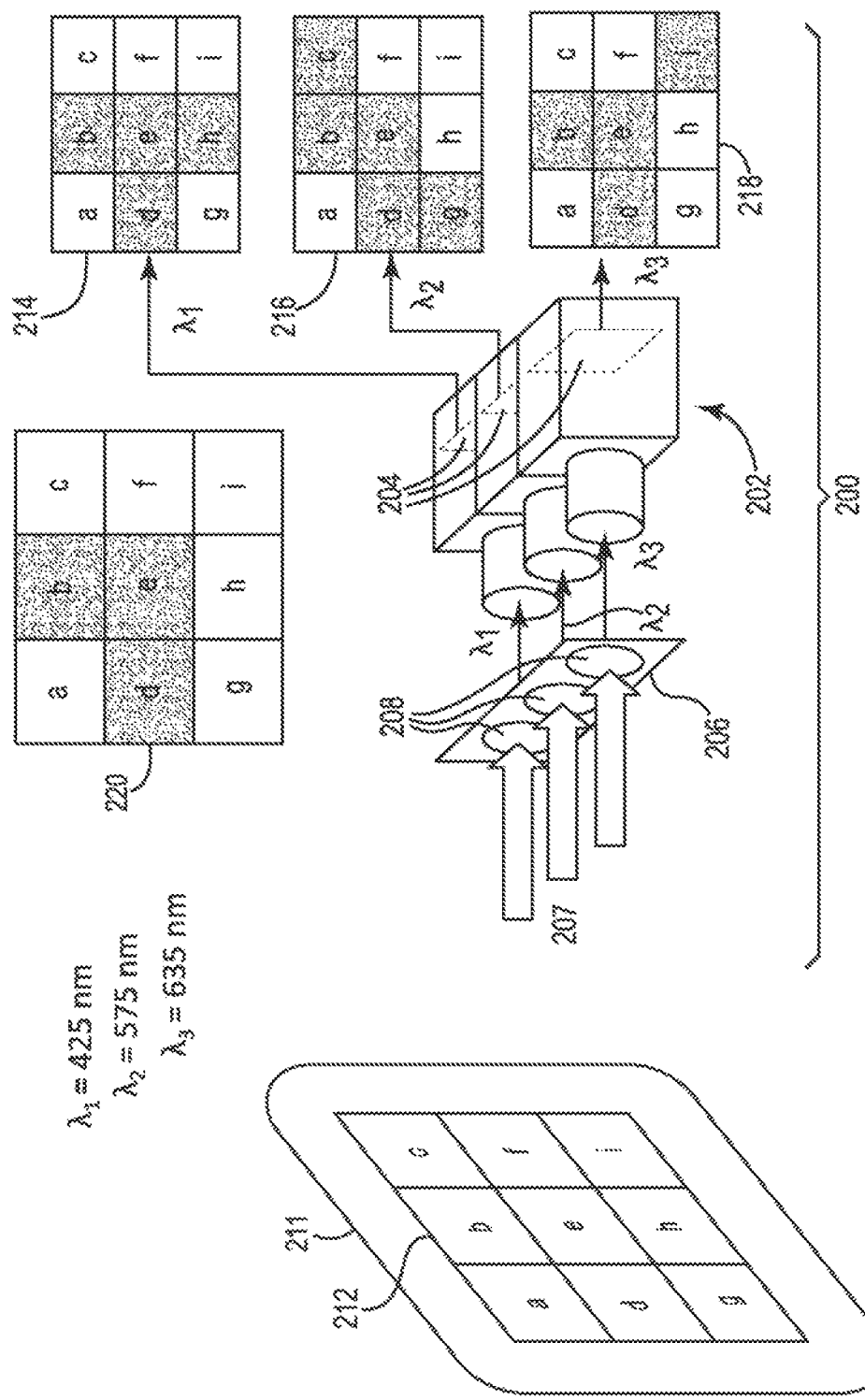
FIG. 4 shows how a spectral imaging system embodiment of the present invention captures image information at selected wavelengths and uses that captured image information to detect the presence and location of a target substance in a scene.

FIG. 4 schematically shows an alternative embodiment of a system 200 according to the present invention. System 200 includes camera body 202 incorporating a plurality of spectral imaging elements 204 that capture, encode, and store filtered images captured by system 200. In many embodiments, a spectral imaging element 204 includes a lens or a combination of lenses that is optically coupled to media capable of chemically and/or electronically storing images transmitted by the lens or lenses to the media. Exemplary electronic media include sensors such as a charge-coupled device (CCD) or CMOS image sensor. CCD and CMOS sensors are commonly used in digital photography with a blocking filter to exclude wavelengths outside of the visible spectrum. A wider bandwidth with these economical sensors may be achieved in the present invention by removing or not installing these blocking filters. Other sensors also may be used. These include those based on indium gallium arsenic (InGaAs), indium antimonide (InSb), mercury cadmium telluride (HgCdTe), lead selenide (Pb Se), microbolometers, doped silicon and a multitude of other sensor compositions to provide a desired spectral sensitivity in a selected portion of the electromagnetic spectrum. The spectral imaging elements 204 may capture images using any suitable imaging methodology such as a single shot capture system. For purposes of illustration, system 200 includes three spectral imaging elements 204.

A filter array 206 comprising filter elements 208 is incorporated into system 200. The filter array 206 includes a filter element 208 for each spectral imaging element 204. For purposes of illustration, one of the filter elements 208 has a spectral bandwidth of 420 nm to 430 nm that is well suited for detecting a spectral response at 425 nm, A second of the filter elements 208 has a bandwidth of 570 nm to 580 nm that is well suited for detecting a spectral response at 575 nm, $\lambda_2$. The third filter element 208 has an optical bandwidth of 630 nm to 640 nm that is well suited for detecting a spectral response at 635 nm, $\lambda_3$.

System 200 is being used to analyze whether a target substance having pre-determined spectral characteristics at 425 nm, 575 nm, and 630 nm might be present in a surface 212 and, if present, where the target substance is located. System 200 is aimed so that the spectral imaging elements 204 have a cumulative field of view 211 that encompasses surface 212 with multi-wavelength light 207 reflecting from the surface into spectral filter 206. For purposes of schematic illustration, system 200 has a resolution such that surface 212 constitutes a 3×3 array of pixels in the captured images. For convenience, the pixels are labeled as pixels a through i, respectively. In actual practice, captured images will include thousands and even millions of pixels.

System 200 is actuated to capture filtered images 214, 216, and 218. Captured image 214 is captured to assess the spectral response of each pixel at 425 nm, $\lambda 1$. Captured image 216 is captured to assess the spectral response of each pixel at 575 nm, $\lambda 2$. Captured image 218 is captured to assess the spectral response of each pixel at 635 nm, $\lambda 3$. Each of the captured images 214, 216, and 218 is processed to align the 3×3 array of pixels in the captured images. For illustration purposes, each pixel of each captured image having a pre-defined spectral response associated with each targeted wavelength is marked. According to the algorithm used for this detection, the target substance is deemed to be located in a particular pixel if that pixel in all the images is marked. System 200 then provides an output image 220 showing that the target substance was detected in the surface 212 at locations corresponding to pixels b, d, and e.

Figure 5B:
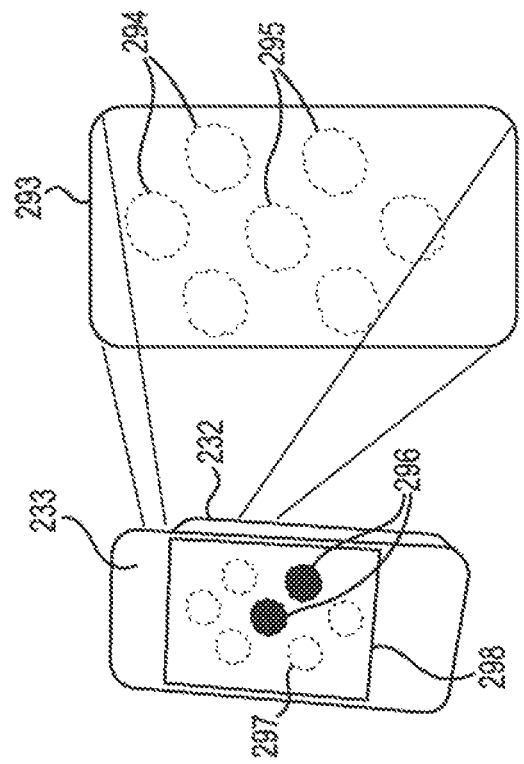
FIG. 5B shows a front perspective view of the spectral imaging system of FIG. 5A.
Figure 5C:
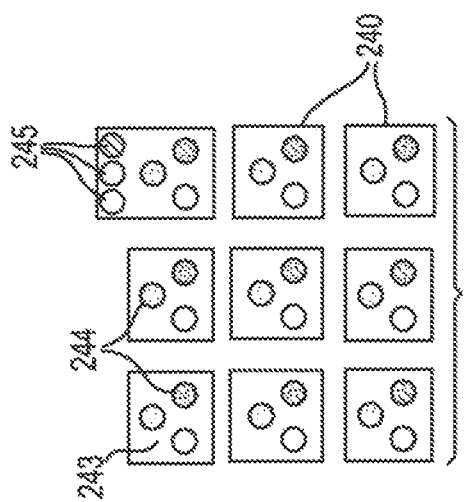
FIG. 5C shows a filter card library included in the spectral imaging system of FIG. 5A.
Figure 5A:
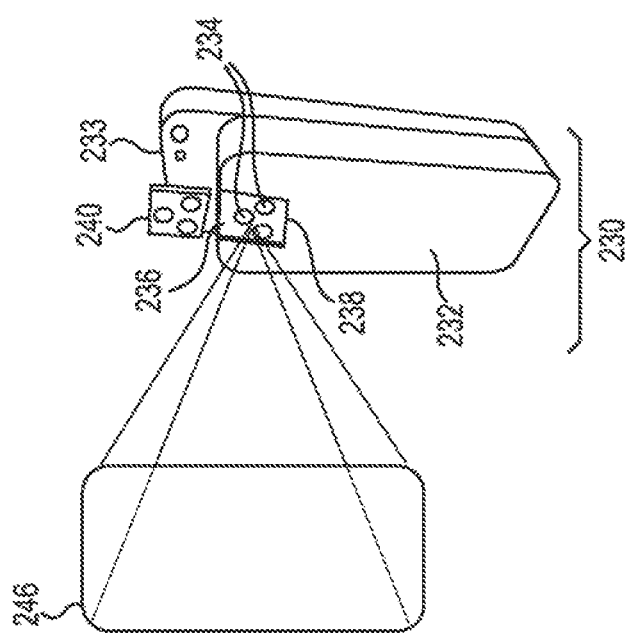
FIG. 5A shows a rear, perspective view of an embodiment of the present invention in the form of a spectral imaging system incorporating a smart phone including an image capture array with an interchangeable spectral filter card and a spectral filter array library.

Another embodiment of a spectral imaging system 230 of the present invention is shown in FIGS. 5A, 5B, and 5C. System 230 includes a camera body 232 wirelessly linked to smartphone 233. Camera body 232 includes a plurality of image capturing elements 234 in a recess 236. Recess 236 is bounded by frame 238 that can be used to hold any one of interchangeable filter cards 240 from filter card library 242. Each filter card 240 includes a base 243 and a plurality of filter elements 244. As an option, some filter cards may have light sources 245, such as LED, installed for one or more wavelengths. For purposes of illustration, one such filter card 240 is being inserted into frame 238. Upon insertion, each of the filter elements 244 on the card 240 optically aligns with a corresponding image capturing element 234. Upon insertion into the camera body 232, system 230 automatically identifies the filter card and selects an algorithm suitable for analyzing captured images to detect one or more target substances associated with that filter card 240. All of the filter cards 240 in library 242 are interchangeably installed into camera body 232 so that system 230 is easily configured to detect a wide variety of target substances corresponding to the filter cards 240 and corresponding algorithms.

Smartphone 233 provides computing power, display for input and output, and an easy touch screen interface for system operations. In one embodiment, the present invention is physically attached to smartphone 233 or other battery-powered mobile device such that the battery capacity within the present invention may be shared with the smartphone 233 or mobile device by connecting the power circuits of the devices or transferring energy via magnetic field link or other suitable coupling.

System 230 can capture a plurality of filtered images (not shown) from a scene 246 and 293. In the embodiment of FIG. 5B, the scene 293 includes target substances 295 and non-target substances 294. System 230 detects the differences in the spectral signatures of the substances 294 and 295 within the scene 293, and displays an output image showing the location of the target substances 295 in a different color 296 than the non-target substances 297 on the display 298 of the smartphone 233. The regions of the display that do not contain the target substance may be displayed in grayscale 297.

System 230 allows specific wavelengths in a portion of the electromagnetic spectrum to be selected to uniquely identify the target substance at issue. Other illustrative applications of this invention may include medical imaging, crop analysis, sanitation, egg inspection, food processing, meat processing, vascular imaging, wound healing, skin cancer and tumor detection, urine analysis, moisture detection, building inspection, vegetation analysis, forensic detection of body fluids, manufacturing, pharmaceutical, nutraceutical, machine vision, mineral screening, sunscreen detection, estrus detection, pest control, hunting, and carpet stain detection.

The ability to capture and evaluate selected wavelengths for different target substances is incorporated into the system via filter elements 244 of the spectral filter array included in card 240 and a custom target algorithm that evaluates captured image information to assess the spectral characteristics corresponding to those of the target substance. With this invention a new target substance may be detected by simply using a different, interchangeable spectral filter card 240 and a different target algorithm associated with the new card. Preferred features of system 230 include the use of a multi-camera array capable of simultaneous image acquisition, an interchangeable filter card, economical charge-coupled device (CCD) detectors (commonly used in digital cameras), calibration methods, high resolution, and displays with custom colormaps. These features help the present invention bring the analysis power of a remote-sensing satellite or hyperspectral imaging system to an economical, compact platform.

The interchangeable filter cards 240 are an advantageous feature of system 230. Choosing among the different interchangeable filter cards 240 can quickly change the spectral characteristics of system 230 to detect different target substances. Individual filter elements 244 of the cards 240 are optically aligned with corresponding spectral imaging elements 234 to allow the acquisition of images that are sensitive to selected wavelengths useful for the accurate detection of a target substance. System 230 is easily configured to detect a different target substance simply by changing the filter card 240. Optionally, interchanging a new filter card 240 may cause system 230 to automatically select an associated target algorithm that has been specifically designed for the newly installed card and its corresponding target substance(s). For example, the present invention may include an indication on the filter card, such as a model number or radio-frequency identification (RFID) tag or the like, that can be read electronically and used by the software of the present invention to automatically load the proper target algorithm and user interface from electronic memory storage resident within the device or located in memory accessible via a network connection, internet, cloud storage, or the like. Thus, as a new filter card is slid into place, the device senses the change, loads the proper target algorithm and modified user interface, such that the system is ready to detect the new target substance with maximum convenience for the user.

Embodiments of the present invention such as system 230 are advantageously derived from CCD-based camera systems, as these are widely available at low cost. These cameras often contain a visible spectrum filter that cuts out ultraviolet light and near infrared light, leaving the camera sensitive to the visible spectrum, approximately 400-700 nm. By removing (or not installing) this filter, the native sensitivity of the CCD sensor is expanded to approximately 300-1100 nm, i.e., from ultraviolet, through visible, to near infrared. Thus, incorporating a plurality of such CCD-based camera systems into a multi-camera array provides a low-cost, high-resolution imaging system suitable for analyzing spectral information at a plurality of selected wavelengths from a relatively wide wavelength range of approximately 300 to 1100 nm. This wavelength range is very suitable for detecting a wide range of target substances. As an alternative to CCD-based sensors, or in addition to CCD-based sensors, other embodiments of the present invention may incorporate near infrared sensors that are sensitive to wavelengths longer than 1100 nm. In another aspect, system 230 can accommodate multiple selected wavelengths by using different kinds of sensors sensitive to different bands. For example, one spectral imaging element sensitive to 600 nm may be implemented via a CMOS sensor. A second spectral imaging element sensitive to 800 nm may be implemented via a CCD sensor. A third array spectral imaging element sensitive to 1500 nm may be implemented via a GaAs-based sensor.

Advantageously, system 230 incorporates and converts a common smartphone into a high-resolution, chemical imaging tool. Additionally, the small size and low-power requirements make the device ideally suited for mobile, aerial or stationary operation. The universal platform, using a multi-camera array with interchangeable filter elements, permits the economies of high-volume manufacturing to be achieved for a base unit while still enabling a wide range of target substances to be detected by simply changing filter arrays. This invention may also be used with other computing devices such as tablet, mini-tablet, laptop and desktop computers. System 230 may be connected to any number of outside devices via connectivity standards common to smartphones and computing devices. Examples of such connectivity interfaces include, but are not limited to, Wi-Fi, Bluetooth, and/or numerous additional wireless standards. In another embodiment, the wireless link may be replaced by any suitable wired link. Examples of wired links are selected from at least one of USB, Firewire, Ethernet, custom, proprietary, or a multitude of other wired standards.

Available light sources vary in their spectral output. Natural sunlight provides a wide range of spectral output sufficient for most applications. However, artificial lighting might include incandescent lighting, fluorescent lighting, white LED lighting, compact fluorescent lighting or other light sources. Each of these artificial light sources provides a narrower output spectrum than natural sunlight. For example an incandescent light provides good illumination in the visible and near infrared, but provides a lower intensity in the ultraviolet spectrum. Fluorescent light provide visible and some ultraviolet illumination, but exhibits lower output in the near infrared region. Consequently, in some embodiments, system 230 may be used in combination with artificial light sources to help minimize the impact of different lighting situations upon detection accuracy. For example, the interchangeable filter cards 240 optionally may contain LED or other illumination sources to more effectively and uniformly illuminate the field of view at the desired wavelengths. Power to the illumination source(s) may be obtained from the system 230 power supply, a separate power source, the base smartphone device, or even a battery supply incorporated into another component of system 230. Other auxiliary light sources may be selected from any number of light sources, such as incandescent, ultraviolet, near infrared, infrared, tungsten, mercury vapor, sunlight, Xenon, quartz halogen, compact fluorescent, high pressure sodium, and metal halide, or combinations of these. The auxiliary light source(s), if any, may be positioned in an advantageous position in order to illuminate the target field of view. The auxiliary light source(s), if any, may also be controlled by the present invention.

The advent of inexpensive, high-resolution, miniature cameras for the smartphone and security markets provides powerful components to couple with the image processing strategy of the present invention. Miniature cameras with 8 to 13 megapixel resolution are now common. Rather than sequentially swapping filters in front of a single large, expensive camera, it is now cost-effective to operate an array of miniature, high-resolution image capturing elements in parallel. Using such a multi-camera array, the present invention includes an interchangeable spectral filter array on a module or card that can be placed in front of the multi-camera array. When the characteristics of each filter element are selected as previously described, it becomes possible to conveniently change the spectral characteristics of the multi-camera, multi-filter arrays. A new target algorithm to optimize the information obtained from the target substance can be readily installed either by manual or automated selection such as from an electronic directory resident within the device or located in memory accessible via a network connection, internet, cloud storage, or the like. The automated selection of the proper target algorithm may be triggered by an identification characteristic, such as a part number, on the newly installed filter card or module.

With this interchangeable filter and algorithm capability, the ability to detect additional target substances can be implemented quickly by examining the spectral characteristics of the new target substance, determining the necessary wavelengths and filter requirements, designing the new target algorithm, then using a new filter card and applying a new software algorithm to optimally extract information from the new target substance.

In some modes of the present invention, an alternative embodiment of system 230 may be available having a relatively low number of image capturing elements 234 and spectral filter elements 244, for example 2 to 4 of such element pairs 234/244. FIG. 5A schematically illustrates such an embodiment having three spectral imaging elements 234. Such embodiments are capable of detecting information from a modest set of target substances. In other embodiments of the present invention, another embodiment of system 230 may be available having a higher number of spectral imaging elements 234, for example 5 to 12 spectral imaging elements. Such higher element embodiments will be capable of detecting information from a larger set of target substances.

In some embodiments, system 230 optionally includes a global positioning system (GPS) capability to geographically locate the images acquired. To accomplish this, system 230 may use the GPS capability of the linked smartphone 233 or other suitable device. System 230 also may use the directional orientation capabilities of the linked smartphone 233 or other device to determine the elevation and direction that the camera array is aimed. In a specific application of these principles, system 230 may use GPS capabilities (or even manual entry) to locate crop vegetation data and orient these data on a map of the crop field. Crop features may be color coded or otherwise marked to indicate the health of the crop at various locations in the field. An accumulation of multiple images may be used to cover large portions of a crop or even an entire field.

As an option, system 230 may incorporate electronically, tunable filter elements as all or part of one or more spectral filter arrays. Such tunable filter elements could replace all or part of the interchangeable filter cards 240 with an array of tunable filters for which the desired wavelengths may be electronically selected. Optionally, any detection pair (i.e., a particular filter element 244 and its corresponding image capturing element 234) may further incorporate at least one polarizing or other kind of spectral filter within the optical path, either on the interchangeable filter card or as part of the multi-camera array, or as a separate component, to reduce glare or otherwise modulate spectral information from the target field of view. Any spectral variation introduced by the polarizing filter desirably is accounted for via a suitable calibration process.

In FIGS. 5A and 5B, camera body 232 is shown as a separate hardware component that is mounted to smartphone 233. In other embodiments, multi-camera capability may be incorporated directly into a smartphone, mobile device, tablet, mini-tablet, laptop computers, desktop computer or other computing device to provide a spectral imaging system of the present invention in a single, integrated device.

In another embodiment, the camera body 232 and smartphone 233 need not be physically coupled together. Instead, these may be operated at a distance from each other. Camera body 232 and smartphone 233 may communicate with each other in any suitable way such as by a wireless and/or wired connection. In such a configuration portions of the user interface and processing may be conveniently distributed in either part or allocated between both parts of the system.

The integration of smartphone 233 into system 230 provides more advantages. Optionally, a color or grayscale camera integrated into the smartphone 233 may be used as part of the multi-camera array to provide a spatial orientation image when displaying detection results. For example, pixels of the spatial orientation image corresponding to the detected target substance can be highlighted via color or other indicia to show the precise locations of the target substance in the spatial orientation image. Additionally, the camera system within the smartphone may be used as a viewfinder to aim the smartphone/multi-camera assembly, whereby the multi-camera system is used to acquire at least a portion of the captured images when the system is actuated.

Spectral imaging systems of the present invention generally include two or more detection pairs of camera elements and corresponding spectral filter elements. FIGS. 6, 7, 8 and 9 shows alternative embodiments of spectral imaging systems 260, 262, 264, and 266 of the present invention containing different numbers of detection pairs. System 260 includes multi-camera array 268 and filter array 270. System 260 is an example of an embodiment in which multi-camera array 268 includes two camera elements. Filter array 270 includes two filter elements, each aligning with a corresponding camera element. System 262 includes multi-camera array 272 and filter array 274. System 262 includes three detection pairs of camera elements and corresponding filter elements. System 264 includes multi-camera array 276 and filter array 278. System 264 includes seven detection pairs of camera elements and corresponding filter elements. System 266 includes multi-camera array 280 and filter array 282. System 266 includes 100 detection pairs of camera elements and corresponding filter elements.

FIG. 10 shows another embodiment of a spectral imaging system 300 of the present invention in which spectral imaging arrays 302 and 304 are deployed at a plurality of different locations relative to a scene 314 being imaged. Spectral imaging array 302 includes multi-camera array 306 and filter array 308. Arrays 306 and 308 provide seven detection pairs for purposes of illustration. Spectral imaging array 304 includes multi-camera array 310 and filter array 312. Arrays 310 and 312 provide seven detection pairs for purposes of illustration. In this embodiment, the two spectral imaging arrays 302 and 304 are positioned and aimed to examine two sides of a target (not shown) in scene 314.

Figure 11:
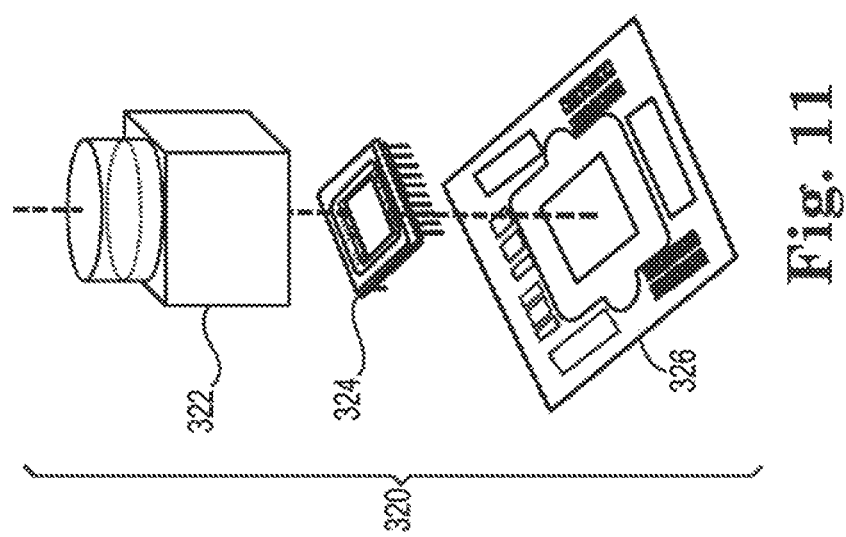
FIG. 11 shows an embodiment of a camera element of the present invention.

An advantage of the present invention is that many different kinds of camera elements may be used in the spectral imaging systems. FIG. 11 shows a typical embodiment of a camera element 320 including lens assembly 322 and image sensor 324. Typically, a plurality of camera elements 320 are appropriately coupled to a common circuit board 326. Circuit board 326 may serve not only a plurality of camera elements but also other components of a spectral imaging system. In other embodiments, each camera element 320 may incorporate its own dedicated circuit board. Lens assembly 322 and image sensor 324 may be mounted to circuit board 326 as shown or may be remote and coupled to board 326 by suitable wired or wireless interconnects.

Figure 12:
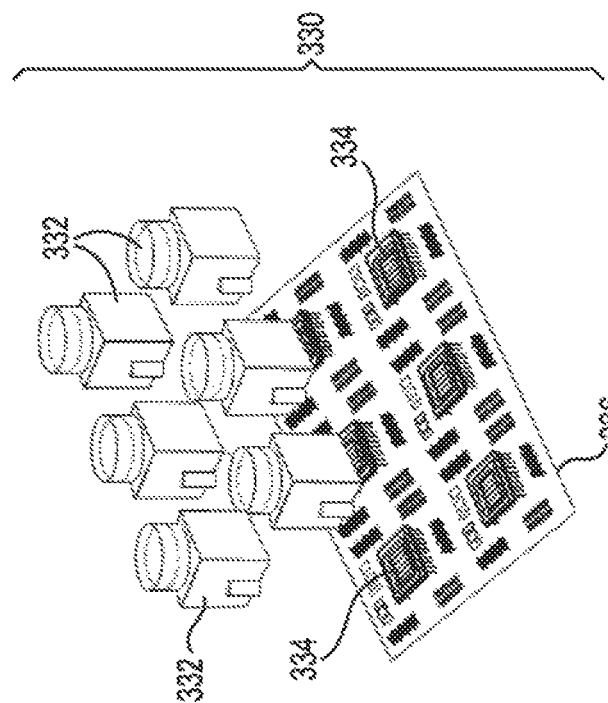
FIG. 12 shows an embodiment of a six-element, multi-camera array of the present invention.

FIG. 12 shows an example of a multi-camera array 330 including 6 detection pairs. Array 330 includes six lens elements 332 and a corresponding array of six image sensors 334. The lens elements 332 and sensors 334 are mounted on a common circuit board 336.

Figure 13:
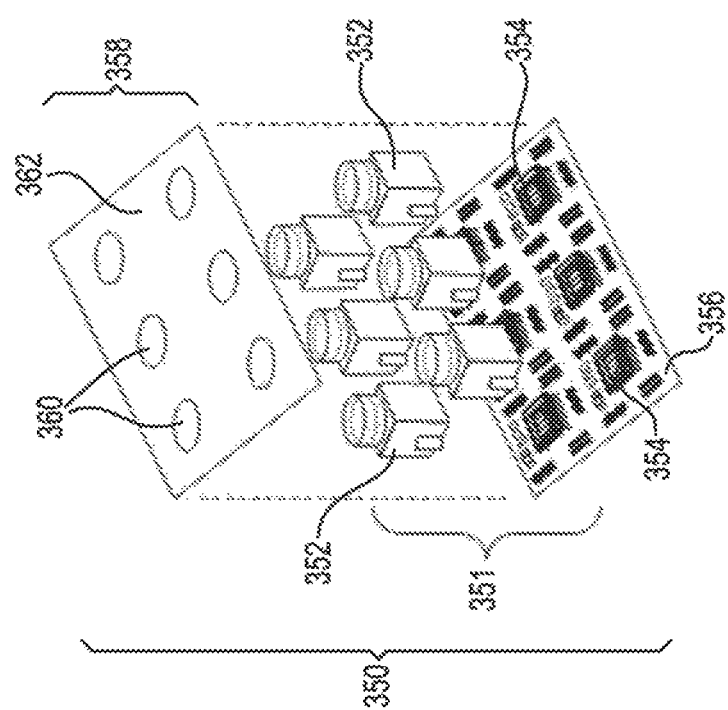
FIG. 13 shows an embodiment of a spectral imaging system of the present invention with an interchangeable filter array.

FIG. 13 shows an example of a spectral imaging system 350 whose detection capabilities are easily configured to detect a wide range of target substances. System 350 includes multi-camera array 351 and spectral filter array 358. Multi-camera array 351 includes a lens array of lens elements 352 and corresponding sensing sensor array of sensors 354. Lens elements 352 and sensors 354 are coupled to circuit board 356. Filter array 358 includes card 362 incorporating filter elements 360. Each filter element 360 aligns with a corresponding lens element 352. Filter array 358 allows the multi-camera array 351 to be sensitive to capturing image information for a plurality of pre-determined wavelengths. The wavelengths are pre-selected so that the captured image information can be used to detect a target substance in the field of view of the system. Filter array 358 is easily interchanged with another filter array (not shown) of similar size and similar distribution of filter elements so that the other filter array aligns with the lens array. By using a different combination of filter elements in the other filter array, the spectral sensitivity and hence detection capabilities of the system 350 is expanded to encompass one or more other target substances. By providing a larger inventory of such arrays, and by providing programming instructions that allow the system to interpret the spectral information captured when using the various filter arrays, system 350 can be used to detect a vast number of target substances on demand.

FIG. 14 shows an example of a spectral imaging system 380 including spectral imaging capabilities based on 120 detection pairs. System 380 includes spectral filter array 382, lens array 384, sensor array 386, and circuit board 396. Filter array 382 includes a 12×10 array of spectral filters 388 supported on substrate 390. Filter array 382 is interchangeable with other filter arrays (not shown) to expand the detection capabilities of system 380. Lens array 384 includes a 12×10 array of lens elements 394 that are optically aligned with corresponding filter elements 388. Sensor array 386 includes a 12×10 array of image sensors 398. The image sensors 398 are aligned with corresponding lens elements 394.

The focusing of the images onto the image capture elements within the image capture array of the present invention may be accomplished in accordance with any suitable method(s). Examples include, but are not limited to, manual focus, numerous autofocus methods and focus methods under the control of program instructions. The focus of an individual detection pair, also referred to as a channel, may be made independently or in coordination with one or more other channels.

An advantageous characteristic of many embodiments of the present invention, including but not limited to those embodiments as illustrated in FIGS. 12 and 13, is that chromatic aberration is reduced or even avoided. Chromatic aberration is a common distortion of optical systems using lenses. This distortion plagues many conventional spectral imaging systems, such as those that use a spinning wheel of filter elements passing different wavelengths through a single lens and single camera lens system. The refractive index of lens materials varies with wavelength. This causes different wavelengths to be focused by a single lens at different distances from the lens. Camera manufacturers have designed various complex and expensive lens configurations to minimize this distortion with only marginal success over a broad range of wavelengths. The present invention solves this problem, even for simple, inexpensive lenses, since the present invention has a separate spectral channel for each selected wavelength. The optimal focus for each wavelength channel may be established and left in place while acquiring images. This permits the present invention to acquire images simultaneously and at video or faster frame rates. There is no need to sequentially refocus the system between each new wavelength acquisition, as is the case with conventional technologies.

In some modes of practice, the present invention provides a solution to chromatic aberration by providing independent filter/camera channels (i.e., detection pairs) for each selected wavelength, permitting the distance from a lens to the focal plane to be adjusted independently to properly focus the spectral image on the image plane of the image capture sensor.

In some modes of practice, an optional correcting lens may be included as part of the interchangeable spectral filter card, which corrects for deviation in focus due to the wavelength of the specific spectral filter element.

In some modes of practice, an optional complex lens design that compensates for variations in wavelength and refraction index may be used as part of the present invention.

In some modes of practice, individual lenses in an image capture array may be adapted, e.g., offset relative to a common image plane or have an altered curvature, etc., so that each lens in the array can capture and independently focus filtered light onto the image plane. Such an adaptation is desirable because each lens is intended to capture filtered light in a particular bandwidth that may require a different focal length than other bandwidth portions captured by other lenses in the array.

In some modes of practice, an aperture of a lens/camera system is adjusted to increase the depth of field and reduce the chromatic aberration with minimal change in focus.

In some modes of practice, the present invention may determine a focus for one channel and then compute a corresponding focus for additional channels based on the corresponding lens characteristics and the center wavelength of each corresponding spectral channel.

One of the strengths of the present invention is its flexibility in easily generating target algorithms for a wide variety of target substances. The form and design of a target algorithm has few restrictions. The target algorithm may be formulated to take advantage of the characteristics of the target spectrum and the number of wavelengths available in a given product model. Some target substances may be easily detected or measured using only a few selected wavelengths, e.g., 3 wavelengths. More complex detection efforts, e.g., wherein a target substance has many spectral similarities to other features in the captured image information, may involve using a greater number of selected wavelengths, e.g., 10 or more, for detection.

For example, when the principles of the present invention are used to detect water as described herein and depending upon other materials in the background, a simple ratio between the spectra sampled at two different wavelengths would be quite effective to detect water in a field of view of a spectral imaging system. If spectral information for a particular image pixel demonstrates such a ratio, the system may accurately conclude that water is present in the captured image at that pixel location. If the ratio is not demonstrated, there is no water detected at that pixel location. The system can perform this analysis for every pixel (or at another resolution, if desired) to comprehensively detect and map the location(s) of water throughout the captured image information. Even with this simple example, there is great flexibility in the selection of the wavelengths and the manner in which they are compared to identify or measure the target substance.

For an exemplary goal, such as to identify a given target substance using two wavelengths, one algorithm criterion may involve the identification of a narrow spectral peak in the spectrum of the target substance. This criterion is based on the principles that background substances are likely to have different peaks or broader transitions. To this end, two parameters are selected to optimize, namely the ratio between the spectra amplitudes and the separation of the wavelengths, with a narrow separation being preferred. It is possible to optimize both parameters by writing the exemplary formula below which defines a three-dimensional, optimization surface:

$$S(\lambda_i - \lambda_j) = [R(\lambda_i)/R(\lambda_j)]/|(\lambda_i - \lambda_j)|$$

$$\lambda_i = \min(\lambda_1): \max(\lambda_1) \text{ and}$$

$$\lambda_j = \min(\lambda_2): \max(\lambda_2) \quad (1)$$

where $\lambda_1$ and $\lambda_2$ are the range of the first and second wavelength, respectively; $\lambda_i$ and $\lambda_j$ are the indexed wavelengths within the range of $\lambda_1$ and $\lambda_2$, respectively; $R(\lambda_i)/R(\lambda_j)$, is the ratio of the reflectance spectrum at indexed wavelengths; and $S(\lambda_i - \lambda_j)$ is the optimization surface. The optimization surface, $S(\lambda_i - \lambda_j)$, may then be searched for a maximum. The wavelengths near that maximum are candidates to become the selected wavelengths for implementation in the multi-filter array and the target algorithm. A similar strategy may be used for more than two wavelengths. Numerous other formulas and methods may be useful to select a given number of wavelengths which may be used, in turn, to identify the chosen target substance.

Once the wavelengths are selected as suggested above, signal processing and statistical analysis methods may be used within a target algorithm to detect the target substance using spectral information at the selected wavelengths. Such methods include, but are not limited to, eigenvalue analysis, correlation analysis, principle component analysis, signal detection theory, pattern recognition, and multivariate analysis. An important feature of the present invention is the great freedom it provides to use a variety of effective target algorithms to accurately detect the target substance while still providing a platform that is economical, low-power, mobile, and high resolution.

In some modes of practice, the target substance may be a pure substance. In other modes of practice, the target substance may be a mixture of one or more substances. The design of the target algorithm(s) can easily accommodate mixtures, because mixtures often exhibit spectral information that is different in a plurality of respects from the pure substances that make up the mixture. In the case of such a mixture, spectra may be acquired at various concentrations and analyzed to create corresponding target algorithm(s) capable of detecting and even providing quantitative information for mixture variations. This strategy may be used to advantage to actually measure the concentration of a target substance by evaluating the spectra at the selected wavelengths for each level of concentration. One application of this technique is to remotely and noninvasively measure moisture content in any number of substances such as soil, sand, grain, cereal, vegetation, feed, or wall material. An analysis of the spectra in the manner described for mixtures can also be used to evaluate the purity of a target substance or determine what impurities may be present.

The present invention, therefore, may be used to detect not only the presence of a target substance in a field of view but also to measure a quantity of the target substance within the field of view when spectral characteristics vary based on quantity. While a presence may be accurately detected using an accumulation of nominal values for filter attenuation, sensor variations, and light source variations, it may be advantageous to use an in-frame reference surface to calibrate these parameters across the formulation range of interest when making quantitative measurements. The in-frame reference may be used as part of a calibration procedure to quantify the concentration of the target substance. The spectral imaging system can use that information to calibrate the images captured with the in-frame reference in the field of view. For example, a certain ratio between peaks at two or more wavelengths may indicate a concentration of 10.0%, whereas another ratio might indicate a concentration of 25.0%, etc. This allows quantitative information to be determined with great accuracy.

System calibration may be achieved via a number of methods. One such method is a cumulative calibration factor computed from individual calibration factors determined for each system component such as illumination intensity, filter attenuation, lens attenuation, and image capture sensor sensitivity. Using this method, the overall system calibration is the cumulative product of the individual component calibration factors. Another method of calibration involves the use of an in-frame reference with known reflective properties on its surface. The in-frame reference method permits the entire system to be calibrated as a whole and avoids a possible accumulation of errors which may occur with the cumulative calibration factor method. The optimal calibration method for a given application depends on the required accuracy for that specific application and the cost or complexity of the calibration method.

In the cumulative calibration method, one component calibration is for illumination. An exemplary method to obtain a calibration for variations in illumination provides for the image data at each selected wavelength to be normalized to account for variations in illumination near that particular wavelength. In practical effect, this may be described as a multiplication by an illumination normalization factor, $\lambda_{illum}$. This permits an accurate comparison of the spectrum of the target substance at the selected wavelength without undue influence from variations in the illuminating source across the spectrum.

Figure 40:
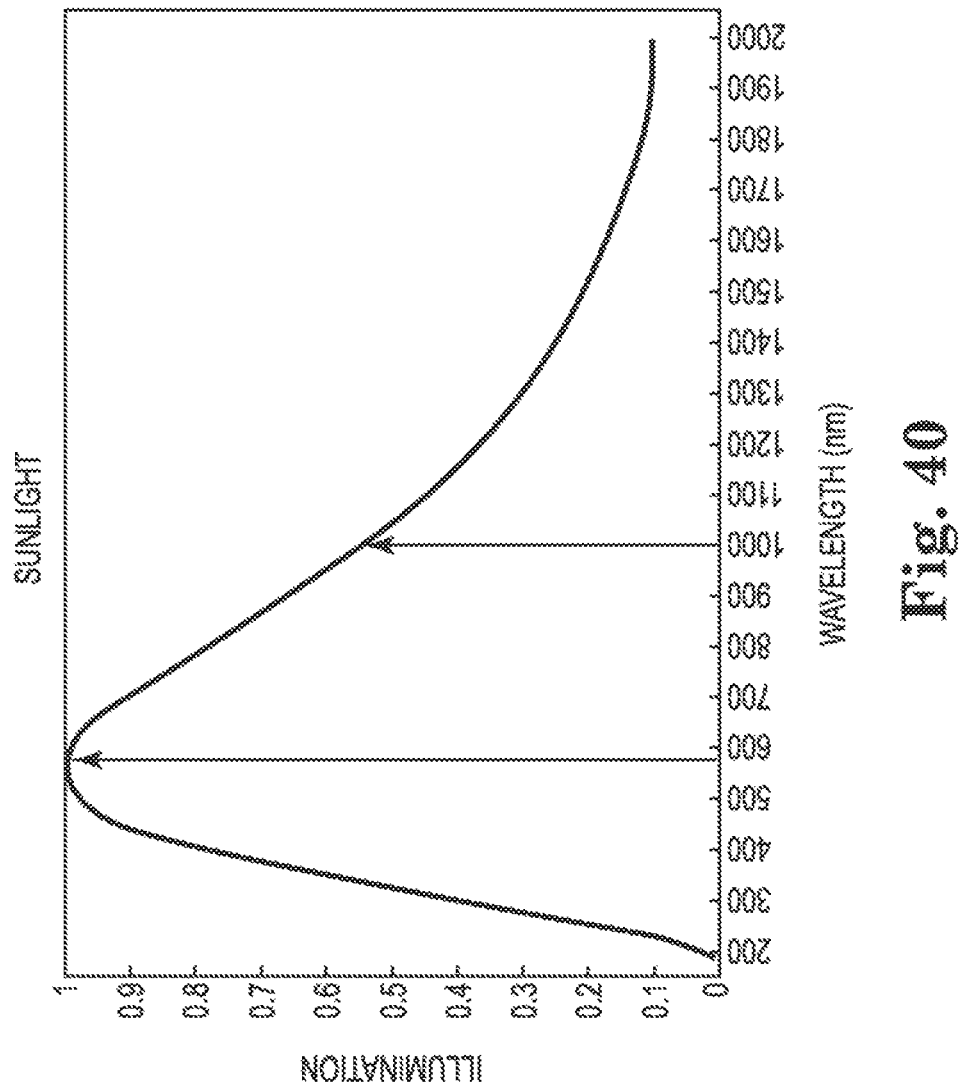
FIG. 40 shows an illumination spectrum of sunlight and two characteristic wavelengths of the spectrum.

As an example, if the illumination from sunlight is as shown in FIG. 40, an illumination normalization factor, $\lambda_{illum}$, may be computed at each selected wavelength to remove the spectral response introduced by the illumination that is independent from the spectrum of the target substance.

In this example, the relative illumination at two wavelengths, 550 nm and 980 nm, respectively, are used to demonstrate the suggested normalization. These wavelengths are shown in FIG. 40.

$$I_{550} = 1.00 \text{ (at 550 nm)} \tag{1}$$

$$I_{980} = 0.586 \text{ (at 980 nm)} \tag{2}$$

$$k_{illum}(550 \text{ nm}) = \frac{1.0}{I_{550}} = 1.000 \tag{3}$$

$$k_{illum}(980 \text{ nm}) = \frac{1.0}{I_{980}} = 1.706 \tag{4}$$

In general terms, the illumination normalization factor, $k_{illum}$, as a function of wavelength, $\lambda$, may be expressed as the reciprocal of the illumination curve, $I(\lambda)$, at each wavelength.

$$k_{illum}(\lambda_i) = \frac{1.0}{I(\lambda_i)} \text{ for non-zero } I(\lambda_i) \tag{5}$$

Illumination curves may be selected from a database list of generic illumination sources such as sunlight, incandescent light, fluorescent light or more specific light sources such as "a 60-watt, soft white GE light bulb" or "tungsten lamp, model 6315 1000 W QTH Lamp3." These illumination curves may reside in a memory base such as, local memory of the present invention, local memory of the associated mobile device, or an on-line or "cloud" database to which the device has access via the internet or other means. In any of these cases, the illumination source data will be such that the relative illumination intensity may be determined at the specific wavelength of a given camera/filter element.

In the cumulative calibration method, another component calibration is for sensor sensitivity. An exemplary method to obtain a calibration for variations in sensor sensitivity provides for the image data near each selected wavelength to be normalized according to the sensor spectral response via multiplication by a sensor normalization factor, $k_{sensor}(\lambda_i)$, where $\lambda_i$ is the ith wavelength used to define the target substance (with other parameters at known levels or already normalized). This permits an accurate comparison of the spectrum of the target substance at each of the selected wavelengths.

Figure 41:
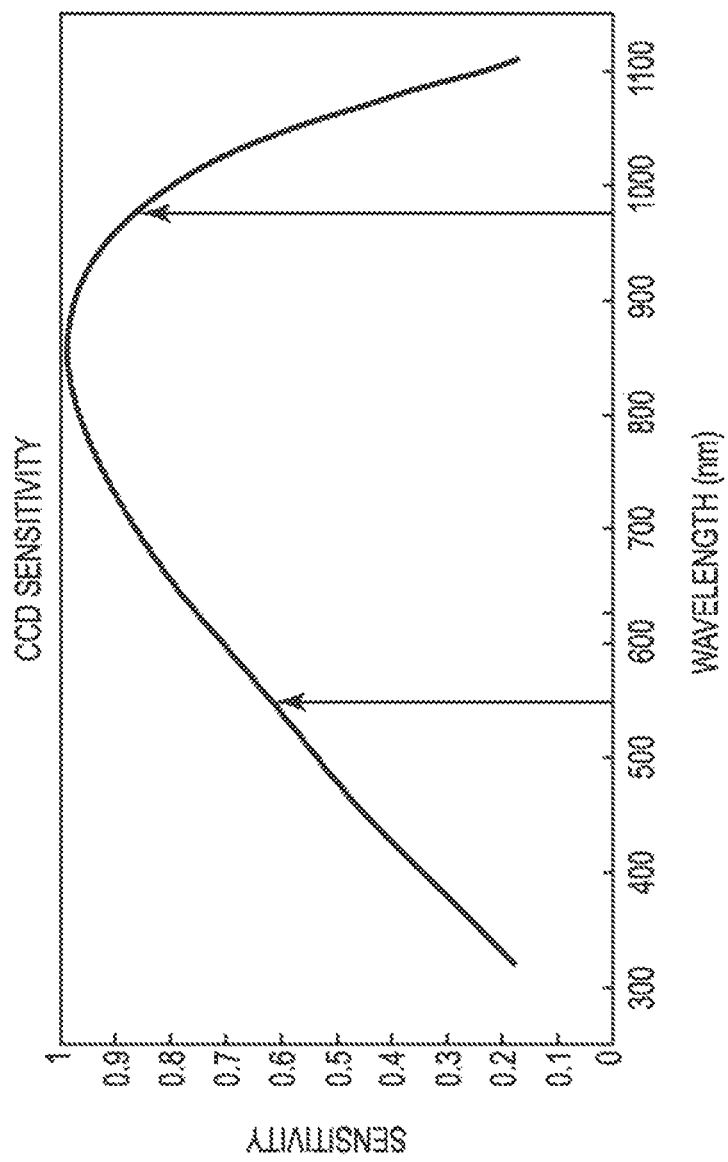
FIG. 41 shows a typical spectral sensitivity curve for a CCD sensor useful in the practice of the present invention as well as two characteristic wavelengths of the spectrum.

As an example, for the spectral sensitivity of a CCD sensor as shown in FIG. 41, a sensor normalization factor, $k_{sensor}(\lambda_i)$, may be computed at each selected wavelength to remove the sensor's spectral response from the evaluation of the target substance spectrum.

In this example, the sensitivity at two wavelengths, 550 nm and 980 nm, respectively, are used to demonstrate the suggested normalization. These wavelengths are shown in FIG. 41.

$$S_{550} = 0.620 \text{ (at 550 nm)} \tag{6}$$

$$S_{980} = 0.818 \text{ (at 980 nm)} \tag{7}$$

$$k_{sensor}(550 \text{ nm}) = \frac{1.0}{S_{550}} = 1.613 \tag{8}$$

$$k_{sensor}(980 \text{ nm}) = \frac{1.0}{S_{980}} = 1.222 \tag{9}$$

In general terms, the sensor normalization factor, $k_{sensor}(\lambda)$, as a function of wavelength, $\lambda$, may be expressed as the reciprocal of the sensor sensitivity curve, $S(\lambda)$, at each wavelength.

$$k_{sensor}(\lambda_i) = \frac{1.0}{S(\lambda_i)} \text{ for non-zero } S(\lambda_i) \tag{10}$$

The sensor response curve may be determined for each individual sensor device as part of the manufacturing process where that sensor curve is stored in a memory base, such as a device memory or may also be acquired by looking up an identification number for the device in an on-line or "cloud" database to which the device has access via the internet or other communication system. In any of these cases, the sensor sensitivity data will be such that the relative sensor sensitivity may be determined at the specific wavelength of a given camera/filter element.

Additionally, the sensor sensitivity curve may be re-measured and recorded in a memory base such as, local memory, an on-line database, or a 'cloud' database and made available for calibration purposes. This recalibration of the device may be performed at regular intervals determined by the aging characteristics of the sensor.

In the cumulative calibration method, another component calibration is for filter gain. Each discrete narrow band spectral filter used with a camera element typically has some losses. To account for these losses, a filter normalization may be practiced that uses the filter gain, $A_{filter}$, for each filter element. As an example, the discrete wavelengths of 550 and 980 nm are used.

$$A_{550} = 0.85 \text{ (at 550 nm)} \tag{11}$$

$$A_{980} = 0.80 \text{ (at 980 nm)} \tag{12}$$

$$k_{filter}(550 \text{ nm}) = \frac{1.0}{A_{550}} = 1.176 \tag{13}$$

$$k_{filter}(980 \text{ nm}) = \frac{1.0}{A_{980}} = 1.25 \tag{14}$$

In some modes of practice, the system calibration may be accomplished via an accumulation of normalization factors specified for each component in the system. This method is represented by the formula below for each spectral component.

$$I_{cal}(\lambda_i) = k_{illum}(\lambda_i) k_{sensor}(\lambda_i) k_{filter}(\lambda_i) I_{measured}(\lambda_i) \tag{16}$$

where the normalization factors, $k_{illum}$, $k_{sensor}$, and $k_{filter}$ are as described above; $I_{measured}(\lambda_i)$ is the uncalibrated intensity as measured at wavelength, $\lambda_i$; and $I_{cal}(\lambda_i)$ is the calibrated intensity for the target surface at the designated wavelength, $\lambda_i$.

In general terms, the filter normalization factor, $k_{filter}(\lambda)$, as a function of wavelength, $\lambda$, may be expressed as the reciprocal of the filter gain, $A_{filter}(\lambda)$, at each wavelength $$k_{filter}(\lambda_i) = \frac{1.0}{A(\lambda_i)} \text{ for non-zero } A(\lambda_i) \tag{15}$$

The cumulative calibration method may be advantageous for the detection of the presence of a target substance. The normalization factors for the illumination source, sensor sensitivity, and filter element gain may be retrieved from calibration data stored in memory. The illumination source may be selected from a list of typical sources which may be encountered such as sunlight, incandescent, fluorescent, tungsten, LED, or other light sources with commonly known spectral emissions. The sensor calibration may be obtained by an initial calibration at the time of manufacture, periodically updated as needed. The filter efficiency is available as a specification for each individual filter element, perhaps confirmed at the time of manufacture.

In illustrative modes of practice, an in-frame reference may be used to more precisely calibrate all system components at once. Such a calibration may use a single surface (or multiple surfaces), broadband, in-frame reference (or reflector) with known spectral characteristics. In the case where the in-frame reference spectrum is uniform at the selected wavelengths, the system calibration vector, $k_{system}(i)$ may be computed according to the following formula:

$$k_{system}(i) = \frac{1}{I_{ref\_surf}(i)} \text{ for } i = 1 \text{ to } n \tag{18}$$

where i is an index representing each multi-camera capturing element (and its corresponding filter element); n is the number of elements in the multi-camera array (excluding the spatial orientation image element if it presents the entire visible spectrum); and $I_{ref\_surf}(i)$ is the intensity of the in-frame reference surface as acquired in the image of each element of the multi-camera array.

As an example, for a four-element, multi-camera array including four different wavelengths, a calibration array might be written, using equation 18, as:

$$K_{system} = [k_{system}(1) \; k_{system}(2) \; k_{system}(3) \; k_{system}(4)] \tag{19}$$

$$= [1.732 \; 1.523 \; 1.122 \; 2.455]$$

where the system calibration constants, $k_{system}(1)$ through $k_{system}(4)$, are the calibration constants for each image acquired from each multi-camera element, respectively. These calibration constants represent a calibration for the entire spectral path of the given camera/filter element pair. In this example, the calibration images, $\text{Image}(i)_{cal}$, obtained from each uncalibrated (raw) image, $\text{Image}(i)_{raw}$, may be computed in the following manner:

$$\text{Image1}_{cal} = k_{system}(1) \; \text{Image1}_{raw} = 1.732 \times \text{Image1}_{raw}$$

$$\text{Image2}_{cal} = k_{system}(2) \; \text{Image1}_{raw} = 1.532 \times \text{Image1}_{raw}$$

$$\text{Image3}_{cal} = k_{system}(3) \; \text{Image1}_{raw} = 1.122 \times \text{Image1}_{raw}$$

$$\text{Image4}_{cal} = k_{system}(4) \; \text{Image1}_{raw} = 2.455 \times \text{Image1}_{raw} \tag{20}$$

with the corresponding selected wavelengths expressed by a wavelength vector:

$$\Lambda = [\lambda_1 \lambda_2 \lambda_3 \lambda_4] = [550 \; 650 \; 830 \; 980] \text{ nm} \tag{21}$$

In cases where the spectrum of the in-frame reference is not uniform across the selected wavelengths, the measured spectral amplitudes may be normalized according to variations in reference levels and then the formulas above may be applied.

The in-frame reference calibration method has the potential for greater system precision since undue accumulation of normalization factor errors is avoided by accounting for the normalization factors all at once. This method is particularly advantageous for applications where a quantitative measurement of the target substance is desired.

It should be noted that the two described embodiments for system calibration proposed above should yield nearly equivalent results with the second, the in-frame reference method, expected to be somewhat more precise. Therefore, $$k_{system}(i) \sim k_{illum}(\lambda_i) k_{sensor}(\lambda_i) k_{filter}(\lambda_i) \tag{22}$$

where $k_{system}(i)$ is the system normalization for the ith camera element sensitive about wavelength, $\lambda_i$; with the remainder of the normalization factors as previously described.

It may also be desirable to adjust the acquired images for individual camera optics such as aperture, shutter speed, depth of field, and focus. One solution is to link the optical and spectral features of the camera array such that they all change in unison. Another solution is to fix the camera optics with the same parameters. A third solution is to permit each element to optimize certain parameters which are mathematically accounted for within the calibration or measurement algorithms. Throughout the normalization and calibration process it is desirable to account for variations in intensity such that the relative spectral amplitudes at various wavelengths are maintained.

Advantageously, the present invention may be used in reflectance and/or transmission modes. In reflectance mode the light reflects from the target surface and is detected by the system components. In the transmission mode, the light is transmitted through the target surface and then continues on to be detected by the sensors within the system. Subjects such as vegetation, minerals, fresh produce, and fluorescent paints typically are viewed in the reflectance mode. Subjects such as liquids or gasses are often viewed in a transmission mode. Some substance may be viewed in either mode individually or in both modes simultaneously, such as mammalian skin and tissue. It is important to use the proper spectrum for reflectance or transmission (absorption) modes, respectively, because transmission and reflectance spectra for a particular substance may not be the same. For example, spectral peaks in a transmission spectrum may be at different wavelengths and/or have different amplitudes than spectral peaks in a reflectance spectrum.

One embodiment of the present invention uses a permanent, stationary geometry of the multi-camera array. In this embodiment, all elements of the multi-camera array are spatially fixed with respect to each other (such as by permanent mounting each camera element on the same circuit board). Thus, a registration between images from various camera elements can be determined at the time of manufacture.

In another embodiment, a reference target surface with an advantageous target subject matter may be used to derive a registration formula to fully register the images from various camera elements. With this embodiment, the registration or alignment of the various images from the individual camera elements can be empirically determined at the time of manufacture and an alignment formula stored in digital memory. Such an alignment formula can then be recalled as needed throughout the lifetime of the product.

An advantageous alignment target, used to optimally register or align the individual images, may be selected or created to have similar features visible to all camera elements regardless of their spectral sensitivity. Using this alignment target, images can be acquired that are ideal for generating an alignment mapping function. An alignment mapping function can be generated for each camera element within the array, transforming them to a common or reference axis.

Another embodiment of the present invention may use focus or zoom capability. In this embodiment a stationary mapping function is used with an added mathematical formula to compensate for a change in focus or zoom. Such an additional formula will include an image scaling component to account for a change in image size due to focus or zoom capability.

Advantageously, the present invention provides a common platform capable of performing spectral image analysis for numerous, diverse detection and analysis applications. Exemplary applications include, but are not limited to, chemical composition analysis, water and moisture detection, water analysis, crop analysis, vegetation identification, vegetation mapping and infestation tracking, soil analysis, disturbed soil analysis, cranberry analysis, inspection of fruits and vegetables, locating missing persons, inspection of nuts, seeds, legumes and grains, robotic harvesting of fresh produce, biofilm detection, hand washing, food safety and processing, infection control, egg inspection, bird vision, forensics and criminology (e.g., detection of fingerprints, urine, blood, semen, hair, and the like), vascular imaging, diabetic foot perfusion, peripheral vascular disease, wound healing, feedback for cardiopulmonary resuscitation (CPR), cardiovascular risk assessment via a reactive hyperemia protocol, surgical tool inspection, surgical tool to indicate vascular clamping, lymphatic imaging and surgery, evaluating peripheral artery disease (PAD), breast and other cancer detection, medical imaging, medical diagnostic information automatically linked to an individual subject, veterinary and human applications, estrus detection, building inspection, floor cleaning, pest control, vehicle diagnostics, detection of fluorescent dyes, sanitation, mineral detection and processing, frac sand supply and use, meat processing, poultry processing, sunscreen analysis, animal feed inspection and analysis, security and forgery detection, authentication, hunting, consumer color matching, tattoos and other body art, gas detection, liquid classification, oil production, chemical processing, manufacturing, pharmaceuticals, nutraceuticals, sustainability, road conditions, and the like.

Chemical Analysis

In one aspect, the present invention relates to a method to acquire simultaneous images in order to analyze the chemical composition of a target surface within a field of view.

Water and Moisture Content

In one aspect, the present invention relates to a method to derive information about water within a target field of view. If the target substance is a volume of water, the selected wavelengths might be one wavelength in which water is absorbed, such as 980 nm, and one wavelength in which water exhibits little absorption, such as 766 nm. Filter elements would contain bandpass filters for each of the selected wavelengths. After image alignment, a simple ratio of image intensities for corresponding pixels would yield an indication of the presence of water.

In another aspect, moisture may be detected by comparing image intensities at two or more different wavelengths where the wavelengths are selected by an analysis of the spectral reflectance properties of moisture. After image alignment, the presence of moisture may be determined by the ratio of image intensities at the different wavelengths. Ratios greater than a given threshold could be indicative of the presence of moisture.

In another aspect, the ratios described above for the detection of moisture may be calibrated via an in-frame reference surface in order to calibrate a given ratio value with a given percentage of moisture. Such a calibration may be used to determine a quantity of moisture present within the target surface. Such applications are valuable for measuring the moisture content of many substances, such as soil, cereal, food products, meat, snow, crops, vegetation, sheet rock, concrete, chemical products, frac sand, building construction, and minerals.

Water Analysis

In another aspect, the present invention relates to a method to analyze substances present in water. As discussed herein, the spectral absorption band of water near 980 nm is narrow. This characteristic permits the identification of water with a filter element sensitive near 980 nm. Adjacent bands, outside of the water absorption band, are available to detect impurities, contaminants or formulations within the water. Examples of such uses include but are not limited to, pollution detection, on-site water analysis, aerial inspection of water quality, beverage processing, wastewater treatment, drinking water treatment, biosecurity at reservoirs, toxicity analyses, presence of organic material, presence of organisms, groundwater analysis and underwater exploration or mining.

Crop Analysis

In one aspect, the present invention relates to a method to analyze a crop. In such an application the multi-camera array is aimed at a crop in order to derive information regarding the condition of the crop. This may include, but is not limited to, a crop condition such as nitrogen content, chlorophyll content, crop maturity, moisture content, disease state, insect infestation, fungus infestation, mold content, mildew content, weed content, plant maturity, harvest readiness, and fertilizer effectiveness.

Figure 15:
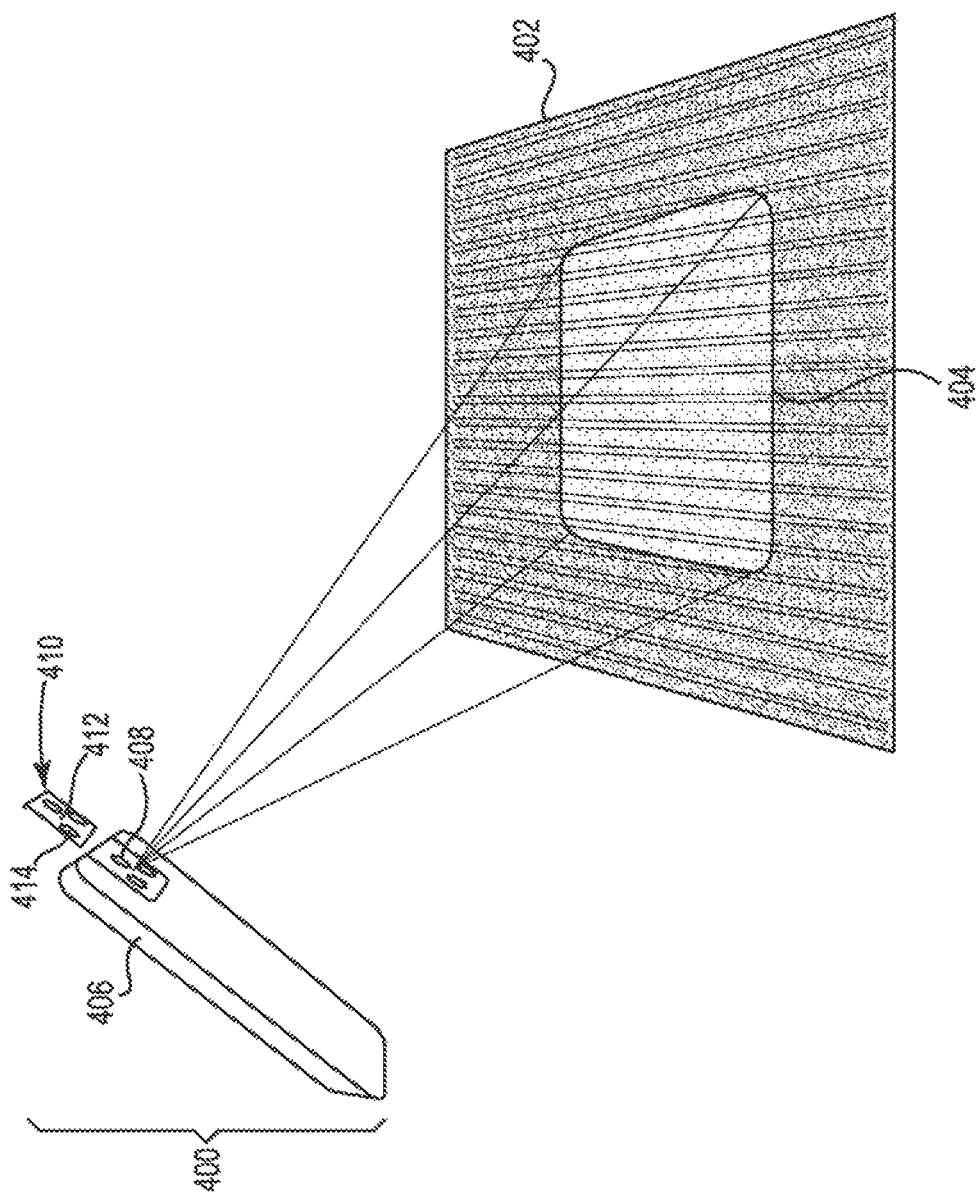
FIG. 15 shows an embodiment of a spectral imaging system of the present invention analyzing a crop.

FIG. 15 illustrates the use of a spectral imaging system 400 of the present invention to analyze a crop 402 within a field of view 404. System 400 includes an image capture array 406 including a trio of image capture elements 408. System 400 also includes a filter card 410 including spectral filter array 412 that includes a trio of filter elements 414. The filter elements 414 are selected to be sensitive to the desired crop characteristics. When filter card 410 is inserted into system 400, filter elements 414 optically align with image capture elements 408 to allow each of the image capture elements 408 to capture an independent, filtered image of crop 402. System 400 may further include a smartphone (not shown) integrated with image capture array 406 and spectral filter array 412. The spectral imaging system 400 is positioned at an elevation sufficient to view at least a portion of the surface of crop 402 within a field of view 404. A corresponding target algorithm is provided to analyze the acquired spectral images and compute the desired crop information.

Crop data acquired via system 400 in FIG. 15 may be communicated to any number of outside devices via connectivity standards common to smartphones and computing devices. Examples of such connectivity interfaces include, but are not limited to, Wi-Fi, Bluetooth, and/or numerous additional wireless standards. If useful, the wireless link may be replaced by any suitable wired link. Examples of wired links are selected from at least one of USB, Firewire, Ethernet, custom, proprietary, or a multitude of other wired standards.

Positioning and aiming the system 400 at the crop 402 may be accomplished in a variety of ways, including one or more of securing the invention within or on an aerial apparatus such as a commercial aircraft, private aircraft, glider, satellite, spacecraft, unmanned aerial vehicle, remote control aircraft, drone, blimp, lighter than air aircraft, manned balloon, weather balloon, projectile, rocket, personal air vehicle, paraglider, kite, or extraterrestrial aircraft; attaching the invention to a flying animal such as a bird or bat; placing the invention in the possession of a skydiver deployed over the crop; attachment to a pole, building, greenhouse, hill, mountain, tree, crane, bridge, overpass, or other permanent, semi-permanent, or temporary structure; attachment to a water tower, cell phone tower, or electrical tower; photographic tripod, mechanical fixture or similar apparatus; handheld or attached to a human; attached to a person via a mechanism, such as a head strap or chest strap; attached to or held by an animal; attached to or held by a robot; attached to a ground-based equipment such as a car, tractor, combine, harvester, plow, irrigation apparatus, spraying system or remote control vehicle; and positioning the invention in any manner that, at least temporarily, enables the crop to be within the field of view of the present invention.

In addition to being used for crop analysis, such positions are also suitable for other applications where an elevated position may be advantageous to capture images of a scene for detection of a desired target substance.

In another aspect, the present invention contains geographical coordinates for each set of images representing a portion of the field of view such that the images and data derived from the images may be assembled into a contiguous collage representing a larger portion of the entire crop field than is contained in any single image set. These geographical coordinates may be embedded in the image data, as is presently done via geo-tagging protocols, or organized in an independent data base.

Many crops may benefit from the use of the present invention. This invention may be applied to any crop that exhibits a spectral response that can be characterized by the spectral amplitudes at a discrete number of wavelengths. Examples of such crops include corn, soybean, wheat, rice, cotton, cranberries, grapes, rye, sorghum, canola, rape seed, peas, sugar beets, oats, alfalfa, sugar cane, tomatoes, potatoes, edible beans, coffee, oranges, grapefruits, apples, nuts, peanuts, legumes, strawberries, blueberries, blackberries, onions, tobacco, peppers, spinach, broccoli, carrots, grass, brome, lupines, and avocado.

Crop analysis may include, but is not limited to, soil analysis, soil analysis for the purpose of fertilizer distribution, growth tracking, plant maturity analysis, insect infestation, disease, nutrient content, stress levels, mold detection, mildew detection, weed analysis, crop dusting, harvest readiness, and the like. In another aspect the present invention may be used to detect the signature of a specific crop for the purpose of analyzing the percentages of crop types in a given region.

In another aspect, the present invention may be used to detect the signature of a specific illegal crop, such as marijuana, opium poppy (heroine) or coca (cocaine). Such use of the present invention may benefit law enforcement when used for aerial inspection of a given region or for illicit crop documentation in a handheld device. Additionally, farmers may inspect their fields for unauthorized illegal crops planted in their fields, a practice commonly used by 'guerrilla' growers of illegal crops. The present invention is particularly well suited for this application in that it has the analysis power of conventional hyperspectral imaging at a great reduction in cost, and a significant increase in resolution over competitive hyperspectral imaging systems. The increase in resolution permits law enforcement to conduct surveillance from higher altitudes. A higher surveillance altitude reduces the risk from retaliatory shootings by illegal growers. A higher altitude, above 500 feet, also minimizes court challenges for violation of privacy, sometimes encountered by law enforcement when they conduct low-altitude surveillance.

Figure 16:
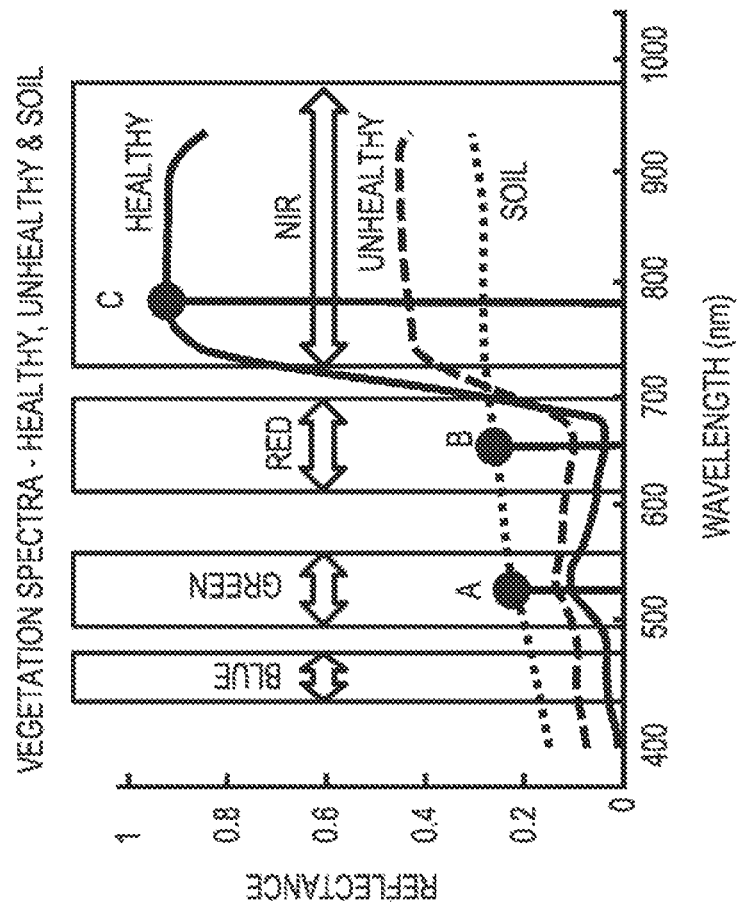
FIG. 16 shows spectral information illustrating selected wavelengths useful in the detection and analysis of a vegetation target substance.

FIG. 16 shows examples of spectra for healthy vegetation, unhealthy vegetation and soil. Three wavelengths (A, B, and C) are shown which enable the discrimination between the conditions. In the practice of the present invention, detecting information at these three wavelengths is enabled by using three camera and filter elements with a filter sensitivity centered around each of the designated wavelengths. In the example of FIG. 16, it is possible to determine if a given pixel represents soil or vegetation by computing the ratio of wavelength C to wavelength B, C/B. Those pixels with a C/B ratio above threshold (i.e., 2.0) represent vegetation while those pixel with a lower C/B value represent soil pixels. Only those pixels representing vegetation need be analyzed for vegetation health.

Vegetation Identification

In another aspect, the present invention relates to a method of identifying specific species of vegetation within the field of view. This application goes beyond the crop identification described above. Various species of vegetation have different spectral responses, making it is possible to identify many plant species via an analysis of their spectral response. Examples include, but are not limited to, tree species identification in a forest, crop species identification in an agricultural region, and grassland species documentation.

In another aspect, the present invention relates to a method to identify genetically modified organisms (GMO) where the genetic modification causes a change in the target spectrum as related to the unmodified organism (i.e., GMO corn or wheat detection).

Vegetation Mapping and Infestation Tracking

In another aspect, the present invention relates to a method to map a specific species of vegetation. For example, the present invention may acquire aerial data indicating the location of various tree species within a forested, rural, urban or suburban setting.

In another aspect, the present invention relates to a method to map a specific species of vegetation for the purpose of pest control. The present invention may acquire aerial data indicating the location of various tree species within a forested, rural, urban or suburban setting which are susceptible to infestation. For example, the location of ash trees may be determined which are susceptible to infestation by the Emerald Ash Borer beetle.

In another aspect, the present invention relates to a method to track pest infestation within a specific species of vegetation. For example, the present invention may acquire aerial data indicating the location of ash trees which are susceptible to the Emerald Ash Borer beetle and further analyze these data to identify damage to these same ash trees indicative of actual infestation. This is possible because the spectral characteristics of damaged trees would be distinct from that of healthy trees.

Soil Analysis

In another aspect, the present invention relates to a method to analyze soil. The spectra of various soils may be evaluated to determine the selected wavelengths that distinguish between the soil types of interest. Filter elements are then chosen that are sensitive to these selected wavelengths.

In another aspect, the present invention relates to a method to analyze the soil in preparation for crop planting and selection of fertilizer nutrients and dosage.

Disturbed Soil Detection

In another aspect, the present invention relates to a method to detect disturbed soil. The soil analysis capability described herein may be applied to a region of soil within the field of view. The target soil area is analyzed. Any digging in the soil is likely to leave traces, or large amounts of soil that was originally positioned at a depth below the surface. This variation in surface soil composition can be detected with the present invention and highlighted on a display of the soil analysis. Unnatural soil discontinuities may automatically be flagged as possible disturbed soil.

Applications of disturbed soil detection may include, but are not limited to: the detection of dangerous devices, at or below the soil surface, which are intended to harm nearby subjects; the detection of underground tunnels; the location of shallow graves or buried objects; the location of archeological artifacts and structures from past civilizations; and the early detection of illegal drug cultivation. Disturbed soil detection may also be useful in the management practices of mining, agriculture, and construction.

Cranberry Industry

Cranberries are a valuable crop for which the present invention has particular importance. While the total acreage of cranberries planted in the U.S. is a small fraction of other crops such as corn, soybeans or wheat, the per acre value of cranberries is much greater. The 2013 cranberry revenue was reported to be $9566 per acre in comparison to $960, $536 and $468 per acre for corn, soybeans and wheat, respectively. (See USDA Noncitrus Fruits and Nuts, 2012 Preliminary Summary, Jan. 1, 2013). Due to stringent wetland laws, cranberry growers find it difficult to expand their acreage to meet increasing demand for their product. Therefore, it is advantageous for cranberry growers to increase current crop yield in existing cranberry beds.

In one aspect, the present invention relates to a method to map cranberry fields for soil analysis, maturity tracking, disease detection, weed management, and harvest readiness. The high resolution of the present invention makes the present invention attractive where the lower resolution of conventional satellite and other conventional, remote sensing technologies fall short.

In another aspect, the present invention relates to a method to integrate a telephoto lenses into one or more spectral imaging element of a camera array. With this additional feature, a crop field can be scanned with even greater resolution. The use of telephoto lenses on the camera elements can be beneficial in many applications other than crop scanning where high resolution scanning from a distance is desired.

In another aspect, the present invention relates to a method to screen the harvested berries. Cranberries typically reach receiving stations with various grades of berry and numerous contaminants mixed with the product. Most cranberries are harvested by flooding the fields, vibrating the berries from the vines, and corralling the berries with floating booms towards the waiting harvest machines along the edge of the flooded field. The harvested cranberries may be white (unripe) and various shades of red. Rotten or bruised berries are also present. Since cranberry beds are sometimes adjacent to roadways, highway litter may end up at the berry processing plant in the form or paper, plastic, cigarette butts, and even metal particles embedded in the berries. These various berry conditions and contaminants each have different spectral signatures that can be used to differentiate them from the desired good berry. Used in conjunction with automated sorting machines, the present invention can provide a low-cost, high-resolution solution to the sorting needs of the cranberry industry.

In another aspect, the present invention relates to a method to provide a pre-screening system positioned adjacent to the cranberry fields during harvest that is low-cost, portable and of high-resolution. This pre-screening system would screen and remove defective berries and contaminants before loading on trucks for transport.

Inspection of Fruits and Vegetables

In another aspect, the present invention relates to a method to inspect produce, such as fruits and vegetables, for contaminants within a quantity of the produce or on the surface of the produce. Spectra of the desired fruit or vegetable are acquired and compared with acquired spectra of likely contaminants. Selected wavelengths of these spectra are analyzed as described herein to determine the presence of contaminants within a quantity of the produce or on the surface of the produce. This information may be provided in real-time to automated sorting equipment to remove the contaminant from the good produce.

In another aspect, the present invention relates to a method to inspect produce, such as fruits and vegetables, for quality, such as ripeness, maturity, bruising, rotten spots, mold, mildew or other imperfections. Spectra of the ideal produce are analyzed along with spectra of each imperfection. Selected wavelengths of these spectra are analyzed as described herein to determine the presence of produce imperfections. This information may be provided in real-time to automated sorting equipment to remove the imperfect item. In a similar manner various grades of the produce may be identified and sorted accordingly.

Inspection of Nuts, Seeds, Legumes and Grains

In another aspect, the present invention relates to a method to inspect nuts, seeds, legumes and grains for contaminants within a quantity of the product or on the surface of the product. Spectra of the desired nut, seed, legume or grain are acquired and compared with acquired spectra of likely contaminants. Suitable wavelengths of these spectra are analyzed as described herein to determine the presence of contaminants within a quantity of the product or on the surface of the product. This information may be provided in real-time to automated sorting equipment to remove the contaminant from the good product.

In another aspect, the present invention relates to a method to inspect nuts, seeds, legumes and grains, such as peanuts, walnuts, cashews, pecans, almonds, hazelnuts, chestnuts, acorns, pistachios, Brazil nuts, beechnuts, sunflower seeds, rice, pine nuts, ginkgo nuts, bunya nuts, macadamia nuts, garden or crop seeds, grass seed, wheat, rye, corn, soybean, barley, sorghum, canola, rape seed, oats, beans, and coffee, for quality, such as ripeness, maturity, bruising, rotten spots, mold, mildew or other imperfections. Spectra of the ideal produce are analyzed along with spectra of each imperfection. Selected wavelengths of these spectra are analyzed as described herein to determine the presence of produce imperfections. This information may be provided in real-time to automated sorting equipment to remove the imperfect item. In a similar manner various grades of the produce may be identified and sorted accordingly.

Robotic Harvesting of Fresh Produce

Robots have been developed to harvest delicate fresh produce crops. However, present machine vision technologies do not have the ability to effectively distinguish between ripe and unripe fruits and vegetables, nor can they reliably identify leaves, stems and branches. The present invention fills a serious need that exists for an economical, mobile, imaging system to provide the ability to reliably select ripe fruits and vegetables, as well as exclude leaves, stems and branches.

In another aspect, therefore, the present invention relates to a method to provide a machine vision tool that can distinguish between ripe and unripe fruits and vegetables. It can also differentiate between produce, leaves, stems and branches. By analyzing the spectra of each item the robot is likely to encounter, it becomes possible to determine the spatial position of each item within the robot's field of view. The filter card can be designed to provide each camera element with the appropriate wavelengths to identify the desired produce components. When compared to a similar, conventional hyperspectral imaging system, the low cost and high resolution of the present invention are advantageous for this application. The much lower data volumes of many embodiments of the present invention also facilitates easier real-time processing. In another aspect, the present invention relates to a method to provide the above features as a system that is not mobile, but stationary.

Biofilm Detection

A biofilm is any group of microorganisms on a surface. These adherent cells are frequently embedded within a self-produced matrix of extracellular polymeric substance (EPS). Biofilms may form on living and non-living surfaces and can be prevalent in many environments, such as, natural, industrial, agricultural and hospital settings. Biofilm EPS, often referred to in the common vernacular as slime, often is a conglomeration of extracellular DNA, proteins, and polysaccharides.

While the microorganisms that generate a given biofilm require a microscopic analysis to directly detect and identify the species, there is evidence that the chemical composition of the biofilm generated by a given species of microorganism may be unique and can be readily viewed by macroscopic spectral analysis. In a recent study two genera of microbial biofilms have been identified on a stainless steel surface which is commonly used in food processing systems via conventional hyperspectral imaging methods. Won Jun, Moon S. Kim, Kangjin Lee, Patricia Milner, and Kuanglin Chao, Assessment of Bacterial Biofilm on Stainless Steel by Hyperspectral Fluorescent Imaging, Sens. & Instrum. Food Qual., 2009, 3:41-48, DOI 10.1007/s11694-009-9069-1, http://afrsweb.usda.gov/SP2UserFiles/person/35964/2009JunEtAI3-1SensInstrumFoodQualSafety41-48.pdf, viewed Nov. 3, 2013. In this study hyperspectral imaging was used to successfully detect biofilms generated by *E. coli* O157:H7 and *Salmonella enterica* on stainless steel surfaces.

In another embodiment, the present invention relates to a method to detect a target substance that is a specific biofilm on a surface. A representative biofilm include films generated by microorganisms such as *E. Coli* or *Salmonella*. In this application a characteristic spectrum of the specific biofilm is obtained by conventional hyperspectral imaging methods or other spectral means. Then specific selected wavelengths are determined that identify the desired spectra. Filter elements passing the selected wavelengths are incorporated into the elements of the spectral filter array. A target algorithm is established to reliably detect the chosen target substance. The present invention acquires and processes a number of spectral images as described herein. Finally, custom color displays may be generated to highlight the presence of a given biofilm on a surface within the field of view of the system.

In the above manner, the present invention may be used as part of a sanitation process for inanimate surfaces to identify the presence of biofilms before, during or after sanitation of a surface in areas such as food services, food processing, meat processing, hospitals, clinics or any location where contamination by microorganisms is a concern.

In the above manner, the present invention may also be used to identify the presence of biofilms on biological surfaces such as skin, dental surfaces, intestinal surfaces, endoarterial surfaces or any other biological surface.

Numerous other surfaces and biofilm microorganisms are envisioned, beyond the examples above, in the application of the present invention and are hereby included.

Hand Washing—Food Safety

Hand washing is a vital component for any food safety program in such places as restaurants, fast food facilities, food preparation businesses, and food processing facilities. Historically, compliance was largely dependent upon training and the integrity of the individual employee. Even the use of food processing gloves does not assure sanitation unless the gloves are changed at appropriate intervals to avoid passing contaminants on the outside of the gloves. Recently, video cameras have been added as an enforcement tool which can confirm hand washing actions, but not results.

In another aspect, the present invention relates to a method to improve hand washing efficacy as part of a food safety program. In this role, the present invention may be designed to directly inspect the hands and alarm if contaminants are detected. In this manner, the present invention becomes a direct measurement tool to detect contaminants that impact food safety, strengthening the present strategies used for food safety.

Hand Washing—Infection Control

Hand washing is also a vital component for infection control programs in hospitals and medical clinics. Presently, compliance is largely dependent upon the training and the integrity of the individual medical employee.

In another aspect, the present invention relates to a method to improve hand washing efficacy as part of an infection control program. In this role, the present invention may be designed to directly inspect the hands and alarm if contaminants are detected. Common contaminants that are handled by medical personnel include blood, feces, urine, and bodily fluids, which are all readily detectible via the present invention. In this manner, the present invention becomes a direct measurement tool to detect contaminants that impact the spread of infection within a medical facility.

Egg Inspection

U.S. annual production of table eggs exceeds 90 billion eggs. While blood spots appear in less than 1%, this still results in many millions of eggs containing blood spots. In hatching eggs, the early detection of fertilization is important in order to remove unfertilized eggs that may harbor bacterial growth and contaminate the hatchery. Cracked eggs that enable bacteria to enter the egg are a concern for both table eggs and hatching eggs, including the spread of *Salmonella* to human subjects.

Conventional hyperspectral imaging systems have recently been used to inspect eggs for defects. Hyperspectral imaging has been shown to be valuable in screening eggs for early fertilization detection (0-3 days), blood spots, bad egg (bacteria), and air sack size using a hyperspectral camera sensitive to wavelengths from 400-900 nm. It was found not to be accurate for crack detection. "The hyperspectral imaging system appears capable of detecting developing hatching eggs by Day 3 of incubation at a 91% rate for white shell eggs, and an 83% rate for brown shell eggs. Blood spots in table eggs can readily be detected with at least a 90% accuracy rate. Cracked shells are difficult for the hyperspectral system to detect under typical conditions." D. P. Smith, K. C. Lawrence, and G. W. Heitschmidt, Detection of hatching and table egg defects using hyperspectral imaging, USDA, Agricultural Research Service, Russell Research Center, Athens, Ga., USA, www.cabi.org/animalscience/Uploads/File/Animal Science/additionalFiles/WPSAVerona/10938.pdf.

The application of the present invention to egg inspection offers significant advantages over the conventional hyperspectral imaging systems. The cost of a conventional hyperspectral system, approximately $150,000, may be reduced to under $5000 using principles of the present invention. The present invention is also capable of vastly improved resolution over a conventional hyperspectral imaging system. The improved resolution of the present invention is likely to improve the diagnostic performance for detecting the small, dendritic shape of blood spots within the egg and may even be capable of detecting cracks in the shell, a critical function that the conventional hyperspectral system cannot achieve. The size, mobility and weight of the present invention are also key advantages over the conventional hyperspectral imaging system.

In one aspect, the present invention relates to a method to inspect table eggs for defects such as blood spots, bacterial contamination and cracks.

In another aspect, the present invention relates to a method to evaluate hatching eggs for fertility and infertility, bacterial contamination, proper development, and cracks.

In another aspect, the present invention relates to a method to inspect eggs for fecal contamination on the surface of the shell since avian feces may contain *Salmonella* and *E. Coli*. The presence of feces on the egg surface may be a serious contaminant. In this aspect, the spectra of feces and the spectra of egg shell are analyzed to select the wavelengths to best discriminate between the two materials. The filter elements are chosen to pass the s wavelengths and the multi-camera images are analyzed to determine the presence of fecal contamination in a manner described herein.

In another aspect, the present invention relates to a method to evaluate the health of the embryo at various stages of development by applying an aspect of the medical imaging diagnostics described elsewhere in this specification.

In another aspect, the present invention relates to a remote, noninvasive means to evaluate the chemical composition within the egg by evaluating the spectral composition of light passing through the egg. In the case of a fertilized egg, the chemical composition may be spatially assigned to anatomical portions of the developing embryo in order to assess a health condition of the developing embryo. In the case of the unfertilized egg, this chemical composition may be used to assess the nutritional value of the egg. Additionally, the different chemical compositions of the air sack, albumin and yolk permits an estimation of volumes based on the spatial positions of these characteristics.

Bird Vision

Scientists have recently determined that many species of birds have near ultraviolet (NUV) vision receptors. J. Rajchard, Ultraviolet (UV) Light Perception by Birds: A Review, Veterinarni Medicina, 54, 2009 (8): 351-359. Humans have three types of cone photoreceptors covering the wavelengths of 400-700 nanometers, with occular media (cornea, lens) absorbing UV light, thus shielding the human retina from UV radiation. Many birds on the other hand have no occular absorbtion of NUV light and, in fact, have been found to possess 4-5 cone photoreceptors, including one type sensitive to NUV light in the range of 320-400 nm.

Avian subjects have been found to use their NUV vision in a number of ways. While in flight a kestrel can quickly identify areas with high rodent density by observing the UV light reflected from the frequent urine markings along vole (field mouse) trails. Crows have been found to prefer berries with high UV contrast against background. The zebra finch selects seeds based on NUV intensity. Numerous avian species have been found to select a mate based on the brightest plumage and markings, as viewed with NUV sensitivity. While some species, such as starlings, crows, and grackles, exhibit little male/female difference in plumage color as viewed with human vision, the male and female have remarkably distinct plumage color and markings when viewed with NUV vision. The beaks of juvenile (not adult) gentoo penguins are UV-reflecting, a possible aid to parents when feeding. The UV reflectance of supra-orbital combs on red grouse have been found to be an excellent indicator of health since this reflectance is greatly reduced in the presence of parasitic worms, though no change in comb size or condition is observable within the human range of vision. Birds also use their UV perception for recognition of their eggs. Similar eggs, as viewed with human vision, have remarkably distinct coloration and markings when viewed under UV light.

In one aspect, the present invention relates to a method to distinguish features of an avian subject using multi-camera/filter elements sensitive to ultraviolet (UV) or near ultraviolet (NUV) portions of the electromagnetic spectrum.

In another aspect, the present invention relates to a method to distinguish features of an avian subject using multi-camera/filter elements sensitive to any portion of the electromagnetic spectrum.

In another aspect, the present invention relates to a method to distinguish the sex of an avian subject based upon the ability to distinguish between male and female markings made visible by examining different parts of the electromagnetic spectrum.

In another aspect, the present invention relates to a method to distinguish the sex of a recently hatched avian or poultry subject, based upon the ability to distinguish between male and female markings made visible by examining different parts of the electromagnetic spectrum.

In another aspect, the present invention relates to a method to determine the sex of a recently hatched avian or poultry subject, based upon the ability to distinguish between male and female markings made visible by examining different parts of the electromagnetic spectrum. In this aspect, the present invention may be part of a machine vision system which detects the sex of the avian subject and enables a sorting step to separate male and female subjects.

In another aspect, the present invention relates to a method to determine the health of an avian or poultry subject, by examining different parts of avian anatomy using various portions of the electromagnetic spectrum.

Urine Detection

Urine detection is valuable in numerous fields. As an example, since rodents leave frequent urine markings, the present invention may be used by pest control experts to identify rodent trails and entry points as part of a pest control program. Hunters may use the present device in a similar manner to easily identify game trails and marking sites. Subtle differences in the spectra of urine samples may be useful to medical and veterinary technicians to detect chemical substances in the body.

In another aspect, the present invention relates to a method to derive information about urine within the target field of view. For example, an analysis of the urine absorption and reflectance spectra may be used to select a suitable number of filter elements and wavelengths to implement via an interchangeable filter array. In this application, suitable wavelengths are likely to be in the range between 200 nm and 400 nm.

In another aspect, the present invention relates to a method to analyze urine samples for medical and veterinary purposes.

Diabetic Foot Perfusion

Diabetic foot disease is a formidable problem due to both its complexity and the increasing diabetic population. Diabetes is the most common cause of non-traumatic, lower limb amputation with diabetics over 20 times more likely to undergo amputation than the general population. A key component of the disease is compromised peripheral perfusion. The imaging capabilities of the present invention described herein provide a valuable diagnostic tool in the battle against diabetic foot disease.

Diabetic Foot Vascular Imaging

In one aspect, the present invention relates to a method to image the health of the peripheral vessels of the lower limbs. The vascular imaging capabilities of the present invention described herein are a powerful tool which may be used to identify compromised arteries and veins of the lower limbs. Used in the reflectance mode, superficial vessels may be inspected. Used in the transmission mode, both superficial and deep vessels may be examined. In this aspect, the selected wavelengths are chosen to differentiate between arterial and venous blood. Vascular images and trees may be achieved for lower limb circulation. The low cost, small size, and mobility, coupled with the high-resolution imaging output, provide a device which can be available in physician offices and clinics. The widespread availability of this powerful technology, in mobile or stationary form, makes it a formidable tool.

Diabetic Foot Wound Diagnostics

In another aspect, the present invention relates to a method to image the health of tissue surrounding an ulcer or wound on the foot. The healing ability of an ulcer or wound is largely dependent upon the blood supply available. In this aspect, the selected wavelengths are chosen to differentiate between oxyhemoglobin and deoxyhemoglobin in the tissue surrounding the wound, much as pulse oximetry is used to determine the oxygen saturation of a finger. However, the present invention provides the ability to obtain and display a spatial map of this tissue oxygenation (rather than a single average measurement as in the case of pulse oximetry). Such a tool is useful both for an immediate evaluation of tissue perfusion surrounding the wound, and also as a benchmark comparison over a longer time period to evaluate progress of wound healing.

Figure 17:
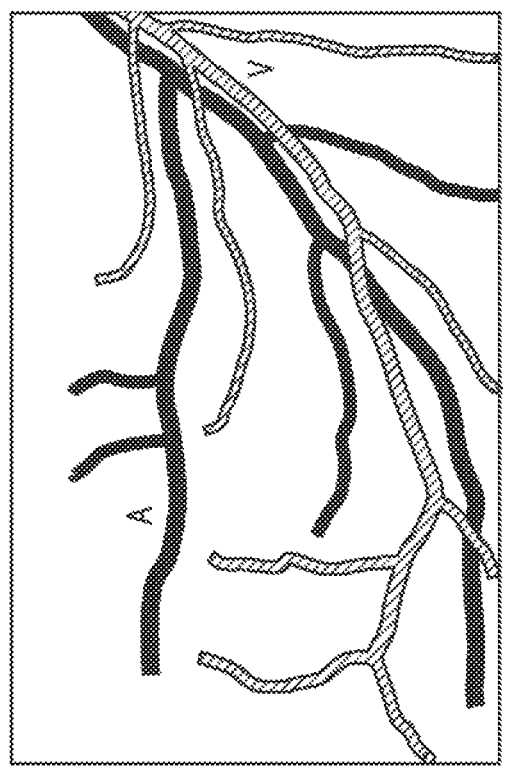
FIG. 17 shows a schematic of an output image of a human retina with differentiated arterioles and venules achieved due to the differences in spectral characteristics of oxyhemoglobin and deoxyhemoglobin that allow principles of the present invention to detect arterial/venous blood and measure oxygen saturation in a tissue.

For example, FIG. 17 shows a spectral image at 600 nm of a human retina showing arterioles and venules. The image at this wavelength shows the different vascular contrast due to the different absorption spectrum of hemoglobin varying according to oxygen saturation. Consequently, the arterioles and venules are easily distinguished. These images also may be color-coded. For example, arterioles could be shown as red, while venules are shown as blue.

In another aspect, the present invention relates to a method to provide a low-cost, mobile, high-resolution imaging system that may be made available to patients in physician offices, clinics and even as a capability of a personal smartphone or computing device. Stationary devices are also an option.

Peripheral Vascular Disease

General Peripheral Vascular Disease

In another aspect, the present invention relates to a method to diagnose peripheral vascular disease in general. The methods described for the diabetic foot may be expanded to include other peripheral vessels.

Feedback for Procedures Intended to Open Occluded Peripheral Vessels

In another aspect, the present invention relates to a method to provide immediate feedback for procedures intended to open occluded peripheral vessels. In this aspect the present invention may be used to spatially monitor tissue oxygenation within the field of view. A series of images, taken during the vascular procedure, can provide an efficacy record for the procedure. Provided as real-time still images, or a real-time video image, this feedback can be a valuable part of the procedure. As the occluded vessel is opened during the procedure, tissue oxygenation fed by the enhanced blood flow changes and may be viewed with the present invention. The change in tissue oxygenation may be used as an indicator of vessel occlusion during the procedure and in follow-up visits thereafter.

Wound Healing

A vital component in wound healing is the oxygenation of tissue surrounding the wound, which is a function of the gradual re-establishment of small blood vessels disrupted by the injury. Presently, this process cannot be accurately assessed without biopsies or transcutaneous techniques limited to a single point.

In one aspect, the present invention relates to a method to assess wound healing. The methods described for the diabetic foot and peripheral vascular disease may be expanded to include other wounds as well. The ability to quantitatively obtain a spatial oxygenation level, based on the spectra of oxygenated and deoxygenated hemoglobin, provides an immediately valuable diagnostic tool for clinicians. The ability to track changes in these spatial oxygenation images over time provides a quantitative measure of the healing progression that can identify normal healing as well as problems that may arise.

Feedback for Cardiopulmonary Resuscitation (CPR)

During cardiopulmonary resuscitation (CPR) a primary goal is to maintain brain oxygenation at a level sufficient to avoid brain injury or death. The techniques, methods, equipment, rescue personnel and patient condition are often less than ideal due to the emergency nature of the event. While the compression rate, compression duration, placement of the hands, and depth of compression are all critical factors in the successful administration of CPR, there is often little feedback to the rescuer regarding the efficacy of their technique. Throughout a CPR event, conditions change and the rescuer may become fatigued. The present invention offers immediate feedback to the rescuer during CPR, enabling the rescuer to optimize the technique based upon an immediate physiological measure of tissue perfusion resulting from the CPR methods.

In one aspect, the present invention relates to a method to provide efficacy feedback to a rescuer administering CPR. As a preferred embodiment in a human subject, the common carotid arteries provide blood flow to the brain via the internal carotid arteries and the circle of Willis, as well as blood flow to skin tissue in the forehead region via the external carotid and temporal arteries. Thus, the oxygenation level of forehead tissue may be used as an indicator of carotid blood flow during CPR and an indirect indicator of brain perfusion. Therefore, by monitoring the tissue oxygenation levels in the forehead region via the present invention, using the oxyhemoglobin and deoxyhemoglobin spectra described herein, a real-time, indication of brain perfusion during CPR may be obtained. Using the present invention in this manner, the rescuer may observe the perfusion effect resulting from any change in CPR technique, such as hand placement, depth of compression, compression rate, compression duration, or the like. Such real-time feedback permits a rescuer to monitor and adjust CPR technique to optimize carotid blood flow during a rescue session using the present invention aimed at a convenient, exposed surface on a patient, such as the forehead region. Other vascular beds may also be monitored as an indication of perfusion.

Cardiovascular Risk Assessment Via a Reactive Hyperemia Protocol

Cardiovascular disease is the leading cause of death in the United States and many developed countries. Non-invasive, low-cost methods are sought to screen asymptomatic, at-risk patients in order to identify those individuals who should undergo more sophisticated and expensive diagnostic tests to determine necessary treatments such as stents, systemic drug therapy, or vascular surgery. Present screening tests may include a transient brachial artery occlusion via an inflated cuff, followed by a reperfusion protocol, to measure reactive hyperemia. It is thought that the ischemia created by the temporary occlusion of the proximal artery triggers the release of nitric oxide (NO) from healthy endothelial cells within the arterial wall which in turn triggers a distal dilation of the microvasculature. The magnitude of the dilation response is an indication of the health of the endothelial cells within the artery. The release of nitric oxide is indirectly detected and measured using a number of sensors, including digital thermal monitoring (fingertip temperature), fingertip pressure, laser Doppler (skin perfusion), ultrasonic Doppler blood flow (radial or ulnar arteries), and skin perfusion pressure.

In one aspect, the present invention relates to a method to directly measure the release of nitric oxide (NO) during a reactive hyperemia protocol, by selecting wavelengths that are sensitive to the presence of NO to include via the filter array. In this manner, a cuff inflation/deflation protocol may be conducted while simultaneously having the distal region of the limb within the field of view of the present invention, thus recording a sequence of images that indicate the changing concentration of NO at the distal target site. The timing and magnitude of the nitric oxide curve detected at the distal site is indicative of the arterial reactivity and the health of the arterial system. The quantitative health of the arterial system is a strong indicator of a patient's cardiovascular risk.

In another aspect, the present invention relates to a method to measure the dilation within the capillary beds distal to the cuff during the occlusion/reperfusion protocol. In this aspect, the wavelengths of the filter array are selected to be sensitive to changes in the oxyhemoglobin and deoxyhemoglobin spectra as described elsewhere within this specification.

In this manner, the cuff inflation/deflation protocol is conducted while simultaneously having the distal region of the limb within the field of view of the present invention, recording a sequence of images that indicate the changing concentrations of oxyhemoglobin and deoxyhemoglobin at the distal target site. The timing and magnitude of the oxygenation curve within the blood, detected at the distal site, is indicative of the arterial reactivity and the health of the arterial system. The quantitative health of the arterial system is a strong indicator of a patient's cardiovascular risk.

Surgical Tool to Indicate Vascular Clamping

Researchers demonstrated the use of a modified hyperspectral imaging system to examine the spectral characteristics of oxyhemoglobin and deoxyhemoglobin to aid surgeons by monitoring the oxygenation status of tissue. Karel Zuzak, Robert Francis, Jack Smith, Chad Tracy, Jeffrey Cadeddu, and Edward Livingston, Novel Hyperspectral Imager Aids Surgeons, SPIE Newsroom, 2008, 0.1117/2.1200812.1394. In one aspect, the present invention also would be useful to monitor the spectral characteristics of blood components, such as, oxyhemoglobin and deoxyhemoglobin. Advantageously, the present invention provides a real-time, sequence of still or video images showing conditions of ischemia for tissue and organs that have had their blood supply restricted due to vascular clamping during surgery. In many modes of practice, spectral imaging systems of the present invention are small, light-weight, and economical. Additionally, the present invention provides higher resolution than many conventional hyperspectral imaging systems and can operate at a video rate, 30 images per second.

In another aspect, the present invention relates to a method to monitor and display the length of time that a given organ or region of tissue has experienced ischemia. This is accomplished by monitoring regions of the field of view and detecting a transition from an oxygenated to a deoxygenated condition. Additionally, the reverse transition is also detected. Upon detecting the former transition, "ischemic", a timer is initiated. When the latter is detected for the same region, "normal", the timer is stopped and the elapsed time recorded in memory. If multiple transitions between "ischemic" and "normal" are detected, displays may indicate: a) current ischemic time, b) cumulative ischemic time, and c) the number of times the target region was ischemic.

Lymphatic Imaging

Sentinel lymph node (SLN) mapping is currently the standard of care for staging breast cancer. J. Sven D. Mieog, Susan L. Troyan, Merlijn Hutteman, Kevin J. Donohoe, Joost R. van der Vorst, Alan Stockdale, Gerrit-Jan Liefers, Hak Soo Choi, Summer L. Gibbs-Strauss, Hein Putter, Sylvain Gioux, Peter J. K. Kuppen, Yoshitomo Ashitate, Clemens W. G. M. Löwik, Vincent T. H. B. M. Smit, Rafiou Oketokoun, Long H. Ngo, Cornelis J. H. van de Velde, John V. Frangioni, and Alexander L. Vahrmeijer; Toward Optimization of Imaging System and Lymphatic Tracer for Near-Infrared Fluorescent Sentinel Lymph Node Mapping in Breast Cancer; Annals of Surgical Oncology, 201110.1245/s10434-011-1566-x. Typically, a combination of radioactive colloid and blue dye is injected into the lymphatic system to provide the necessary contrast. However, this exposes the patients and caregivers to ionizing radiation and blue dyes cannot be seen through skin and fatty tissue. Recent clinical data indicate that near-infrared (NIR) fluorescence imaging, using the NIR fluorescence agent indocyanine green (ICG), enables real-time transcutaneous visualization of lymphatic channels and detection of SLN without the risk of ionizing radiation to patient and caregivers. The first generation of equipment, FLARE, to utilize this approach was deemed too large and cumbersome to distribute to clinicians. The second generation, mini-FLARE, reduced the weight to 272 pounds, including a 95 lb. arm and an 8.8 lb. imaging head. This mini-FLARE system is still large, heavy and expensive. While the shortcomings of the imaging system are significant, the images obtained are powerful and provide the clinician with diagnostic information previously available only with radioactive colloid. The present invention provides an alternative way to achieve the sentinel lymph node mapping using NIR fluorescent dye (no radioactive colloid required) without the expensive FLARE (heavy, unspecified weight) or mini-FLARE (smaller, 272 lbs.) equipment.

In one aspect, the present invention relates to a method to provide sentinel lymph node mapping using NIR fluorescent agents in place of the commonly used radioactive colloid and blue dye. With an economical, handheld size and weight of under one pound, the present invention provides a means to achieve the desired SLN mapping using fluorescent dye without the significant disadvantages of the cumbersome and expensive, mini-FLARE, system that weighs 272 lbs.

Lymph Node Surgery

Researchers demonstrated that an NIR fluorescence detection system is helpful to surgeons in the surgical removal of a fluorescence-labelled lymph node from the neck of a rabbit. Heuveling D A, Visser G W, de Groot M, de Boer J F, Baclayon M, Roos W H, Wuite G J, Leemans C R, de Bree R, van Dongen G A—Eur. J. Nucl. Med. Mol. Imaging (2012). Under normal surgical lights, the boundaries of a lymph node are not well defined. However, with fluorescent labeling and lighting the boundaries are easier to see.

In one aspect, the present invention may be used for NIR fluorescent dye detection to aid in the surgical removal of lymph nodes. Dye is deployed in a patient in a conventional manner such that lymph node tissues selectively incorporate the dye. A system of the present invention can be used to capture images of the patient through filters that allow the lymph nodes to be distinguished from other tissues. Analysis of the captured images allows the lymph nodes to be identified and located with high precision. For example, the present invention can provide a color-coded image showing the boundaries of lymph nodes as color-coded highlights layered on a color or grayscale spatial reference image. This color-coded image would provide significant definition of the lymph node boundaries—a critical component in surgical removal of the node. The fluorescent dye coupled with the principles of the present invention provide the high contrast necessary to enhance the boundaries of the lymph node to aid in surgical removal.

Peripheral Artery Disease (PAD)

Peripheral artery disease (PAD) is a disease of the circulatory system characterized by reduced flow to limbs due to a narrowing or blockage of the arteries.

In one aspect, the present invention relates to a method to diagnose and monitor treatment of PAD when the present invention is used in one or more of the following ways that have been previously described:

a) to evaluate a patient's cardiovascular risk via a reactive hyperemia protocol, such that an indication of the health of the endothelial cells, lining the walls of an artery, is determined;

b) to evaluate the oxygenation of a tissue region distal to an artery, similar to evaluating the oxygenation near a wound, in order to evaluate the peripheral perfusion effects of PAD;

c) to image the vascular tree in the periphery, such as was described previously, to identify narrowing or occlusion of the vessels via a non-invasive, economical technique;

d) to monitor the progress and effect of an invasive protocol such as balloon angioplasty, endarterectomy (i.e., scalpel, ultrasound catheter, orbital atherectomy) both during the procedure and during the weeks and months following the procedure.

Breast Cancer Detection

Researchers presented absorption spectra for a 30-mm diameter tumor in the breast of a chemotherapy subject and spectra for normal breast tissue that shows a significant spectral difference between normal tissue and a tumor. Cerussi A, Hsiang, D., Shah, N., Mehta, R., Durkin, A., Butler, J Tromberg, B., Predicting Response to Breast Cancer Neoadjuvant Chemotherapy Using Diffuse Optical Spectrscopy, Proc. Natl. Acad. Sci. U.S.A., 104: 4014-4019, 2007. The heightened absorption for the tumor, as shown in FIG. 2E, is a result of increased hemoglobin and water in the region of the tumor with respect to normal tissue.

In one aspect, the present invention relates to a method to detect tumor tissue in a breast as compared to normal breast tissue. In such an application, the heightened absorption in the region of the tumor, due to the increase in hemoglobin and water, can be differentiated from that of normal breast tissue. In such an application, the selected wavelengths determined by an analysis of the respective spectra, will be sensitive to the spectral differences of the two tissue types as displayed in FIG. 2E.

Skin Cancer Detection

As there are different spectral characteristics for tumor and normal breast tissues, it is anticipated that there are similar spectral differences for cancerous and normal skin tissues.

In another aspect, the present invention relates to a method to detect skin cancer by detecting the spectral differences between the spectra of cancerous and normal skin tissues in a manner consistent with the description of the present invention.

Medical Imaging

Medical applications of spectral imaging using ultraviolet, visible, near infrared and infrared imaging methods are numerous. Examples of these applications include blood flow detection, tissue perfusion, location of arteries and veins, urine tests, skin diagnostics, estrus detection, tumor detection, lymphatic system imaging, and lymph node surgery. These methods may be used using the spectral characteristics of blood, tissue, and bodily fluids independently and in conjunction with fluorescent dyes. To date most of these applications require dedicated equipment that is large, expensive and immobile. There is great need for the present invention in these applications, providing an economical solution with improved performance and greater mobility. Even small stationary devices offer great advantage over the large, cumbersome size of many medical imaging systems.

In one aspect, the present invention is related to a method to provide a medical image of a patient using one or more of the spectral characteristics present within the target field of view and the methods of the present invention described herein.

In another aspect, the present invention is related to a common medical imaging platform which may be used for different specific imaging applications by simply interchanging a filter card and loading the appropriate algorithm from electronic memory. The present invention permits a hospital or clinic to cost effectively meet numerous medical imaging needs with a common instrument platform and a library of filter cards (and associated software algorithms) instead of expensive, dedicated imaging systems for each application.

Medical Diagnostic Information Automatically Linked to an Individual Subject

In another aspect, the present invention relates to a method to acquire and analyze multi-camera data of an individual animal or human within a target field of view, simultaneously acquiring a unique individual identification, and entering the multi-camera data into a database organized according to the individual human or animal. The individual identification may be, but is not limited to, a radio frequency identification (RFID), bar code, patient identification bracelet, manual identification number, or hospital patient record number.

Veterinary and Human Applications

Since animal physiology and human physiology are in many ways similar or identical, the medical applications described herein also apply to similar veterinary applications. Likewise, veterinary applications may readily be adapted for human use. Veterinary applications include, but are not limited to, mammalian applications for small animals, livestock, and companion animals, aquatic animals, as well as avian or poultry applications. The common physiological characteristics permit a universal application across many species.

In one aspect, the present invention relates to a method to apply novel spectral imaging methods to both animals and humans utilizing their similar anatomical and physiological characteristics.

Estrus Detection

Dairy Management

The accurate and efficient detection of estrus for dairy cows is essential for a quality breeding program and the economical management of a dairy herd. The most widely used indicator of estrus, or heat, is the manual observation of when a cow permits herd mates to mount while she remains standing. This surveillance of mounting activity is labor-intensive and expensive. Present precision dairy technologies rely largely on behavior-based, indirect indicators of estrus such as rumination detectors (narrow-band microphones) and activity sensors (accelerometers).

One direct, physiological sign of estrus is a blood-swollen vulva, triggered by the increase in estrogen at the onset of estrus. A vaginal, mucus discharge is also common and frequently smears on the rump and tail. Chemical changes, due to hormonal stimulation, occur in bodily fluids such as urine, blood, vaginal mucus, saliva, nasal discharge, feces and tears.

In one aspect, the present invention relates to a method to indicate estrus by detecting an increase in blood flow to the vulva by sensing the oxygenation level of vulvar tissue in a manner similar to that described for observing tissue oxygenation for the diabetic foot or the tissue surrounding a wound. This method uses wavelengths sensitive to oxyhemoglobin and deoxyhemoglobin to evaluate tissue oxygenation. A threshold may be established to differentiate between vaginal tissue oxygenation levels during estrus and vaginal tissue conditions at other times during a reproductive cycle.

In another aspect, the present invention relates to a method to indicate estrus by detecting chemical changes in bodily fluids, such as urine, blood, vaginal mucus, saliva, nasal discharge, feces and tears. This method uses wavelengths sensitive to the specific chemical change of a given bodily fluid during estrus.

In another aspect, the present invention relates to a method which may be used in a milking parlor or feed area to automatically scan individual cows each time they come into the area. Reproductive data acquired in this manner is available for inclusion in an animal data base with the identify of the individual animals detected by automated animal identification methods, such as RFID, or manually entered into the system. In this manner, statistical analysis of these reproductive data may be used to closely track the reproductive cycle of an individual cow to predict the optimal time for breeding.

In another aspect, the present invention relates to a method to provide a portable, hand-held device which may be used by dairy managers to manually scan individual cows anywhere on the farm and at any time. Reproductive data acquired in this manner is also available for inclusion in a dairy data base. Individual cows may be identified by either automated or manual identification methods. Statistical analysis of these reproductive data may be used to closely track the reproductive cycle of an individual cow to predict the optimal time for breeding.

In another aspect, the present invention relates to a method to determine the health of an individual cow. The reproductive data and chemical analysis of bodily fluids, acquired in the manners described above, may be further processed to detect trends and variations which are indicative of the health of the individual animal. The combined health of individual animals may be collectively analyzed to monitor the health of the entire herd.

Livestock Management

The detection of estrus as part of a livestock breeding program is critical. As with dairy cows, (described above) the detection of estrus in other livestock, such as beef cattle, pigs, goats, sheep, horses, bison, deer, elk, camels, llamas, and donkeys, is often accomplished, with varying degrees of efficiency, by labor-intensive observation. The dairy applications of the present invention, described above, may be readily adapted for any number of other animal species.

Forensics and Criminology

In another aspect, the present invention relates to a method to detect forensic substances such as bodily fluids, fingerprints, gunshot residue, and bruise enhancement. Spectra of the desired target substance and anticipated background substances are analyzed and critical wavelengths selected. Filter elements are chosen according to the selected wavelengths. The present invention may be particularly advantageous in outdoor settings where present technologies require light-blocking structures and expensive, narrowband, bulky, light sources, since the present invention may detect the target substance using natural, broad-spectrum sunlight. Additionally the present invention is advantageous since it can directly detect forensic substances without the use of fluorescent sprays, such as Luminol for blood detection, which may dilute or otherwise degrade the forensic substance of interest.

In another aspect, the present invention relates to a method to combine the filter elements necessary to detect multiple forensic target substances in a single filter card (as an alternative, electronic tunable filters may be used). For example, a single filter card may contain all the necessary filter elements for selected wavelengths necessary to detect blood, semen, and gunshot residue. When using such a combination filter card, program instructions are combined to provide the algorithm to detect and display each target substance. As an example, a single grayscale, spatial orientation image of a crime scene may be displayed with blood highlighted in red, semen highlighted in white, and gunshot resident highlighted in blue. Obviously, other color schemes are possible and are included, herein.

Building Inspection

Building inspections presently rely highly on visible observations or thermal cameras (long wave infrared, 8 µm to 14 µm). While thermal cameras provide an indication of moisture due to evaporative cooling, they lack the ability to indicate damage that has achieved the same temperature as its surrounding. Thermal cameras also lack a capability for chemical analysis, are low-resolution and typically lack the connectivity, via internet or cell phone system, of the present invention.

In another aspect, the present invention relates to a method to detect building damage via chemical signatures characteristic of moisture, mold, mildew, smoke, pet urine, and pest infestation (rodents, cockroaches, termites, scorpions, bedbugs, spiders, stink bugs, carpenter ants, etc.). Each of these defects is characterized by chemical substances within the building that may be invisible to the human eye. Spectra of the desired target substance and anticipated background substances are analyzed and wavelengths selected. Filter elements are selected according to the selected wavelengths as described previously. As an example, a urine reflectance spectrum is characterized by a reflectance peak in the ultraviolet range near 375 nm with minimal reflectance around 450 nm. These urine characteristics may be used with the present invention to view pet urine stains on walls and carpet, rodent trails highlighted by urine markings, insect trails indicated by urine marks visible with the present invention, but not the unaided human eye. Similarly, the present invention may be used to detect the characteristic, vegetative spectra of mold and mildew where only inanimate surfaces should exist. Walls infested with rodents, carpenter ants, or termites may exhibit a combination of urine and moisture spectra.

Floor Cleaning

In another aspect, the present invention relates to a method to detect pet urine, mildew, smoke, mold or other contaminant on floors and carpets as part of a cleaning procedure or operation.

Pest Control

Pest control experts face a multitude of pest species and habitats with few diagnostic tools. Optical assistance is typically limited to an ultraviolet, fluorescent tube ('black light wand') and perhaps orange goggles (to filter out excessive UV light which may obscure the target and damage the eyes).

In another aspect, the present invention is related to a method to detect pest signatures. For example, the present invention may be used track rodent urine trails, identify fluorescent scorpions (UV), and detect blood residue from a bed bug infestation under normal outdoor or incandescent light conditions. The characteristics described herein regarding building inspection damage may be used to identify, track and exterminate pests as well as indicate the effectiveness of such treatment. Additionally, the smartphone interface of the present invention provides a convenient means to immediately communicate an instantaneous chemical analysis of an infestation scene to company experts for review and guidance.

Automotive

Leaks in automotive systems are commonly detected by placing ultraviolet dyes in the liquid or gas such that the leak fluoresces when exposed to ultraviolet light. In this manner a leaking substance, such as coolant, freon, engine oil, or brake fluid may be readily detected. Presently such ultraviolet dyes require low light conditions and a black light wand.

In another aspect, the present invention is related to a method to view the spatial distribution of ultraviolet dyes which provide a mapping of the automotive system leaks. Using the present invention these leak tracers may be viewed under normal daylight conditions, incandescent lighting or custom LED light sources. Since the spectral characteristics of a given line of UV dye is readily specified, the necessary filter elements may be provided on a standard filter card and the specific algorithms stored in a data table for easy access.

In another aspect, the present invention is related to a method to view leaks in other systems, such as robotic or hydraulic systems, using the methods described above for automotive systems.

Fluorescent Dyes

There is a large and growing market in fluorescent dyes. Applications include automotive fluid leaks, oil pipeline leaks, biophotonics (medical), nano technologies, industrial tracking and many others. One source, Crysta-Lyn Chemical Company, advertises over 800 "proprietary NIR, fluorescent, UV and laser dyes."

In another aspect, the present invention is related to a method to view fluorescent dyes in numerous applications. The spatial distribution of these dyes within the field of view and even their concentration may be provided with the methods of the present invention. The low-cost, high resolution and daylight viewing of the present invention provide an advantageous enhancement to the use of these fluorescent dyes.

Food Inspection and Processing

Some applications of hyperspectral imaging are coming to fruition in the food industry. The capability to obtain a real-time chemical analysis of food products on a conveyor belt is powerful. However, the many shortcomings of conventional hyperspectral imaging, such as high cost ($100,000-$200,000 per camera system), low resolution, linear scanning and large installation size, remain constant obstacles to widespread use within the food industry. A strong need exists for an economical imaging system that provides many of the benefits of hyperspectral imaging while overcoming the shortcomings.

In one aspect, the present invention is related to a method to inspect foods within the food industry. The target spectra of individual foods may be acquired as described herein. These spectra are then analyzed to select the wavelengths necessary to detect or measure the desired food property. The elements of the filter array are chosen to pass the selected wavelengths such that each image of the multi-camera array represents a different wavelength image. These images are then aligned and analyzed to detect or measure the desired food property as described herein. Examples of food industry applications include, but are not limited to, adulterant screening, fresh produce quality control (bruising, ripeness detection), grain screening, legume screening, screening for feces materials, insects, and bacteria (the biofilms associated with some strains of *Salmonella* and *E Coli* are UV fluorescent), moisture control, ingredient control, mixture controls, raw component screening, equipment sanitation, and packaging quality control. Numerous food safety issues can also be addressed with the present invention.

Mineral Detection and Processing

Hyperspectral imaging is presently in use for screening and processing minerals. The capability to obtain a real-time chemical analysis of various mineral and ore products on a conveyor belt is powerful. However, the many shortcomings of conventional hyperspectral imaging, such as high cost ($100,000-200,000 per monitoring station), low resolution, linear scanning and large installation size, remain constant obstacles to widespread use within the mining industry. A strong need exists for an economical imaging system that provides many of the benefits of conventional hyperspectral imaging while overcoming the shortcomings.

In one aspect, the present invention is related to a method to inspect gems and minerals, such as within the mining industry. The spectra of individual gem, mineral and ore properties may be acquired as described herein. These spectra are then analyzed to select the wavelengths necessary to detect or measure the desired mineral property. The elements of the filter array are chosen to pass the selected wavelengths such that each image of the multi-camera array represents a different wavelength image. These images are then aligned and analyzed to detect or measure the desired mineral property as described herein.

Examples of mineral industry applications include, but are not limited to, rapid analysis of drill cores, with SWIR and LWIR imaging of value for the detection of minerals in the feldspar, silica, calcite, garnet and olivine groups. Many mineral deposits are presently identified from airborne hyperspectral images. Such examples include minerals associated with the presence of gold and diamonds. The relationship between oil and natural gas leaks on the spectra of nearby vegetation is becoming better understood as a tool to detect leaks near pipelines and natural gas wells. The present invention makes use of spectral information and understanding available from conventional hyperspectral systems, in order to provide a tremendous reduction in system cost as well as a great increase in resolution, thus providing a higher performance system at a dramatic reduction in cost.

In another aspect, the present invention is related to a method to rapidly analyze drill cores using methods described herein.

In another aspect, the present invention is related to a method to sort gems and minerals on a mechanical conveyance, such as a conveyor belt, using methods described herein.

In another aspect, the present invention is related to a method to replace conventional hyperspectral imaging systems in the mineral industry with greatly reduced equipment cost and significantly improved resolution using methods described herein.

In another aspect, the present invention is related to a method to detect pipeline leaks by recognizing changes in the spectra of vegetation affected by the leaking pipeline product.

Frac Sand

Frac sand is a material greatly needed within the oil and gas industries to efficiently extract oil and natural gas from new wells using induced hydraulic fracturing techniques. There is a need to prospect for new frac sand deposits as well as screen the quality and moisture content of the frac sand during the processing stages.

In one aspect, the present invention relates to a method to derive information about frac sand within the target field of view. Frac sand, with a high composition of quartz, exhibits a broad reflectance amplitude in the spectral range from 400 to 1100 nm. An analysis of the frac sand reflectance spectra may be used to select a necessary number of filter elements and wavelengths to implement via the interchangeable filter array.

In another aspect, the present invention is related to a method to prospect for new frac sand deposits from a ground-based or airborne platform.

In another aspect, the present invention is related to a method to analyze the quality and moisture content of frac sand during the processing of the sand.

In another aspect, the present invention is related to a method to analyze the quality and moisture content of all sands types in a manner described herein for frac sand.

Feed Inspection and Analysis

The present invention is ideally suited for numerous applications in the feed industry, such as for livestock, poultry, pets, aquatic animals and the like. Quality assurance, sorting, analysis, incoming inspection of raw ingredients, mixtures and many more uses are valuable applications for the present invention. Significant value may be realized where the reflectance or absorbance spectra can be characterized and used to differentiate or measure a feed substance within the target field of view.

In one aspect, the present invention relates to a method to analyze or detect a feed substance within the target field of view using the methods described herein.

In another aspect, the present invention relates to a method to analyze feed to detect mycotoxins and aflatoxins, measure crude protein, analyze nutrients, and detect contaminants, including pesticides.

In another aspect, the present invention relates to a method to analyze feed to detect antibiotic residue.

Security and Forgery Detection

Genuine U.S. Federal Reserve Notes, such as denominations $5, $10, $50 and $100, have vertical security threads that fluoresce a unique color when illuminated with ultraviolet (UV) light. U.S. Treasury checks also contain inks that fluoresce under UV light. Secretive chemical markers ("virtual fingerprints"), not fully visible to the naked eye, may be used as anti-counterfeiting, brand protection, and product authentication measures for a multitude of U.S. and international products, such as currency, checks, banknotes, cigarettes, alcohol, pharmaceuticals, consumer goods, high-technology equipment, fuels, and energy products.

In another aspect, the present invention is related to a method to view the security threads and security markings on genuine U.S. Federal Reserve Notes and U.S. Treasury checks, containing features that fluoresce under UV light. The present invention may readily be applied to this application by analyzing the reflectance spectra of such documents, then selecting UV wavelengths that indicate the document properties. The filter elements are chosen to generate images representative of the selected wavelengths. After alignment, these images are analyzed to provide an indication of the genuineness of the document under inspection. The advantages of the present invention include a light-weight, mobile instrument that can view such security features under incandescent or outdoor lighting conditions. This application may be expanded to detect other types of security markings, anti-counterfeiting measures, brand protection methods, and product authentication criteria for many different products.

A secretive chemical or physical marker, which may be referred to as a taggant, may be added to materials and products to permit the material or products to be clearly identified by detection analysis. Such markers, often in the form of microscopic particles, may be added to the material at manufacture so as to identify the material and perhaps even the brand, formula, concentration and lot number of that material. Product examples that may contain taggants are inks, papers, glass, perfumes, polymer resins and products fabricated therefrom, official documents, money, fertilizer, chemicals, paint and varnish coatings, packaging, tires, composites, combustible or highly reactive materials, pharmaceuticals, alcohol, luxury products, and the like.

In another aspect, the present invention relates to a method to detect and identify specific security markers or taggants based upon their spectral characteristics. Such markers, comprised of microscopic particles or otherwise, may be selected to have specific spectral characteristics, in either reflective or absorptive modes, such that these spectral characteristics may be viewed using the present invention. The present invention may readily be applied to these applications by analyzing the reflectance spectra of materials containing such identifying markers, then selecting wavelengths that indicate the spectral properties of the markers. The filter elements are chosen to generate images representative of the selected wavelengths. After alignment, these images are analyzed to provide an indication of presence and/or quantity of the markers under inspection. The advantages of the present invention include an economical, light-weight, mobile instrument that can view such taggant features under artificial, incandescent or outdoor lighting conditions. This application may be expanded to detect other types of security markers and indicators.

In another aspect, the present invention relates to a method to view and identify specific taggants placed in inks, paints, or the like, such that invisible printing or coded printing which is not fully visible to human vision, may be viewed or decoded using the present invention. With the present invention, such printing systems could be used to create any number of secure and encoded documents, product labels, symbols, security markings and the like. Additionally, once the taggant printing or markings are identified using the present invention, machine vision methods for pattern recognition, imaging processing and the like may also be applied to provide a wide array of security systems and markings.

Hunting

In their quest for game, hunters may use the urine marking of their prey. On occasion hunters also need to follow blood trails of an animal. Additionally, since prey such as deer and avian subjects may be able to see hunter clothing that reflects ultraviolet (UV) light, hunters have a need to view the appearance of their clothing with respect to UV visibility.

In one aspect, the present invention is related to a method to detect and display the urine markings of prey animals so that a hunter may better track the prey using the differences between the spectral characteristics of urine and the spectral characteristics of background vegetation.

In another aspect, the present invention is related to a method to display a blood trail of an injured animal using the differences between the spectral characteristics of blood and the spectral characteristics of background vegetation.

In another aspect, the present invention is related to a method to display a hunter's clothing as it might appear to a prey animal that can see UV light reflected from the clothing.

Consumer Color Matching

Consumers often desire to precisely match colors. These colors may be paint colors on surfaces such as walls, ceilings, floors, cars, or any number of other objects. Additionally, these colors may involve articles of clothing such as shirts, coats, hats, scarves, shoes or other clothing accessories.

In one aspect, the present invention is related to a method to precisely match a color, such as paint or clothing, by recording spectral data at selected wavelengths in order to quantitatively describe an unknown color which the user desires to match.

Ultraviolet Tattoos and Body Art

Ultraviolet tattoos and body art have become popular. Invisible to the naked eye, these works of art use paints and dyes which are visible only under UV light.

In one aspect, the present invention is related to a method to match colors used for UV tattoos and body art by recording spectral data at selected wavelengths in order to quantitatively describe an unknown UV color which the user desires to match.

In another aspect, the present invention is related to a method to view UV tattoos and body art by recording spectral data at selected wavelengths in order to detect and display the UV artwork.

Gas Detection

A gas detector is a device which identifies the presence of various gases within an area. It may be handheld, battery-powered, or part of a safety system. Gas detectors may be used to detect combustible, flammable, or toxic gases. They may be used to detect a specific gas or a combination or mixture of gases. These type of devices are valuable in a multitude of applications, such as oil rigs, gas pipelines, industrial exhaust monitoring, manufacturing, homes, automotive systems, agricultural facilities and medical respiratory systems.

In one aspect, the present invention is related to a method to detect a chosen gas within an area. Using the methods described herein, the unique qualities of the gas spectrum may be used to identify the presence of the chosen gas within the target field of view and display the gaseous cloud as a color-coded presence on the output display.

In another aspect, the present invention is related to a method to detect the concentration of a chosen gas within an area. An in-frame reference, desirably positioned at a known distance from the imaging system, can be used to help calibrate image information to allow quantity information to be derived from the captured image information. For example, spectral properties for a substance may be a function of the concentration of the substance. The in-frame reference may include samples including the substance at known concentrations. Using the methods described herein, the unique qualities of the gas spectrum may be used to first identify the presence of the gas within the target field of view and then display the gaseous cloud as a color-coded presence on the output display in a manner that coveys the concentration of the gaseous cloud.

The application of the present invention to gas detection is valuable with or without the described display.

Petrochemical

Spectral imaging has numerous applications in the petrochemical industry. Vegetation changes caused by pipeline leaks have been previously described. Oil spill residue from any source, in water, soil or along shorelines may be detected by spectral variations.

In one aspect, the present invention relates to a method to detect oil residue in water, soil or along shoreline using the methods described herein.

Chemical Processing

The present invention is ideally suited for numerous applications in the chemical processing industry. Quality assurance, sorting, analysis, incoming inspection of raw ingredients, mixtures and many more uses are valuable applications for the present invention. Significant value may be realized where the reflectance or absorbance spectra can be characterized and used to differentiate or measure a chemical substance within a target field of view.

In one aspect, the present invention relates to a method to analyze or detect a chemical substance within the target field of view using the methods described herein.

Manufacturing

The present invention is ideally suited for numerous applications in manufacturing plants. Quality assurance, sorting, analysis, incoming inspection of raw ingredients, mixtures, assemblies, product security markings and many more uses are valuable applications of the present invention. Significant value may be realized where the reflectance or absorbance spectra can be characterized and used to differentiate or measure a target substance on a surface or within the target field of view.

In one aspect, the present invention relates to a method to analyze or detect a target substance within the target field of view using the methods described herein.

Sustainability

In another aspect, the present invention relates to a method to provide indicators for "sustainability" plans prepared for a government entity (i.e., federal, state, city, county, township) or a corporate/business entity. Such an indicator may involve a measure of water quality, aerial measurements of land use, the health of wetlands and forests, as well as the location of specific species of vegetation. Additionally, these sustainability indicators may include, but are not limited to, pest infestation, water pollution, chemical runoff, chemical spills, building code adherence, and adherence to watering bans.

Machine Vision

The present invention is well suited for numerous applications in machine vision. Objects within the target field of view may be identified by their chemical composition, as described herein. This object information may then be applied to many machine vision uses.

In one aspect, the present invention relates to a method to identify substances within the field of view by their spectral composition in a manner that serves as input into a machine vision system using the methods described herein.

Meat and Poultry Processing

In addition to similar uses described for food processing, meat processing applications also include meat quality control and lean meat vs. fat identification and grading. Recently, conventional hyperspectral imaging has been conceptually shown by the USDA to be capable of detecting organic material residue on meat processing equipment after cleaning. Conventional hyperspectral imaging also shows promise as a means of grading cuts of meat. As with food processing, this practical application of hyperspectral imaging is severely limited by the large, low-resolution, costly equipment essential for hyperspectral imaging. There exists a need for a reduced size, low-cost, imaging system that overcomes the significant limitation of conventional hyperspectral imaging for these applications.

Figure 18:
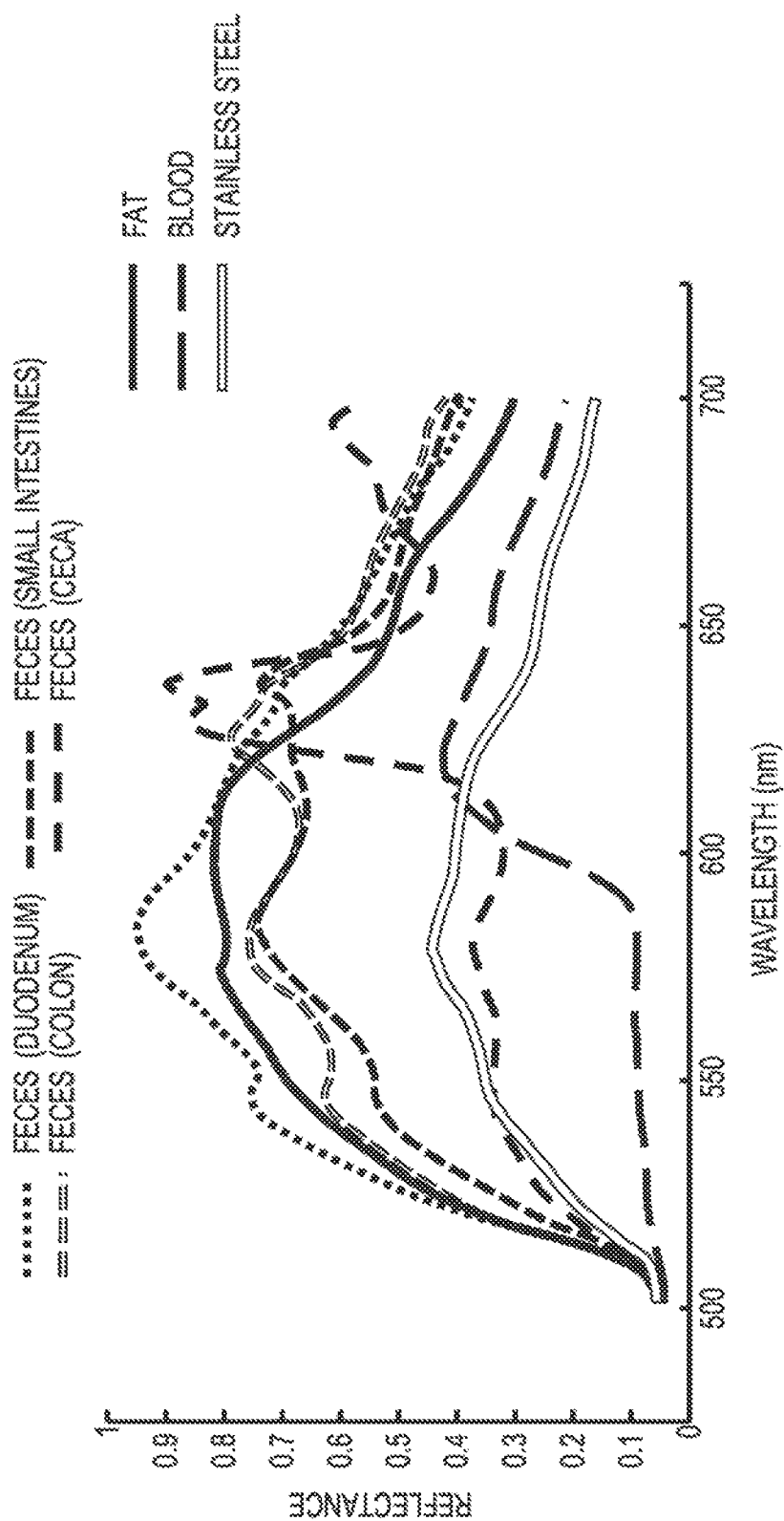
FIG. 18 shows how the spectral information for organic contaminants are distinguished from the spectral information of a stainless steel surface.
Figure 19A:
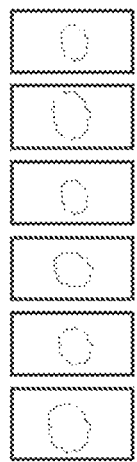
FIG. 19A shows a schematic image of a contaminated, stainless steel surface.

The present invention can fill this need. FIG. 18 shows spectral information for various contaminants that may be present on the surfaces of stainless steel processing equipment. The data is redrawn after: J. Qin, K. Chao, M. S. Kim, S. Kang, B. K. Cho, W. Jun, Detection of Organic Residues on Poultry Processing Equipment Surfaces by LED-Induced Fluorescent Imaging, Applied Engineering in Agriculture, American Society of Agricultural and Biological Engineers ISSN 0883-8542, Vol. 27(1): 153-161, 2011. http://naldc.nal.usda.gov/download/49285/PDF. The spectra of the various substances are easily distinguishable, allowing the present invention to be used to detect contaminants on stainless steel. For example, FIG. 19A shows a schematic image of a contaminated, stainless steel surface. FIG. 19B shows how the present invention can output an image showing the presence and location of contaminants on the stainless steel surface of FIG. 19A.

In another aspect, the present invention is related to a method to grade meat, implement reliable meat quality control, analyze lean vs. fat ratios, and detect organic material residue on meat processing equipment. The spectra of individual meat properties may be acquired as described herein. These spectra are then analyzed to select the wavelengths necessary to detect or measure the desired meat property. The elements of the filter array are chosen to pass the selected wavelengths such that each image of the multi-camera array represents a different wavelength image. These images are then aligned and analyzed to detect or measure the desired meat property. Sample meats which may benefit from an analysis via the present invention include, but are not limited to, beef, pork, bison, goat, sheep, lamb, other mammalian species, chicken, turkey, other poultry, fish and seafood. Numerous food safety issues can also be addressed with the present invention.

In another embodiment, the present invention would be used to detect fecal contamination on carcasses of species such as beef, pork, poultry, lamb and bison. In fact, the present invention may be used to detect fecal contamination on any number of surfaces.

During poultry processing, the cleanliness of the poultry carcasses is essential. Any fecal contamination on the surface of the carcass can lead to food safety problems which may cause illness or death to consumers and significant financial loss for the poultry processor. Conventional hyperspectral imaging is being investigated as a means for chemical imaging to detect fecal contamination on poultry carcasses. In a recent study, a large, expensive, line-scan, hyperspectral imaging system was found to reliably detect four types of fecal materials (duodenum, ceca, colon and ingesta). Only three wavelengths were used for this detection, 517 nm, 565 nm and 802 nm. Moon S. Kim, Shu-I Tu, Kaunglin Chao, Development of real-time line-scan hyperspectral imaging system for online agricultural and food product inspection, Proc. SPIE 7676, Sensing for Agriculture and Food Quality and Safety II, 76760J ( ); doi:10.1117/12.850460 From Conference Volume 7676, Sensing for Agriculture and Food Quality and Safety II, Orlando, Fla., Apr. 5, 2010. The fecal detection algorithm was based on dual band ratios of 565 nm/517 nm and 802 nm/517 nm followed by thresholding. The spatial images were 118 lines×512 spatial pixels, 0.060 megapixels. This system is estimated to cost $150,000 on one side of a carcass per inspection line with substantial fixturing and complexity.

In one embodiment the present invention is applied to poultry processing and the spectral information derived for the hyperspectral system is used to select the filter array elements of the present invention, for example, 517 nm, 565 nm and 802 nm. The target algorithm may be based on the successful algorithm derived for the hyperspectral system, in the above example, dual band ratios of 565 nm/517 nm and 802 nm/517 nm. However, the spatial resolution is increased from the low-resolution of the hyperspectral system, 0.06 megapixels, to the higher resolution of the present invention, 8 megapixels or perhaps 16 megapixels, greatly increasing the ability to detect small fecal particles that may go undetected with the lower-resolution, hyperspectral imaging system. Additionally, the cost of a system implementing the present invention is estimated to be a small fraction of the cost of a conventional hyperspectral imaging system. The reduction in size and power requirements is also advantageous for the present invention. In a handheld package, perhaps attached to a smartphone, tablet or mini-tablet computer, the present invention could be a mobile device provided to each meat inspector. Incorporated into the production line, the present invention would provide a great cost-performance improvement over the higher cost, low-resolution hyperspectral imaging system. (Note that the conventional hyperspectral imaging system is a significant improvement over current meat inspection practices which are manual inspection or machine vision in the visible spectrum).

Researchers have reported contaminants that may be present on poultry carcasses in the field of poultry processing. B. Park, W. R. Windham, K. C. Lawrence, D. P. Smith, Contaminant Classification of Poultry Hyperspectral Imagery using a Spectral Angle Mapper Algorithm, Biosystems Engineering, Volume 96, Issue 3, March 2007, Pages 323-333. The present invention provides remote and noninvasive techniques to easily and accurately detect such contaminants. Spectral information such as that reported by Park et. al. may be used to select appropriate wavelengths and corresponding filter elements to be used in the practice of the present invention. The resultant filter array and a camera array is then used to capture images of the poultry carcasses to be evaluated for contamination. For example, FIG. 20 schematically shows schematic sample images of poultry carcasses that are then captured using these arrays. A first carcass (on the left) is shown to be uncontaminated, while a second carcass (on the right) is shown to be contaminated from top to bottom by duodenum (triangle), cecum (square), colon (circle), and ingesta (star). The present invention not only detects the contaminants but accurately shows where each contaminant is located in the image of the second carcass. This also is an example of a mode of practice in which the same filter array can be used to detect multiple, specific target substances.

Health

When used to assess health conditions, imaging systems of the present invention may be used to detect and/or assess health conditions of a human or animal subject associated with at least one of arterial disease, venous disease, blood flow, the perfusion of peripheral tissue, a wound, a diabetic foot, tissue perfusion, wound healing for a diabetic subject, peripheral vascular disease, urine analysis, a procedure intended to open an artery or vein, the delivery of cardiopulmonary resuscitation (CPR), an indication of cardiovascular risk via a reactive hyperemia protocol, the degree of vasodilation, vascular clamping during surgery, lymphatic imaging, lymph node mapping, lymph node surgery, breast cancer detection, tumor detection, skin cancer detection, and reproductive status.

Crops Spectral imaging systems of the present invention may be used to assess crop conditions associated with at least one of moisture content, nitrogen content, chlorophyll content, plant maturity, disease state, insect infestation, fungus infestation, mold content, weed content, harvest readiness, soil condition, and fertilizer effectiveness.

Urine

When used to detect urine in a scene, principles of the present invention may be used to assess at least one of determining a quantitative measure of urine characteristics for medical purposes, determining a quantitative measure of urine characteristics for veterinary purposes, determining a quantitative measure of urine characteristics to identify the animal species which provided the urine sample, determining a quantitative measure of urine characteristics in order to identify the specific animal or human subject which provided the urine sample, tracking individual animals for hunting or conservation, identify urine spots on carpet, and walls or flooring for inspection or cleaning purposes.

Algorithms

When analyzing spectral information from captured images, the spectral imaging systems may at least consider one of a ratio of spectral amplitudes at selected wavelengths; a difference (or sum) of spectral amplitudes at selected wavelengths; a principle component analysis of the spectra associated with the target substance; a basis function representation of the target spectrum and background spectra; an eigenvector analysis of the spectra associated with the target substance; other signal processing and statistical methods familiar to those skilled in the art of spectral analysis; and a calibration involving an in-frame reference.

Sanitation

Spectral imaging systems of the present invention may be used to assess sanitation conditions associated with at least one of detecting biofilm on a surface, detecting a surface contaminant, hand washing, egg inspection, food processing equipment, food packaging, meat processing equipment, meat packaging, restaurant equipment, hospital equipment, surgery equipment, a transportation container, a transportation vehicle, a vehicle transporting food products, a vehicle transporting meat products, a vehicle transporting livestock, and a vehicle transporting poultry.

Eggs

Spectral imaging systems of the present invention may be used to assess egg conditions selected from one or more of the stage of embryonic development, the health of the embryonic cardiovascular system, a health condition of the embryo, egg infertility, bacterial contamination, fecal contamination of the egg shells, cracks, blood spots, an addled egg, and the chemical composition of an egg.

Food

Spectral imaging systems of the present invention may be used to assess food conditions associated with at least one of adulterant screening, quality control of food properties, fresh produce quality control for properties, such as bruising, moisture content, and ripeness, grain screening, legume screening, moisture content/control, ingredient control, mixture control, raw component screening, equipment sanitation, packaging quality control, quality control of finished food products, detection of bacterial contamination, and biofilm contamination.

Meat

Spectral imaging systems of the present invention may be used to assess meat conditions associated with at least one of detecting contaminants on meat or carcass surfaces, detecting organic material residue or contaminants on processing equipment, determining meat properties, meat grading, meat quality control, and analysis of lean vs. fat ratios.

Another embodiment of a spectral imaging system 500 is shown in FIG. 21. This embodiment includes advantages such that an interchangeable filter card can be smaller due to closer spacing among filter elements. Also, the system may have a thinner profile since the optical path from the filter card to each image capturing element is substantially parallel to the camera plane.

In more detail, system 500 includes an image capture array of two or more image capture elements 502 and 503 (two such elements are shown for purposes of illustration). Image capture element 502 includes a lens 504, a camera body 506, and an image sensor 508. Image capture element 503 includes a lens 505, a camera body 507, and an image sensor 509.

System 500 further includes a filter card 510 that includes a spectral filter array including two or more spectral filter elements. For purposes of illustration, filter elements 512 and 514 are shown. Filter element 512 is designed to selectively pass a bandwidth portion of the electromagnetic spectrum encompassing a first wavelength, $\lambda_1$. Filter element 514 is designed to selectively pass a bandwidth portion of the electromagnetic spectrum encompassing a second wavelength, $\lambda_2$. In an illustrative mode of practice, the wavelengths $\lambda_1$ and $\lambda_2$ could be selected so that a target substance of interest has a characteristic spectrum such that the ratio and/or other attribute(s) of its spectrum at these two wavelengths distinguishes the target substance from one or more other background substances. In other modes of practice, the value of such ratio might be indicative of the concentration of a target substance in a liquid medium being imaged. System 500 further includes a reflector module 518 having reflector faces 520 and 522.

In use, system 500 is used to capture filtered images of a scene (not shown) to detect the presence, location, and/or quantity of a target substance in the scene. Incoming light 524 is captured and filtered by filter elements 512 and 514 in filter card 510. Filter element 512 selectively passes a narrow bandwidth portion 526 of the incoming light 524. Bandwidth portion 526 in illustrative embodiments has a bandwidth of up to 20 nm, or even up to 15 nm, or even up to 10 nm, or even up to 5 nm or less. Preferably, $\lambda_1$ is located substantially in the middle of this bandwidth. Filter element 514 passes a similar bandwidth portion 528 with respect to $\lambda_2$. Image capture element 502 captures a first filtered image for the filtered bandwidth portion 526. Image capture element 503 similarly and substantially simultaneously captures a second filtered image for the filtered bandwidth portion 528. System 500 includes program instructions that analyze the captured image information to determine if the attributes of the image information at $\lambda_1$ and $\lambda_2$ is indicative of the presence, location, and/or quantity of the target substance at one or more locations in the scene being imaged.

FIG. 22A shows how system 500 can be modified to capture greater numbers of filtered images to provide modified system 600. System 600 includes an image capture array including three image capture elements 602. Filter card 604 includes a spectral filter array including three filter elements 606. Reflector component 608 includes three reflecting faces 610 to reflect, respectively, filtered light to corresponding image capture elements 602. Another modification is shown as system 700 in FIG. 22B. System 700 includes an image capture array including four image capture elements 702. Filter card 704 includes a spectral filter array including four filter elements 706. Reflector component 708 includes four reflecting faces 710 to reflect, respectively, filtered light to corresponding image capture elements 702.

Figure 23:
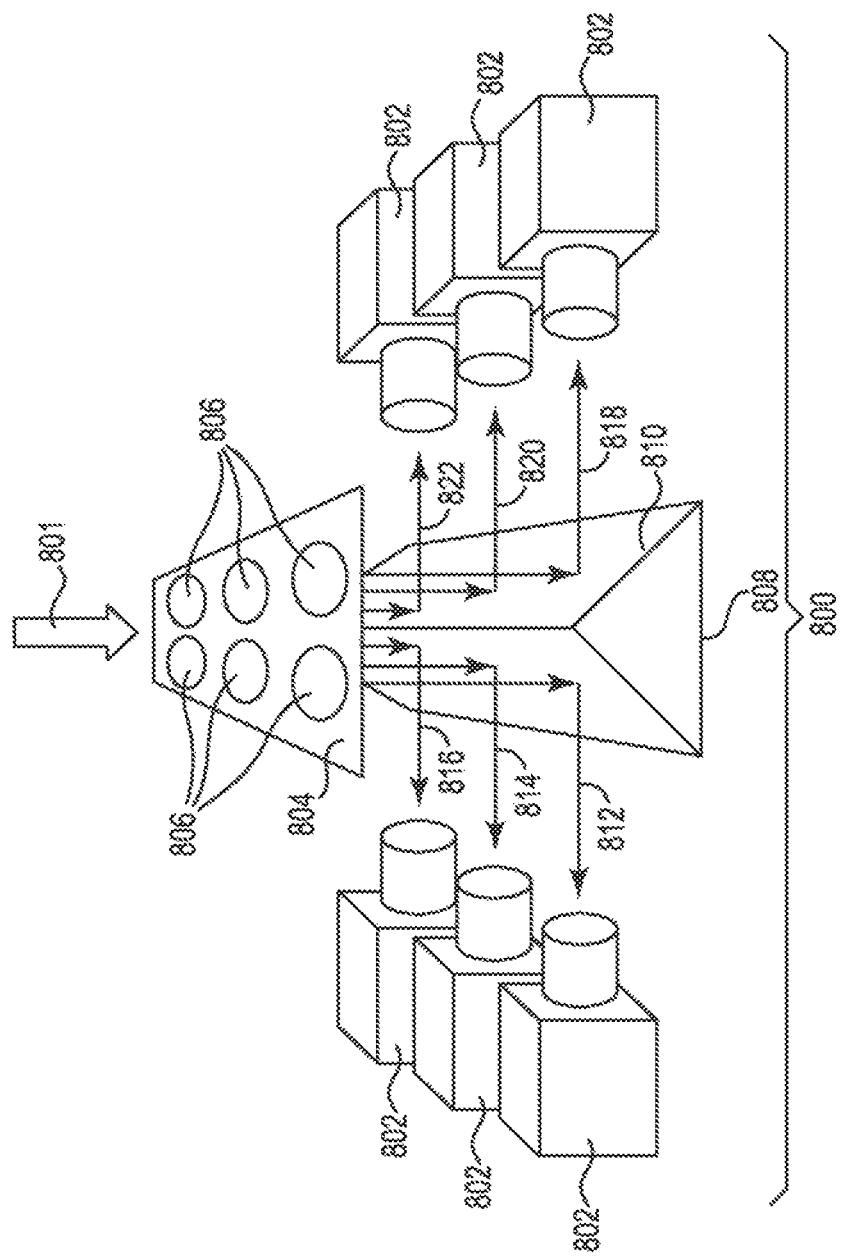
FIG. 23 shows a mirror configuration of the present invention using a six-element image capture array.

FIG. 23 shows another embodiment of a spectral imaging system 800 including an image capture array including six image capture elements 802 arranged in two generally linear sub arrays on each side of a reflector component 808. Reflector component 808 includes two elongate reflector faces 810 that span the lengths of the adjacent arrays of image capture elements 802. Filter card 804 includes a spectral filter array including six spectral filter elements 806. Each spectral filter element filters a pre-selected bandwidth portion of the incoming light 801 to produce corresponding filtered light 812, 814, 816, 818, 820, and 822. In each case, reflector 808 redirects the filtered light 812, 814, 816, 818, 820, and 822 to a corresponding image capture element 802. Each image capture element 802 thus captures a corresponding filtered image. System 800 includes program instructions that analyze the captured image information to determine if the characteristics of the image information at the captured wavelengths is indicative of the presence, location, and/or quantity of a target substance of interest at one or more locations in the scene being imaged.

Figure 24:
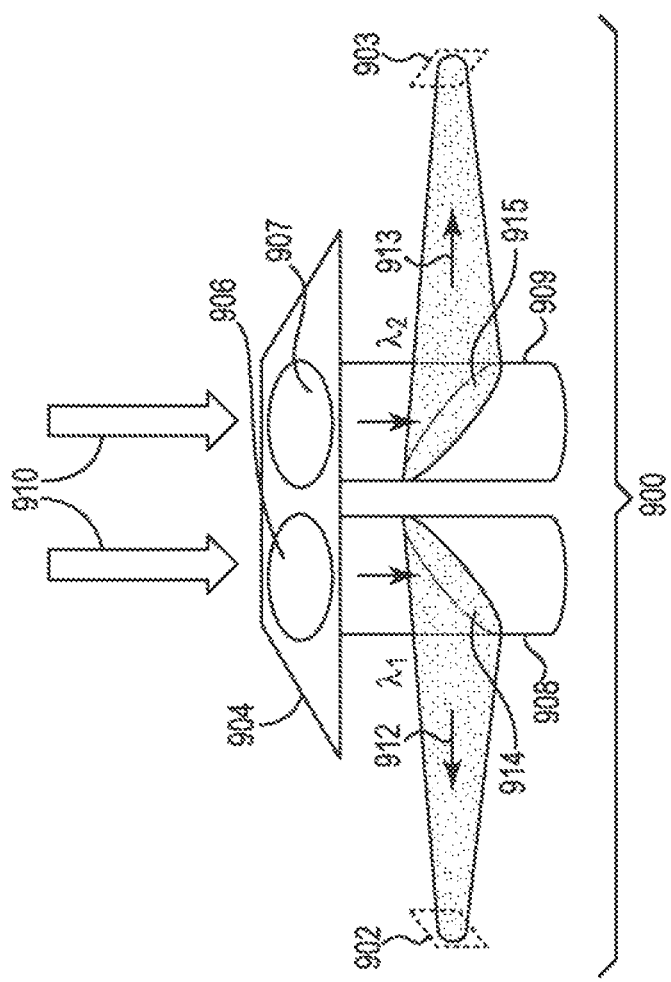
FIG. 24 shows a two-element mirror configuration of the present invention using off-axis parabolic mirrors.

FIG. 24 shows another embodiment of a spectral imaging system 900 including an image capture array including first and second image capture elements 902 and 903. Filter card 904 includes a spectral filter array including first and second spectral filters 906 and 907. Filter 906 has a bandwidth to selectively pass light including $\lambda_1$. Filter 907 has a bandwidth to selectively pass light including $\lambda_2$. Reflector elements 908 and 909 include corresponding off-axis, parabolic mirrors 914 and 915 to reflect and focus light onto a corresponding image capture element 902 or 903. Use of such parabolic reflecting surfaces helps to focus different wavelengths to a common focus. This is one strategy to reduce chromatic aberration effects for different wavelengths. The use of separate image capture elements 902 and 903 also allows each image capture element to optimally focus on a narrow bandwidth of filtered light. This is an additional strategy to help reduce chromatic aberration effects for systems which use a lens as part of the focusing mechanism. All embodiments of the present invention that provide independent focusing of image capture elements share this advantage.

In use, incoming light 910 is filtered by filters 906 and 907, respectively, to provide first filtered light 912 encompassing $\lambda_1$ that is parabolically reflected and focused toward image capture element 902 and second filtered light 913 encompassing $\lambda_2$ that is parabolically reflected and focused toward image capture element 903. Image capture element 902 captures filtered light 912, while image capture element substantially simultaneously captures filtered light 913. System 900 includes program instructions that analyze the captured image information to determine if the characteristics of the image information at the captured wavelengths is indicative of the presence, location, and/or quantity of a target substance of interest at one or more locations in the scene being imaged.

The present invention will now be further described with reference to the following illustrative examples.

Example 1

Detection of Water

Figure 25E:
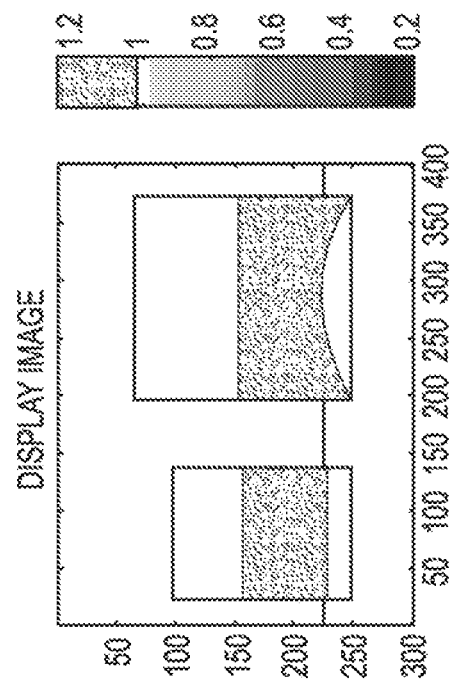
FIG. 25E is an output image created from the reference image, showing regions of the ratio image where the water is present and highlighting the position of water via a custom colormap.
Figure 25D:
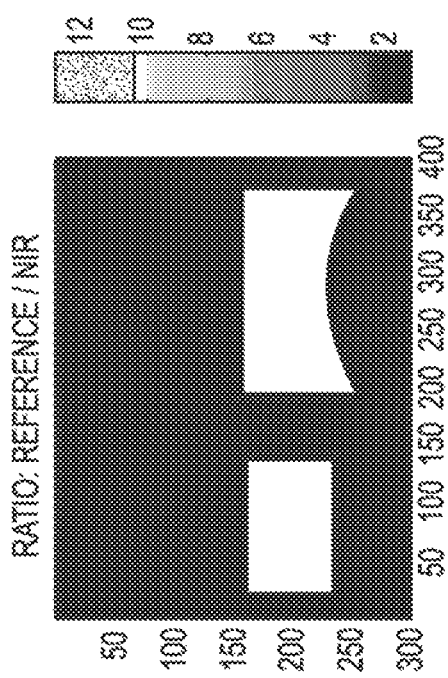
FIG. 25D is a ratio image representing the reference image divided by the NIR image.

Referring to FIGS. 25A to 25E, the principles of the present invention are illustrated by an example having two glass vessels partially filled with water that are within the field of view of a spectral imaging system of the present invention. The system is used to detect the presence of water in the two vessels. In each of FIGS. 25A through 25E, the vessel on the left is a round drinking glass. The vessel on the right is a square glass flower vase with a bottom of non-uniform thickness. It is desired to generate a display image that shows the position of the water within each vessel, as well as an indication of the spatial position of objects within the field of view. FIG. 25A is a 'full spectrum' image taken with the narrower visible spectrum filter removed (typically included with digital cameras); FIG. 25B is an NIR detection image, sensitive to a narrow bandwidth centered on the absorption peak of water at 980 nm. FIG. 25C is a spectral reference image centered in an area of the spectrum which exhibits little spectral absorption for water at 766 nm. FIG. 25D is a ratio image representing the reference image divided by the NIR image. FIG. 25E is a display image created from the reference image, those regions of the ratio image where the water is present, and a custom colormap to highlight the position of water. A reference spectrum for water is shown in FIG. 2A.

In order to detect the water within the two vessels, it is first necessary to examine the spectrum of water. FIG. 2A shows the absorption spectrum for water in the visible and near-infrared regions. Water exhibits a large absorption peak near 980 nm with minimal absorption elsewhere in this spectral region. Therefore, two wavelengths are selected to distinguish water from other background, namely 980 nm at the absorption peak and 766 nm, in a region of the spectrum with minimal absorption.

A detection image is assigned to the wavelength of 980 nm in order to capture the absorption peak and a reference image is assigned to 766 nm, since minimal absorption is evident at this wavelength. Since the assigned wavelength of the reference image exhibits little absorption, and the reference wavelength is close to the visible spectrum, the reference image at 766 nm will also be used as the spatial reference image. Based on these assignments, a multi-camera array with two elements is used to capture filtered images corresponding to each of the two wavelengths. The multi-filter array uses two filter elements, namely, 980 nm and 766 nm.

Elements of the filter array and the multi-camera array were optically aligned in order to acquire the set of images. While numerous automated alignment methods are available, these two example images were manually aligned by inspection. Both the detection image and the reference image were normalized for illumination based upon the intensity of the sheet of paper beneath both vessels. This normalization accounts for filter calibration, illumination normalization, and sensor calibration since it is based on the intensity of an equivalent in-frame reference with uniform spectral properties at the two wavelengths of interest.

While sophisticated, multivariate approaches exist to detect the information regarding the target substance, the presence of water was determined in this example by computing the ratio of the detection image to the reference image. Regions of the resulting image above a given threshold were determined to be the pixels associated with the presence of water. More specifically, the values of the reference image were divided by the corresponding values of the NIR detection image with the result as shown in FIG. 25D. Because the pixels associated with water are darker (lower in numeric value) in the detection image, FIG. 25B, the resulting ratio is larger for those pixels representing water, FIG. 25D.

A display image (FIG. 25E) was computed from the spatial orientation image (also the reference image in this example) and the ratio image. First, the display image was assigned the exact values of the spatial orientation image. This will permit those regions of the field of view that do not contain water to be seen as they appear in the visible spectrum. Then the ratio image was interrogated to identify those pixels with values greater than the threshold value, namely, those pixels visible in FIG. 25D representing water. Next the values of the ratio image greater than the threshold are transported to the display image in their corresponding positions, the result being a display image having the exact values of the spatial orientation image where there is no water present and a display image having values equivalent to the ratio image where there is water present.

Figure 26:
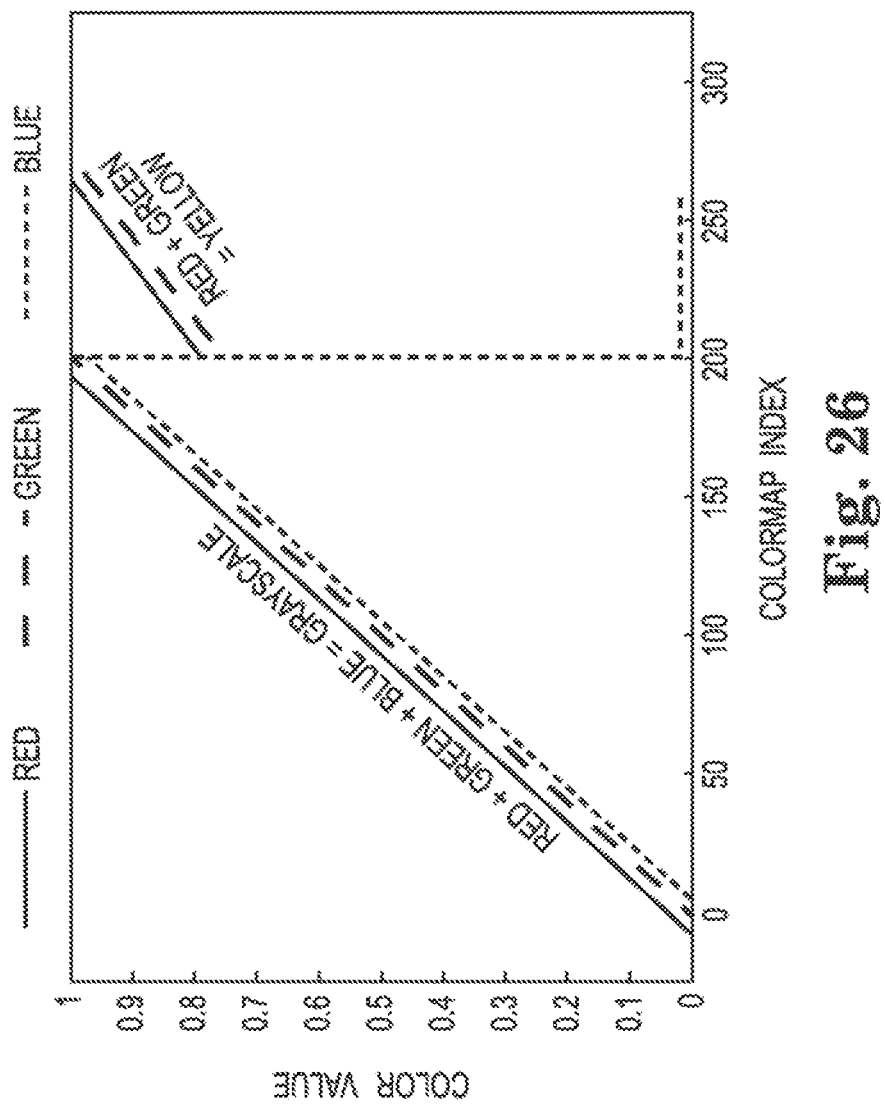
FIG. 26 shows a colormap index to highlight the presence of water in the output images shown in FIG. 25E.

The final step in creating the desired display image is to create a custom colormap that highlights the presence of water in the display image, FIG. 25E. The colormap, as implemented in FIG. 26, includes a matrix that is typically 256 rows by 3 columns. The columns represent the colors red, green and blue respectively. The rows represent the values for each color in its respective column. FIG. 26 shows such a custom colormap. For most of the range of values within the display image, the red, green and blue values are equal resulting in a grayscale image. For values near the top of the display range, the blue column is zero with equal red and green values. Equal red and green values, with no blue, result in yellow.

The slope on the yellow segment of the colormap, as shown, is relatively shallow. This implementation shows little change in color intensity for varying values within the image. As shown, this colormap is best for indicating the presence of the target substance. If it is desirable to indicate a quantity of the target substance, the slope of the red-green line may be increased to provide a greater variation in color intensity over the same range of image values. The selection of column combinations provides a vast color palate to indicate any number of target parameters.

Figure 27:
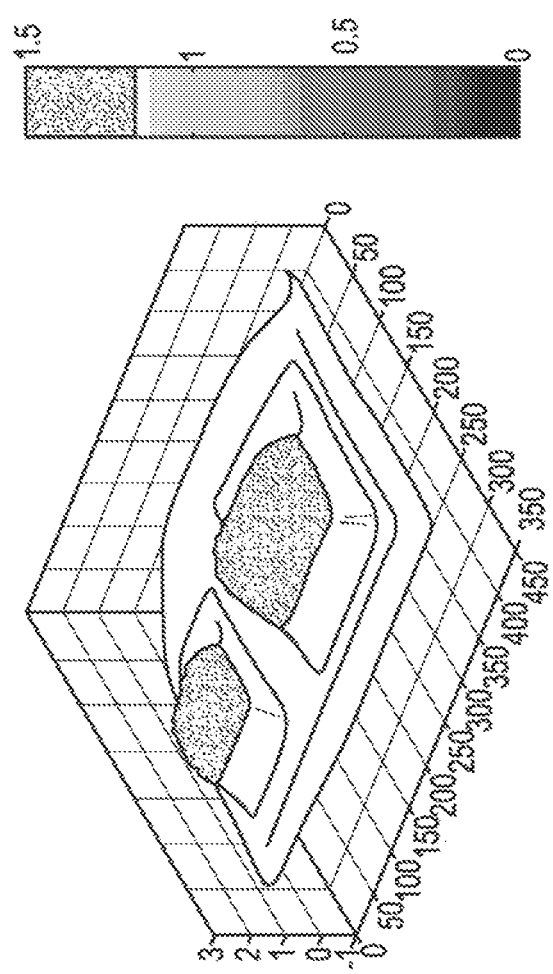
FIG. 27 shows an output image that highlights the presence of water in a scene.
Figures 28A, 28B, 28C:
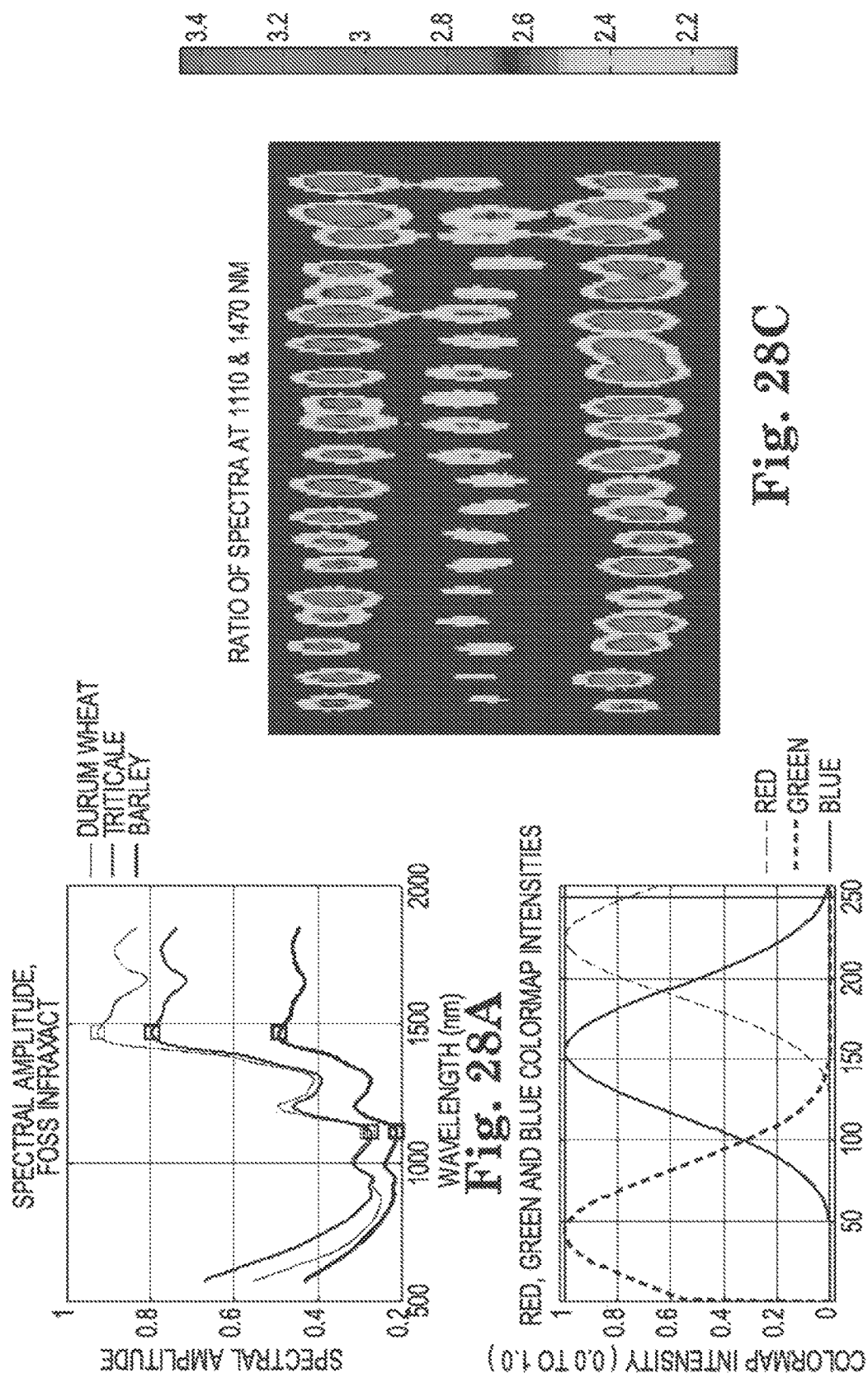
FIG. 28A shows spectral information for barley, durum wheat, and triticale.
FIG. 28B shows an illustrative colormap used to generate the output image of FIG. 28C.
FIG. 28C shows how the spectral information of FIG. 28A and the colormap of FIG. 28B is used to detect barley in a scene relative to durum wheat and triticale.

FIG. 27 shows another way to generate an output image based on the images obtained in FIGS. 25A to 25E. The water presence is highlighted, e.g., shown as yellow or shaded as shown, while the non-water region of the image is a grayscale representation of the spatial image showing the spatial position of objects that contain no water. A custom colormap is applied to a three-dimensional graph of the display image, FIG. 25E. The higher values, represented with highlighted, e.g., highlighted with yellow or shading as shown, were inserted into the image from the ratio image, representing the presence of water.

Example 2

Hyperspectral Imaging for Obtaining Reference Spectral Information

This example shows how spectral information determined by hyperspectral studies may be useful to the present invention in helping to select the center wavelengths of the filter array elements for detection of a particular target substance.

This study was performed with respect to durum wheat, triticale, and barley. FIG. 28A shows spectra obtained with FOSS instruments showing the position of the selected wavelengths on the average spectra for the three grain types. From these spectra, it is determined that spectral characteristics of barley at 1110 and 1470 nm could be used to distinguish barley from the other two grains. FIG. 28B shows a custom colormap applied to the ratio values at these two wavelengths. FIG. 28C shows the resulting spatial image with detected areas indicating the ratio of the selected spectral amplitudes. The top row of images corresponds to wheat, the middle row to barley, and the bottom row to triticale. Barley may be clearly distinguished from the other two grains due to the lower ratio, while durum and triticale kernels are shown to be much closer in chemical composition. This is expected since triticale is a hybrid of durum wheat.

In the practice of the present invention, spectral imaging can therefore be used to distinguish barley from the other two grains. A multi-camera array would capture at least first and second images of the grains of interest through spectral filters allowing a first image to be captured for 1110 nm and a second image to be captured for 1470 nm. If desired, a third spatial reference image can be captured. The ratio of the spectral response at each of the two wavelengths is computed. Pixels in which the ratio is below a threshold are assigned to the background, pixels with the ratio in a first range may be assigned to barley, while pixels with a ratio in a higher range may be assigned to durum and triticale. FIG. 28C shows the display image capability with this kind of analysis.

It is worth noting that an algorithm developed for a conventional hyperspectral imaging system, requiring a first or second derivative of the continuous spectrum, may not be best suited for implementation in the present invention. Such hyperspectral derivative computations, seeking to detect a rapidly changing slope (first derivative) or rate of slope change (second derivative), typically depend on a large number of contiguous spectral samples. The present invention focuses on a lower number of discrete, non-contiguous spectral samples. However, if a key spectral characteristic happens to be a rapidly changing spectral slope, selected wavelengths of the present invention may be strategically placed along the desired slope in order to detect the necessary characteristic. In general, slope calculations are susceptible to noise contamination in the data. Therefore, the strengths of the present invention, namely, to seek spectral levels rather than slope calculations, provides a preference for reliable data analysis—which is an advantageous signal processing strategy for even hyperspectral systems.

Example 3

Egg Inspection

As an example of the flexibility of the present invention, egg spectral data of U.S. Pat. No. 4,182,571 (issued 1980) are used to select filter wavelengths and determine an algorithm to discriminate between good and defective eggs. While U.S. Pat. No. 4,182,571 teaches an optical system to obtain a single measurement per egg using three wavelengths, the present invention permits a high resolution image of each egg using two wavelengths implemented in the fashion of the present invention, namely, two filter elements on a filter card processing a similar number of high resolution images. Wavelengths of 567 nm and 610 nm are selected based on the spectral information. In this embodiment, the present invention provides an analysis for each pixel in the egg image. The image can be analyzed at lesser resolution if desired.

This example shows that practice of the present invention may be used to discriminate between good and defective eggs. As compared to U.S. Pat. No. 4,182,571, the present invention accomplishes this with improved precision due at least in part to the greater resolution achieved by the image capture methodology of the present invention. Additionally, the present invention, by analyzing each pixel of a high-definition image, have used the difference between blood detection and other spectra to image the vasculature within an egg. This allows the monitoring and measurement of fertilized egg development.

Figure 29A:
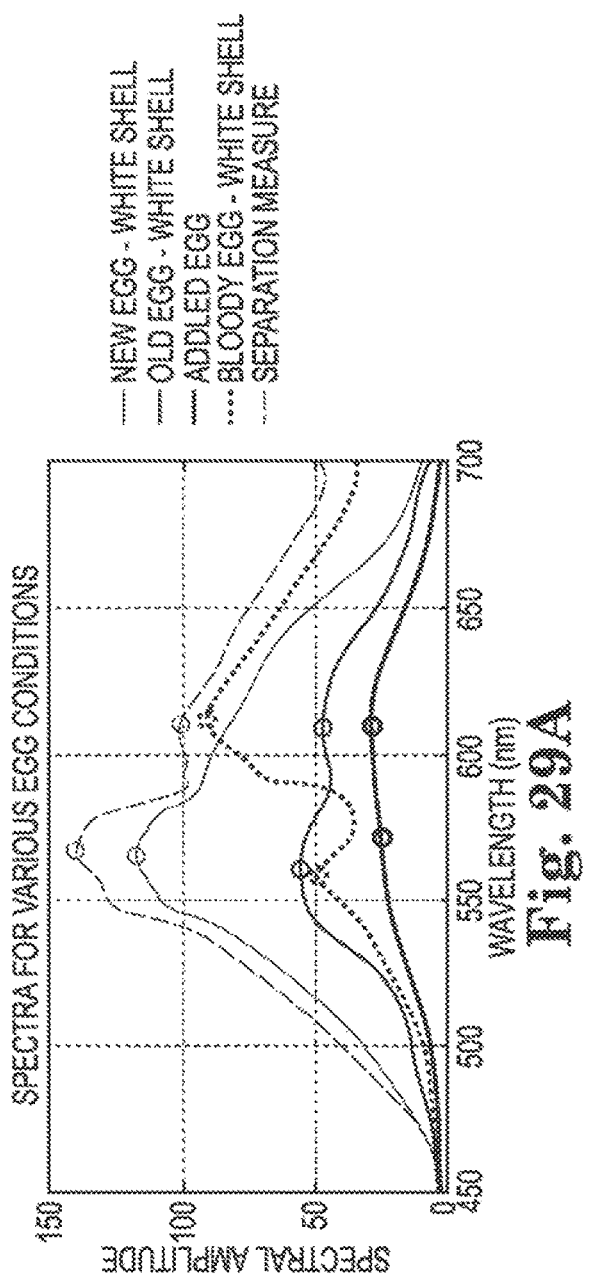
FIG. 29A shows spectral information for egg conditions.

The spectral data for four egg conditions are shown in FIG. 29A. These are candling transmission spectra for white shell eggs including a new egg, old egg, addled egg, and bloody egg, redrawn after data presented in U.S. Pat. No. 4,182,571. The processing illustrated in FIG. 1 is applied to these spectral data.

Figure 29B:
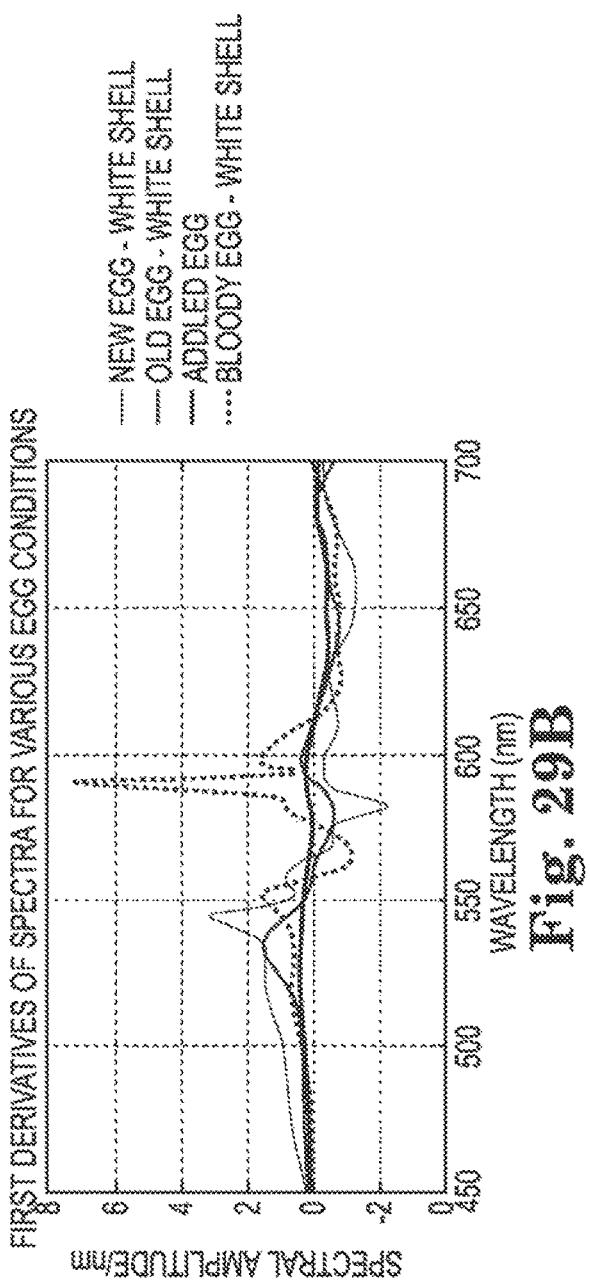
FIG. 29B shows first derivative spectral information for the spectral information of FIG. 29A.
Figure 30:
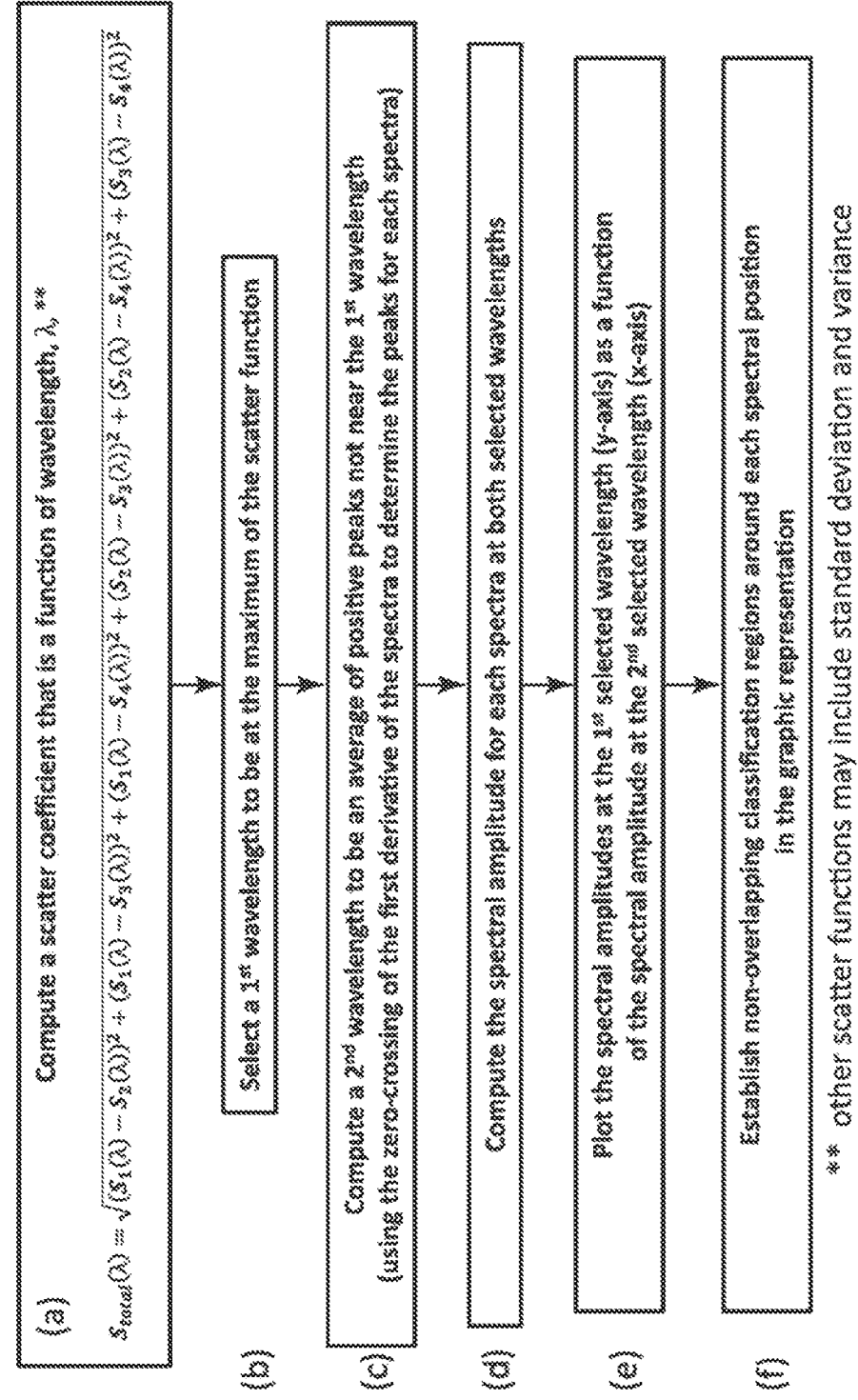
FIG. 30 shows an example algorithm for identifying spectral wavelengths to use for detection of the egg conditions whose spectral information is shown in FIG. 29A.

The exemplary methodology of FIG. 30 was used to create a target algorithm to identify different egg conditions. In step (a), a scatter coefficient was computed as a function of wavelength (not shown). This scatter coefficient was used to help determine an optimal selection of wavelengths in order to distinguish one egg condition from another using the egg spectral information shown in FIG. 29A. The scatter coefficient is a measure of the variation or dispersion of these spectral data at each wavelength. This representative formula serves as an example of numerous measures of dispersion. Alternative examples include standard deviation and variance. The first wavelength, $\lambda_1$, to be used in the analysis was selected to coincide with the peak in the scatter coefficient function in step (b), since at this wavelength the differences among spectra are greatest. In step (c), the positive to negative zero crossing of the first derivative of each spectrum (shown in FIG. 29B) was used to locate the wavelengths corresponding to positive peaks in each spectra at a predetermined distance from the first selected wavelength. The second selected wavelength, $\lambda_2$, was computed to be the average of these positive peak wavelengths. Step (d) in FIG. 30 was a computation of each spectral amplitude at each of the selected wavelengths. Step (e) involved plotting the spectral amplitude for $\lambda_1$ as a function of $\lambda_2$. From this plot, non-overlapping classification zones may be established as indicated in step (f) and graphed in FIG. 29C. Future data which falls within these classification zones may then classified as one of the predetermined classes of egg conditions, namely, new egg, old egg, addled egg, or bloody egg for this example.

While this example includes data from only two wavelengths, resulting in a 2-dimensional classification space, the present invention allows the selection of n wavelengths for analysis, if desired, resulting in an n-dimensional classification space. Similarly, the scope of the present invention includes both the circular classification zones shown in FIG. 29C, and the expanded n-dimensional classification zones for the case of n selected wavelengths. FIG. 29C is a plot of spectral amplitudes for each egg condition with the spectral amplitude at 610 nm as the x-axis and the spectral amplitude at 567 nm as the y-axis. Note from FIG. 29C that the new egg data is a substantial distance from the other egg conditions, a characteristic that makes new, good eggs relatively easy to distinguish from defective eggs. Additionally, the present invention includes classification zone boundaries that are both symmetric and non-symmetric shapes in n-dimensional space that permit an accurate classification of the spectra based on data from the spectral amplitudes at the selected wavelengths.

The present invention also would include the use of numerous additional classification algorithms and methods, known to those skilled in the art, to determine the selected wavelengths to be implemented in the filter array associated with the multi-camera array of the present invention.

Example 4

Vascular Imaging

The present invention was used for vascular imaging. Arteries and veins contain blood with different levels of oxygen attached to the hemoglobin molecules of the red blood cells. A spectral imaging system capable of detecting the different spectral properties of oxyhemoglobin ($HbO_2$) and deoxyhemoglobin (Hb), as shown in FIG. 31, provides an output image indicating vascular structure by determining which pixels within a target field of view fall on arteries and which fall on veins, Additionally, an analysis of the spectra permits an indication of oxygen saturation within viewed tissue based on an analysis of these spectra.

In one aspect, the present invention relates to a method to derive information about arterial blood within the target field of view. The detection of arterial blood, and thus the presence of an arterial vessel, may be accomplished by the present invention using either reflectance or absorption methods via an analysis of the reflectance or absorption spectra for oxyhemoglobin and deoxyhemoglobin. An analysis of the spectra in FIG. 31 was used to select the optimal wavelengths to distinguish an artery from a vein or background tissue based on oxygen saturation. A spatial, point source example of this concept has long been used to noninvasively measure the oxygen saturation of a patient's blood via pulse oximetry devices. In these devices two LED light sources, a red source near 660 nm and a near-infrared source in the range of 905-940 nm are typically used. The ratios of transmitted illumination at these two wavelengths at the appropriate times of the cardiac cycle are used to provide an indication of oxygen saturation for each pixel. The accumulation of the resulting pixels indicating arterial blood is an image showing the arterial vascular structure.

In another aspect, the present invention relates to a method to derive information about arterial and venous blood within a target field of view by implementing the present invention to obtain images through spectral filter elements sensitive to wavelengths in the red and NIR, such as 660 nm and 940 nm. By examining the spectral amplitude at two or more selected wavelengths, based on the spectral characteristics of oxyhemoglobin and deoxyhemoglobin in venous blood, the spatial position of venous blood was determined within the field of view. Further characteristics of venous blood may be determined by examining the spectra of those spatial positions identified as venous blood. A cumulative result of pixels having venous blood provides an image showing the venous vascular structure.

In another aspect, the present invention relates to a method of distinguishing between arteries and veins within the field of view. By knowing the spectral differences between oxyhemoglobin and deoxyhemoglobin it is possible to identify and label, via color-coded overlays on a spatial reference image, the spatial position of arteries and veins within the field of view. FIG. 17 illustrates this principle for a retinal image with a single wavelength. A multiple wavelength embodiment of the present invention will provide even greater differentiation between arteries and veins.

In another aspect, the present invention provides the capability to compute an oxygen saturation image of tissue within the target field of view. Pulse oximetry devices have long been used to provide a noninvasive, point source measurement of the oxygen saturation of a patient's blood. In these devices two LED light sources, a red source near 660 nm and a near-infrared source in the range of 905-940 nm are typically used. The absorption spectra are shown in FIG. 31. The ratios of transmitted illumination at these two wavelengths at the appropriate times of the cardiac cycle are used to compute an indication of oxygen saturation. Similar "point source" measurements for each pixel within the target field of view may be made using the present invention. The cumulative result of these pixel measurements is an image of oxygen saturation for tissue throughout the target field of view.

Example 5

Sanitation

Sanitation of surfaces is a constant challenge in many industries, including the food service industry, the food processing industry, the pharmaceutical industry, the nutraceutical industry, hospitals, clinics, veterinary facilities, and the like. The present invention provides a valuable tool to quickly identify the presence of a contaminant within the target field of view.

Generally, in the context of this example, sanitation involves protecting against contamination. This is distinguished from another aspect of sanitation, which involves the collection and disposal of trash. The present invention provides a powerful tool that can be beneficial to help provide sanitation in an effective and economical manner.

As an example, food processing equipment must be carefully cleaned at regular intervals. After cleaning, each surface of the processing equipment must be carefully inspected to be sure that no contaminants, such as organic particles, biofilms, or cleaning fluid, remain. These contaminants may not be readily visible to the naked eye. The present invention may be used to capture filtered images of surfaces at a plurality of suitable wavelengths, use those images to detect the presence and location of contamination, and then to display each contaminant as a color-coded region on an image of the surface of the food processing equipment. The present invention allows this detection and locating to occur with very high resolution. Such an application for the poultry industry is shown in FIG. 18.

In one aspect, the present invention is related to a method to detect and locate contaminants on a surface which may come into contact with food for human or animal consumption.

In another aspect, the present invention is related to a method to detect and locate contaminants on a surface where the role of target substance and background substance are intentionally reversed. In this aspect the common background surface is identified and the contaminant, in turn, is any substance which is not the background surface. As an example, in the food industry (and many other industries) stainless steel is used as a surface material for countertops and equipment surfaces. In this aspect, the common spectrum of stainless steel is used as the target substance. Any surface area which is not stainless steel is then identified as the contaminant.

In another aspect, the present invention is related to a method to detect and visualize contaminants on any surface which may come into contact with food for human or animal consumption, such as but not limited to, food processing equipment, food preparation surfaces, cooking surfaces, cooking equipment, countertops, vats, beverage containers, storage containers, fermentation containers, stirring vats, pipes, conveyor belts, test equipment, inspection equipment, meat processing equipment, ovens, utensils, vacuum equipment, and bottling equipment.

In another aspect, the present invention is related to a method to detect and visualize contaminants on any food packaging surface which may come into contact with food for human or animal consumption, such as ready to eat packaging, aseptic processing, plastic trays, bags, boxes, cans, cartons, flexible packaging, pallets, and wrappers.

The methods used to detect contaminants on food surfaces may also be used to detect contaminants on the surfaces within food transportation containers or vehicles.

In one aspect, the present invention is related to a method to detect contaminants in any number of transportation containers or vehicles, such as boxcars, trucks, ships, and shipping containers using the methods described herein.

In another aspect, the present invention is related to a method to detect contaminants in transportation containers or vehicles which transport food animals such as hogs, poultry, cattle, and dairy cows.

In another aspect, the present invention is related to a method to detect contaminants on any surface where the spectrum of the surface and the spectrum of the contaminant may be distinguished in a manner described within this specification.

Example 6

Road Conditions

Variations in the condition of road surfaces due to weather conditions are a well-known hazard in many parts of the country. The spectra (acquired by researcher Tom Ulrich Quantifying Spectral Diversity within a MODIS Footprint—Goetz Recipient Research in the Himalayas, http://discover.asdi.com/bid/93042/Quantifying-Spectral-Diversity-within-a-MODIS-Footprint-Goetz-Recipient-Research-in-the-Himalayas) corresponding to each of these conditions is unique and readily distinguished one from the other. Specifically, the spectra emitted by dry roads, slush, snow, ice, and water are different as shown in FIG. 32A. Thus, the present invention is capable of remotely and noninvasively capturing filtered images of a road scene via a traffic camera. The spectral imaging principles of the invention then can be used to accurately identify variations in road conditions, such as snow, ice, slush, wet, salt, hail, mud, gravel, sand, broken glass, and dry as shown in FIG. 32B. Additionally, the display images may be distributed to appropriate personnel and/or drivers via the internet or other communications network.

With regular vision, the portions of a road that are merely wet rather than icy are not easily identified. By capturing filtered images of the road at a plurality of suitable wavelengths, an output image of the road can be generated that clearly shows and distinguishes dry, wet, icy, and snow conditions in the same scene. In another aspect, the present invention relates to a method to detect variations in road surface conditions due to weather, such as snow, ice, slush, wet and dry road as viewed from an automobile with the camera system positioned within or upon the vehicle. In this aspect the detected road condition may be indicated on an output display in a color-coded manner such as is indicated in FIG. 33. The display may be presented to the driver of the vehicle as well as distributed to other drivers via the internet or other communications network. The output can be displayed on a screen in a vehicle or onto a surface of the a windshield or the like using heads up display technology. Driving safety is significantly enhanced when icy locations are pinpointed like this with high precision.

Example 7

Liquid Classification

Each year millions of airline passengers in the United States must limit their carry-on liquids to volumes in order to comply with TSA security regulations. These regulations were established to reduce the chances that dangerous liquids could be smuggled onto an aircraft. The present invention may be used to classify and identify the actual content of the liquids providing greater safety or perhaps providing convenience to passengers by permitting useful volumes of safe liquids. The principles of the present invention may be applied to liquid classification in these and other circumstances.

Figure 34A:
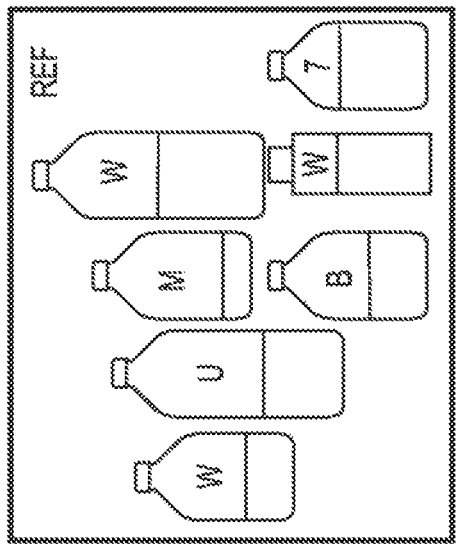
FIG. 34A shows a visible color image (VIS-COLOR, 400-700 nm) of a scene including several liquids held in various containers.
Figure 34B:
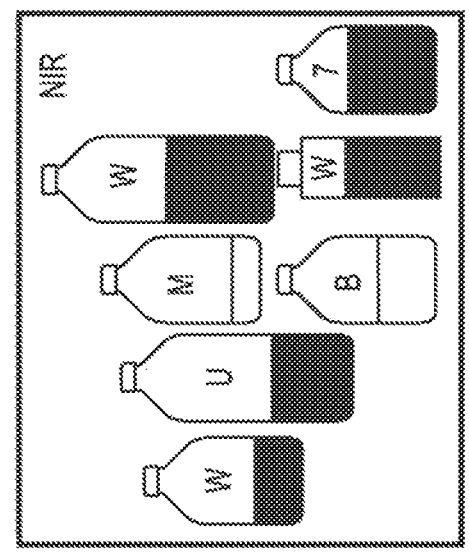
FIG. 34B shows a reference image (REF, 670 nm) of the scene of FIG. 34A.
Figure 34C:
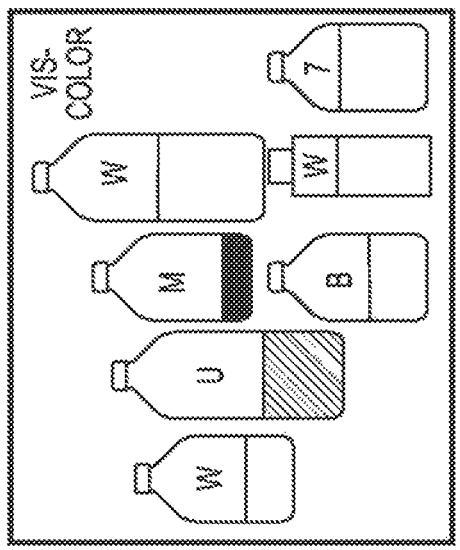
FIG. 34C shows an ultraviolet image (UV, 365 nm) of the scene of FIG. 34A.
Figure 34D:
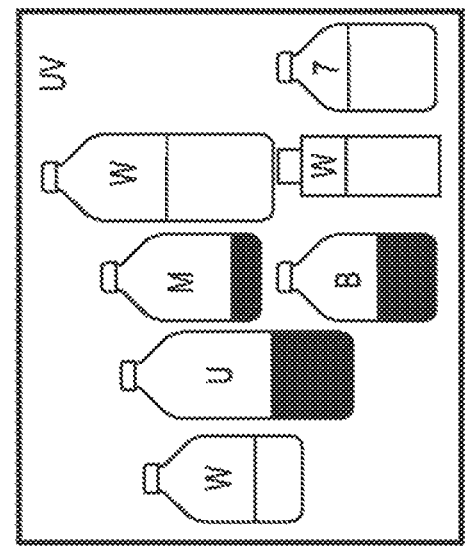
FIG. 34D shows a near infrared image (NIR, 980 nm) of the scene of FIG. 34A, including a classification chart that can be used to detect liquids in the scene of FIG. 34A.

FIGS. 34A to 34D schematically show how liquid classification may be practiced using principles of the present invention. FIG. 34A shows a visible color image (VIS-COLOR, 400-700 nm) of a scene including several liquids held in various containers. FIGS. 34B, 34C, and 34D respectively show a reference image (REF, 670 nm), an ultraviolet image (UV, 365 nm), and a near infrared image (NIR, 980 nm). The bottled liquids were water (W), urine (U), motor oil (M), brake fluid (B), and Seven-Up (7). The letter code and corresponding liquid also are listed in the key in FIG. 34B.

The classification chart of FIG. 34D shows one illustrative classification that is possible using the qualification of 'light' (0) or 'dark' (1) with respect to the appearance of the liquid due to the absorbance associated with the NIR and UV wavelengths. This spectral imaging embodiment easily allows the liquids to be classified into three categories based on NIR, UV and Reference absorption: 1-0-0 liquids (water and 7-up), 1-1-0 liquids (urine), and 0 1 0 petroleum-based liquids (motor oil and brake fluid). Such a system, adapted for other liquids could be applied to classify and screen carry-on liquids for airline security.

In another aspect, the present invention relates to a method to classify and identify liquids in a container using the methods described herein.

Example 8

Sunscreen

This example shows how the present invention can be used to locate where a liquid, dispersion, gel or the like is distributed in a scene. For purposes of illustrating this aspect of the invention, this example shows how spectral imaging can be used to evaluate the extent to which sunscreen is applied to a person. This example also shows how the liquid can be easily detected and located in a scene. The uses of such an embodiment include, but are not limited to, ensuring a complete application of the sunscreen product to all exposed skin areas, a confirmation after a period of time that the applied area is still covered, and the detection of portions of the applied area where the coverage has degraded, perhaps due to perspiration or water exposure, indicating the need to reapply the sunscreen product. In other similar modes of practice, this approach can be used to assess the degree to which a varnish, powder coating, primer, paint, or other coating is applied onto a substrate.

Figure 35A:
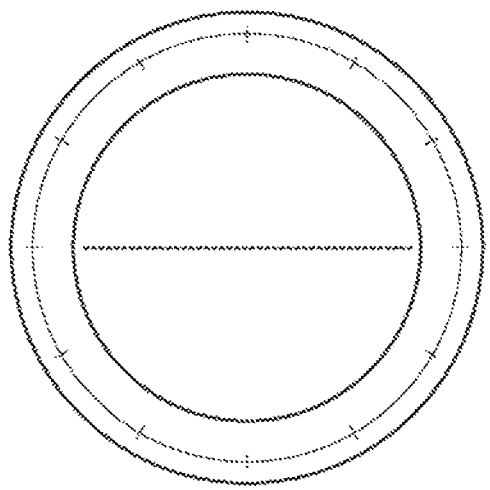
FIG. 35A shows a visible spectrum image of a polystyrene foam plate streaked with sunscreen.
Figure 35B:
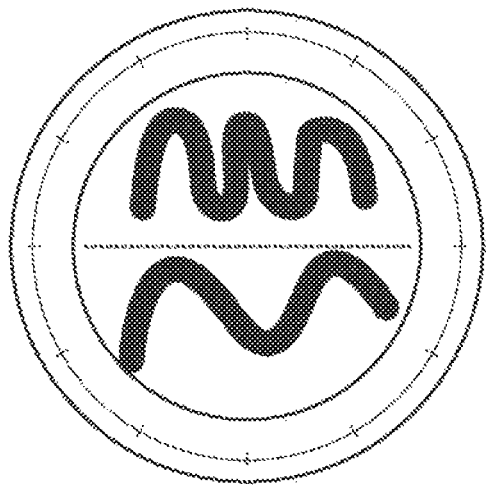
FIG. 35B shows a spectral image of the polystyrene foam plate of FIG. 35A that is acquired using a filter element sensitive to an ultraviolet wavelength at which sunscreen appears darkened.

In practice, a reference image may be a visible spectrum image displayed in grayscale. Detection results can then be highlighted on such an image. The distribution of sunscreen on the skin of the subject shows up very dark when viewed with a spectral filter element that is sensitive to a wavelength in the ultraviolet region of the spectrum. FIG. 35A shows an image of a plate on which sunscreen has been placed. The left half contains Coppertone Sport, SPF 30. The right half contains Banana Boat Lip, SPF 50. In this image, both brands of sunscreen appear to be invisible. Viewed under visible light, the locations of the sunscreen are not easily discernible. FIG. 35B shows an image of the same plate captured with a spectral filter element that is sensitive to a wavelength in the ultraviolet region of the spectrum. An image showing the sunscreen using a filter element passing only an ultraviolet wavelength which shows the absorption of the UV light where the sunscreen is smeared as a very dark region for both sunscreen products. In contrast, the visible spectrum image of FIG. 35A provides little if any visual feedback when applying an invisible sunscreen product to the skin. While the two brands appear similar, they do have different spectral properties. If it was desired to detect and identify the different brands, images at additional, suitable wavelengths could be captured that would allow such differentiation in the images.

Figure 36A:
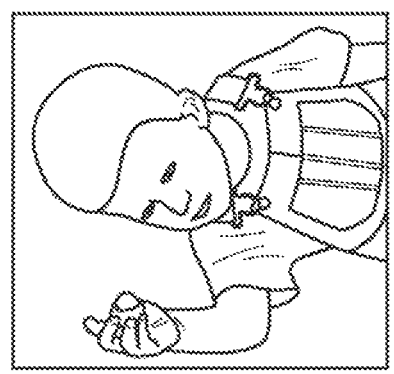
FIG. 36A shows a visible spectrum image of a child wearing sunscreen.

FIG. 36A shows a simulated image in the visible spectrum in which sunscreen is placed on skin areas of a child. The locations of sunscreen on the skin are not visible. FIG. 36B shows a simulated image in which an image of the child is captured using a filter element sensitive to UV light. The areas of skin covered by sunscreen are now easily detected and shown as darker areas. As shown, there are areas of skin which are adequately covered with sunscreen and there are areas which have been missed, leaving the skin susceptible to sunburn. Gaps in coverage are visible around the eyes, on the underside of the forearm, on the hand, and around the neckline.

Figure 37:
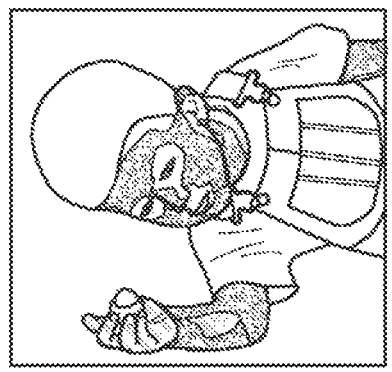
FIG. 37 simulates how the image of FIG. 36B may be highlighted to show protected and unprotected skin areas.

FIG. 37 shows an additional embodiment where at least one additional camera and filter element are used to detect both the regions of the skin covered by the sunscreen as well as the regions of the skin that are not covered with sunscreen.

Figure 36B:
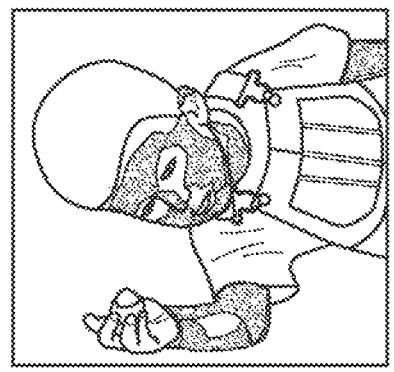
FIG. 36B simulates the image of FIG. 36A captured at a wavelength at which the sunscreen appears darkened.

The image of FIG. 37 is generated by capturing further image information using an additional wavelength in addition to the single wavelength evaluation used to obtain the image of FIG. 36B. With the addition of a second wavelength, uncoated skin also is detected so that both covered and uncovered skin can be identified with respective indicia. In actual practice, the output image can be color-coded to show the application of sunscreen in blue and the uncovered skin in red, representing the potential for sunburn. The color overlays may be applied at a reduced opacity to allow features to be seen through the overlays.

Figure 38C:
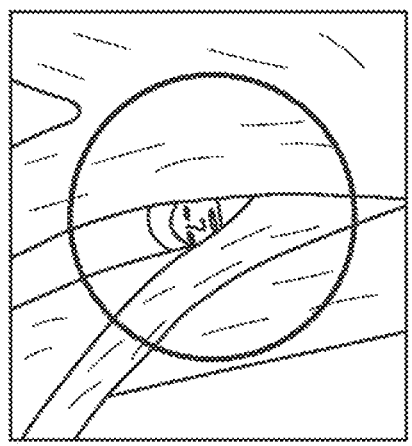
FIG. 38C is a visible spectrum, close up of the scene in FIG. 38A.
Figure 38B:
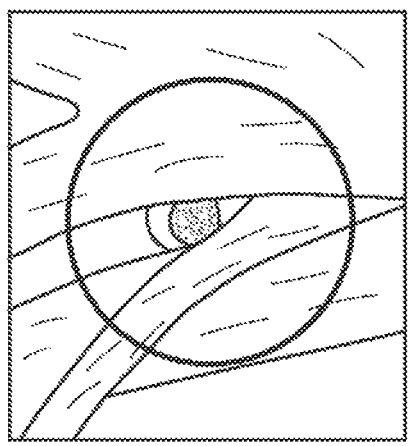
FIG. 38B shows how principles of the present invention may be used to detect and highlight the location of a sunscreen coated surface in the scene of FIG. 38A.
Figure 38A:
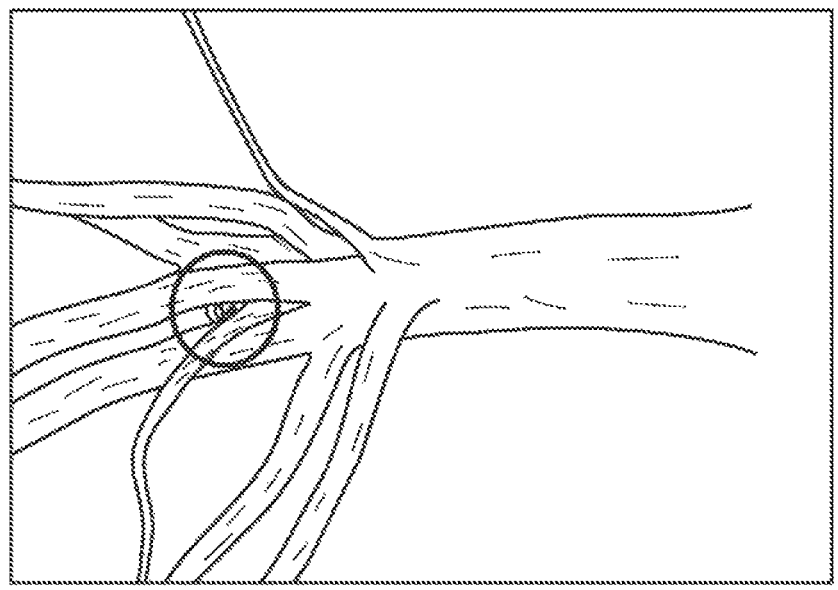
FIG. 38A shows a visible spectrum image of a sunscreen surface hidden in a complex scene.

FIGS. 38A, 38B, and 38C show how easy it is to locate a liquid or surface coating in a scene where visual inspection would be very time consuming or even hopeless. In FIG. 38A, a surface coated with sunscreen is located somewhere in the scene, which is an image captured in the visual spectrum corresponding to what the naked eye sees. The location of the coated surface, sunscreen on a person's face, is hidden in the foliage and difficult if not impossible to discern with the naked eye. For reference, a circle is placed around the region of the image in which the sunscreen placed on person's face is located. Even with this hint, the sunscreen and the person are not easily seen.

Using principles of the present invention, FIG. 38B is a close-up output image derived from spectrally filtered images that allows the sunscreen to be easily detected and located in the scene. The same area bounded by a circle in FIG. 38A is bound by a circle in FIG. 38B. The detected sunscreen area is highlighted with suitable indicia, such as a bright or contrasting color. In some embodiments, the detected area is used to generate the red circle around the sunscreen region. The red circle is then applied back onto the corresponding location in the base image of FIG. 38A.

FIG. 38C is a close-up image of the area of interest in FIGS. 38A and 38B to show how accurately and easily the principles of the present invention make it to locate a coated surface or other substance in an otherwise complex scene.

Example 9

Light Source Identification

Figure 39:
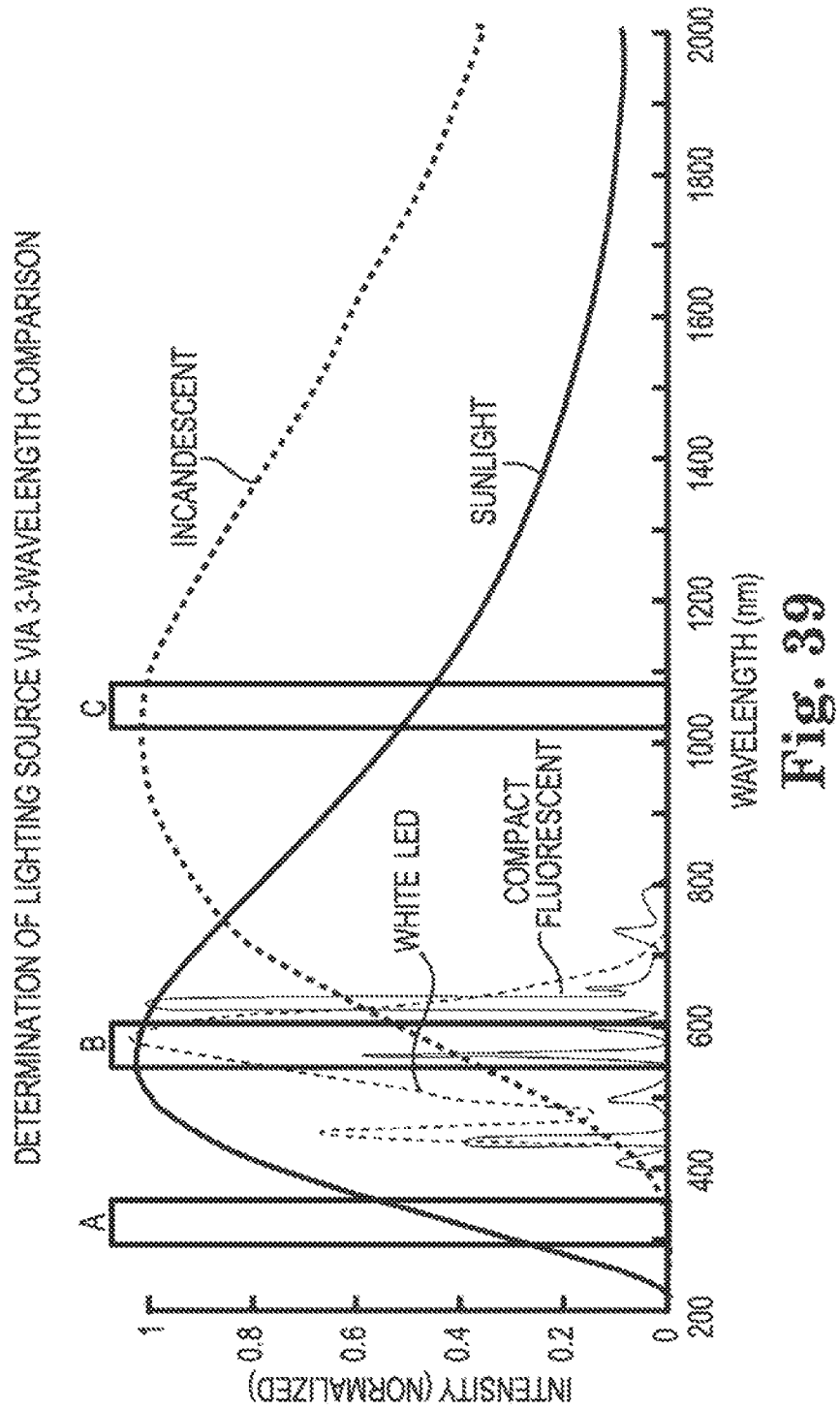
FIG. 39 suggests a means to automatically determine a light source from its spectra for four common light sources.

The present invention optionally may automatically determine the light source in a scene by a comparison of the ratio of light present at selected wavelengths. As an example, FIG. 39 shows the discrimination of four different light sources, namely, sunlight, incandescent, white LED, and compact fluorescent using three wavelength regions, designated as A, B and C. A measurement of light emission at the three wavelength regions, A, B and C, permits a unique determination of which light source is present. The following table associated with FIG. 39 shows the unique relative amplitude of light for each source in the designated wavelength bands:

| Light Source | A | B | C |
|---|---|---|---|
| Sunlight | 45% | 100% | 50% |
| Incandescent | 0% | 50% | 100% |
| White LED | 0% | 100% | 0% |
| Compact Fluorescent | 0% | 50% | 0% |

It should also be noted that it is possible to discriminate between the four sample light sources by using only wavelength bands B and C, a possible reduction in the number of camera/filter elements.

In another aspect, the present invention relates to a method to automatically determine the light source in a scene by monitoring and comparing image data from different selected wavelengths using the methods described herein.

All patents, patent applications, and publications cited herein are incorporated herein by reference in their respective entireties for all purposes. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of detecting a target substance in a scene, comprising the steps of:
   a) using an image capture array and a spectral filter array to simultaneously capture a plurality of spectrally filtered images of the scene, wherein the image capture array has a field of view that is aimed at the scene, wherein the spectral filter array is optically aligned with the image capture array, and wherein the spectral filter array is sensitive to at least two pre-selected bandwidth portions of the electromagnetic spectrum which provide spectral information effective to identify the target substance; and
   b) using the simultaneously captured, spectrally filtered images to generate an output indicative of a presence and one or more locations of the target substance in the field of view.

2. The method of claim 1, further comprising the step of, prior to step a), selecting an interchangeable spectral filter array from a plurality of interchangeable spectral filter arrays configured to be selectively deployed in optical alignment with the image capture array to detect a range of corresponding target substances, wherein the selected interchangeable, spectral filter array is used in step a).

3. The method of claim 2, wherein the interchangeable spectral filter array comprises an interchangeable spectral filter card.

4. The method of claim 2, wherein the image capture array and the optically aligned, selected interchangeable spectral filter array comprise a plurality of channels, and wherein the method further comprises calibrating each channel independently.

5. The method of claim 1, wherein the target substance is moving in the field of view in step a) and wherein the output of step b) comprises a freeze motion image of the moving target substance.

6. The method of claim 1, wherein step a) comprises acquiring a sequence of simultaneously-captured, spectrally filtered images.

7. The method of claim 6, wherein step b) comprises using the sequence of simultaneously-captured, spectrally filtered images to provide the output, wherein the output comprises a sequence of output images.

8. The method of claim 7, wherein the sequence of output images provides a record of the motion of the target substance.

9. The method of claim 7, wherein the sequence of output images preserves relative positions of the moving target substance within the field of view.

10. The method of claim 7, wherein the sequence of output images shows the motion of the moving target substance in the field of view.

11. The method of claim 1, wherein the simultaneously-captured image information comprises spectral information associated with a changing quantity of the target substance in the field of view.

12. The method of claim 11, wherein the output comprises an output image indicative of the changing quantity of the target substance.

13. The method of claim 12, wherein the output comprises a sequence of output images indicative of a changing quantity of the target substance in the field of view.

14. The method of claim 12, wherein the output comprises a video record of the changing quantity of the target substance in the field of view.

15. The method of claim 1, wherein the spectral filter array comprises one or more electronically tunable filter elements.

16. The method of claim 1, wherein the output comprises a plurality of output images and wherein step b) comprises displaying the output images at a selected frame rate.

17. The method of claim 16, wherein the selected frame rate is a video rate.

18. The method of claim 1, wherein the spectral filter array includes at least one polarizing filter.

19. The method of claim 1 wherein step b) comprises adjusting an acquired image for individual camera optics.

20. The method of claim 1, wherein the image capture array and the optically aligned, spectral filter array comprise a plurality of spectral channels, and wherein step b) comprises focusing each spectral channel independently.

21. The method of claim 20, further comprising the steps of focusing a first spectral channel and then focusing an additional spectral channel accounting for wavelength and lens differences between the first spectral channel and the additional spectral channel.

22. The method of claim 1, wherein the target substance is moving in the field of view.

* * * * *